US006506593B2

(12) United States Patent
Mäntylä et al.

(10) Patent No.: US 6,506,593 B2
(45) Date of Patent: Jan. 14, 2003

(54) PRODUCTION AND SECRETION OF PROTEINS OF BACTERIAL ORIGIN IN FILAMENTOUS FUNGI

(75) Inventors: Arja Mäntylä, Helsinki (FI); Marja Paloheimo, Helsinki (FI); Raija Lantto, Klaukkala (FI); Richard Fagerström, Espoo (FI); Tarja Lahtinen, Vantaa (FI); Pirkko Suominen, Helsinki (FI); Jari Vehmaanperä, Espoo (FI)

(73) Assignee: Rohm Enzyme Finland OY, Rajamaki (FI)

( * ) Notice: Subject to any disclaimer, the term of this patent is extended or adjusted under 35 U.S.C. 154(b) by 0 days.

(21) Appl. No.: 09/770,621

(22) Filed: Jan. 29, 2001

(65) Prior Publication Data

US 2001/0024815 A1 Sep. 27, 2001

Related U.S. Application Data

(63) Continuation of application No. 08/590,563, filed on Jan. 26, 1996, now Pat. No. 6,300,114, which is a continuation-in-part of application No. 08/468,812, filed on Jun. 6, 1995, now Pat. No. 5,935,836, which is a continuation-in-part of application No. 08/332,412, filed on Oct. 31, 1994, now abandoned, which is a continuation-in-part of application No. 08/282,001, filed on Jul. 29, 1994, now abandoned.

(51) Int. Cl.[7] ............................................. C07G 17/00
(52) U.S. Cl. .................... 435/267; 435/200; 435/254.3; 435/254.6; 435/320.1; 536/23.2
(58) Field of Search ................................. 435/265, 267, 435/200, 252.3, 252.33, 320.1, 254.3, 254.6; 536/23.2

(56) References Cited

U.S. PATENT DOCUMENTS

| | | | | |
|---|---|---|---|---|
| 5,298,405 A | 3/1994 | Nevalainen et al. | ......... | 435/209 |
| 5,306,633 A | 4/1994 | Gottschalk et al. | ......... | 435/200 |
| 5,364,770 A | 11/1994 | Berka et al. | ............... | 435/69.1 |
| 5,437,992 A | 8/1995 | Bodie et al. | ................. | 435/200 |
| 5,578,463 A | 11/1996 | Berka et al. | ............... | 435/69.1 |
| 5,661,021 A | 8/1997 | Buchert et al. | ............. | 435/209 |
| 5,679,543 A | 10/1997 | Lawlis | ....................... | 435/69.1 |
| 5,935,836 A | 8/1999 | Vehmaanperä et al. | ..... | 435/200 |
| 6,300,114 B1 | 10/2001 | Mätylä et al. | .............. | 435/200 |

FOREIGN PATENT DOCUMENTS

| | | |
|---|---|---|
| CA | 2129171 | 1/1996 |
| DE | 40 00 558 | 7/1990 |
| EP | 0 215 594 | 3/1987 |
| EP | 0 238 023 | 9/1987 |
| EP | 0 262 040 | 3/1988 |
| EP | 0 334 739 | 9/1989 |
| EP | 0 351 655 | 1/1990 |
| EP | 0 383 999 | 4/1990 |
| EP | 0 386 888 | 9/1990 |
| EP | 0 395 792 | 11/1990 |
| EP | 0 463 706 | 1/1992 |
| EP | 0 473 545 | 3/1992 |
| EP | 0 489 104 | 12/1993 |
| WO | WO 89/01969 | 3/1989 |
| WO | WO 89/08738 | 9/1989 |
| WO | WO 90/15860 | 12/1990 |
| WO | WO 91/02791 | 3/1991 |
| WO | WO 91/05908 | 5/1991 |
| WO | WO 93/24622 | 12/1993 |
| WO | WO 93/25671 | 12/1993 |
| WO | WO 93/25693 | 12/1993 |
| WO | WO 94/04664 | 3/1994 |
| WO | WO 95/12668 | 5/1995 |
| WO | WO 97/27306 | 7/1997 |
| WO | WO 98/31821 | 7/1998 |

OTHER PUBLICATIONS

Archer, D. et al., "Strategies for improving heterologous protein production from filamentous fungi," *Antonie van Leeuwenhoek* 65:242–250, Kluwer Academic Publishers (Apr. 1994).

Bailey, M.J. et al., "Interlaboratory testing of methods for assay of xylanase activity," *J. Biotech.* 23:257–270, Elsevier Science Publishers B.V. (1992).

Boel, E. et al., "Two different types of intervening sequences in the glucoamylase gene from *Aspergillus niger*," *EMBO J.* 3: 1581–1585, IRL Press Limited (1984).

Boucher, F. et al., "Complete nucleotide sequence of the xylanase gene from the yeast *Cryptococcus albidus*," *Nucl. Acids Res.* 16:9874, IRL Press Limited (1988).

Ethier, J.–F. et al., "Cloning and characterization of two xylanase genes from *Actinomadura* sp. FC7, a newly isolated thermophilic actinomycete," In: *Industrial Microorganisms: Basic and Appl. Mol. Genet.*, Baltz, R.H. et al., eds., American Society for Microbiology (Proc. 5th ASM Conf. Gen. Mol. Biol. Indust. Microorg., Oct. 11–15, 1992, Bloomington, IN, poster C25).

Ethier, J.–F., "Isolement d'actionmycetes thermophiles et clonage de genes de xylanases," M.Sc. Thesis, University of Sherbrooke, Québec, Canada (1992).

Ethier, J.–F. et al., "Cloning of two xylanase genes from the newly isolated actinomycete *Actinomadura* sp. strain FC7 and characterization of the gene products," *Can. J. Microbiol.* 40:362–368, NRC Research Press (May 1994).

Farrell, R.L. et el., "New bleach sequences of kraft pulp using white white–rot fungi," *Lignocellulosics* pp. 305–315 (1992).

(List continued on next page.)

Primary Examiner—Nashaat T. Nashed
(74) Attorney, Agent, or Firm—Sterne, Kessler, Goldstein & Fox P.L.L.C.

(57) ABSTRACT

The production of thermostable xylanses having bacterial origin is described. These compositions are useful for modifying plant biomass and for enzyme-aided bleaching of wood pulp.

16 Claims, 28 Drawing Sheets

OTHER PUBLICATIONS

Ghangas, G.S. et al., "Cloning of a *Thermomonospora fusca* Xylanase Gene and Its Expression in *Escherichia coli* and *Streptomyces lividans*," *J. Bacteriol.* 171:2963–2969, American Society for Microbiology (1989).

Greiner–Mai, E. et al., "Morphological and Biochemical Characterization and Emended Descriptions of Thermophilic Actinomycetes Species," *System. Appl. Microbiol.* 9:97–109, Urban & Fischer Verlag (1987).

Gwynne, D.I. et al., "Genetically Engineered Secretion of Active Human Interferon and a Bacterial Endoglucanase from *Aspergillus nidulans*," *Bio/Technology* 5:713–719, Nature Publishing Group (1987).

Gwynne, D.I. and Devchand, M., "Expression of Foreign Proteins in the Genus Aspergillus," In: Aspergillus: Biology and Industrial Applications, Bennett, J.W. et al., eds., Butterworth–Heinemann, Boston, pp. 203–214 (1992).

Harkki, A. et al., "A Novel Fungal Expression System: Secretion of Active Calf Chymosin From the Filamentous Fungus *Trichoderma Reesei*," *Biotechnology* 7:596–603, Nature Publishing Group (1989).

Harpin, S., "Cloning and Characterization of Xylanase Genes of the Actinomycetes Actinomadura sp. FC7," M.Sc. Thesis, Department of Sciences, Sherbrooke University, Québec, Canada (May 1993).

Holtz, C. et al., "Production and properties of xylanases from thermophilic actinomycetes," *Antonie van Leeuwenhoek* 59:1–7, Kluwer Academic Publishers (1991).

Ito, K. et al., "Cloning and Sequencing of the xynA Gene Encoding Xylanase A of *Aspergillus kawachii*," *Biosci. Biotech. Biochem.* 56:906–912, Maruzen Company Limited (1992).

Jurasek, L., "Direct biological bleaching of pulps," *Lignocellulosics* pp. 317–325 (1992).

Kalkkinen, N. and Tilgmann, C., "A Gas–Pulsed–Liquid–Phase Sequencer Constructed from a Beckman 890D Instrument by Using Applied Biosystems Delivery and Cartridge Blocks," *J. Protein Chem.* 7:242–243, Kluwer Academic Publishers (1988).

Kelly, J.M. and Hynes, M.J., "Transformation of *Aspergillus niger* by the amdS gene of *Aspergillus nidulans*," *EMBO J.* 4:475–479, IRL Press Limited (1985).

Lantto, R. et al., "Use of Thermostable Xylanases in Softwood Kraft Pulp Pleaching," Presented at the 8$^{th}$ Int. Symp. on Wood and Pulping Chemistry, Jun. 6–9, 1995, Helsinki, Finland.

Lin, L.–L. and Thomson, J.A., "Cloning, sequencing and expression of a gene encoding a 73 kDa xylanase enzyme from the rumen anaerobe *Butyrivibrio fibrisolvens* H17c," *Mol. Gen. Genet.* 228:55–61, Springer–Verlag (1991).

Maat, J. et al., "Xylanases and their application in bakery," In: *Xylans and Xylanases*, J. Visser et al., eds.,Elsevier Science, Amsterdam p. 349–360 (1992).

Parkkinen, E. et al., "Thermostable Xylanases Produced by a Thermophilic *Microtetraspora flexuosa*," (Text of a Poster Presented at the 7$^{th}$ European Congress in Biotechnology, Feb. 19–23, 1995, Nice, France, Poster MAP–191 ECB7).

Parkkinen, E. et al., "Thermostable Xylanases Produced by aThermophilic *Microtetraspora flexuosa*," (Abstract of a Poster Presented at the 7$^{th}$ European Congress in Biotechnology, Feb. 19–23, 1995, Nice, France, Poster MAP–191 ECB7).

Punt, P.J. et al., "Intracellular and extracellular production of proteins in Aspergillus under the control of expression signals of the highly expressed *Aspergillus nidulans* gpdA gene," *J. Biotechnol.* 17:19–34, Elsevier Science Publishers B.V. (1991).

Rowlands, R.T. and Turner, G., "Nuclear and Extranuclear Inheritance of Oligomycin Resistance in *Aspergillus nidulans*," *Mol. Gen. Genet.* 126:201–216, Springer–Verlag (1973).

Sheirlinck, T. et al., "Cloning and expression of cellulase and xylanase genes in *Lactobacillus plantarum*," *Appl. Microbiol. Biotechnol.* 33:534–541, Springer–Verlag (1990).

Shareck, F. et al., "Sequences of three genes specifying xylanases in *Streptomyces lividans*," *Gene* 107:75–82, Elsevier Science Publishers B.V. (1991).

Stangl, H. et al., "Characterization of the *Trichoderma reesei* cbh2 promoter," *Curr. Genet.* 23:115–122, Springer–Verlag (Feb. 1993).

Stoffer, B. et al., "Production, purification and characterization of the catalytic domain of glucoamylase from *Aspergillus niger*," *Biochem. J.* 292:197–202, The Biochemical Society (May 1993).

Svensson, B. et al., "Structure–Function Relationship in Amylases," In: *Biotechnology of Amylodextrin Oligosaccharides*, Friedman, R.B., ed., ACS Symposium Series 458, American Chemical Society, Washington, D.C. (1991).

Uusitalo, J.M. et al., "Enzyme production by recombinant *Trichoderma reesei* strains," *J. Biotechnol.* 17:35–50, Elsevier Science Publishers B.V. (1991).

Viikari, L. et al., "Pulp and the Environment," *Paper and Timber.* 73:384–389, The Finnish Paper and Timber Journal, Publishing Company (1991).

Viikari, L. et al., "Hemicellulases for Industrial Applications," *Biotech. in Agric.* 9:131–182 (Bioconversion of Forest and Agricultural Plant Residues), Saddler, J. eds., CAB Intl. (1993).

Viikari, L. et al., "Xylanases in bleaching: From an idea to the industry," *FEMS Microbiol. Rev.* 13:335–350, Federation of European Microbiological Societies (Mar. 1994).

Whitehead, T.R. and Lee, D.A., "Cloning and Comparison of Xylanase Genes from Ruminal and Colonic Bacteroides Species," *Curr. Microbiol.* 23:15–19, Springer–Verlag (1991).

Wick, C.B., "Enzymology Advances Offer Economical and Environmentally Safe Ways to Make Paper," *Gen. Eng. News*, Mary Ann Liebert, Inc. (Nov. 1, 1994).

American Type Culture Collection, Catalogue of Bacteria and Phages, 18th ed., p. 197, American Type Culture Collection (1992).

World Patent Index, Dialog File 351, Abstract of EP 0 262 040, Fuentes, J.L. et al., "Enzymatic Treatment of Paper Pulp Using Cellulase and/or Hemicellulase Enzyme Preparation to Improve Draining." (Document AN1).

World Patent Index, Dialog File 351, Abstract of EP 0 334 739, (1989) Fuentes, J.L. and Robert, M., "Paper or Cardboard Production—By Enzyme Treatment of Recycled Fibre Pulp to Improve Draining Characteristics." (Document AL2).

World Patent Index, Dialog File 351, Abstract of DE 40 00 558, (1990) Kunnas, A. et al., "Paper–Making with Application of Pulp Suspension to a Sieve Wire—With Addition of Enzyme to Recirculation Water Passing Through Wire to Cleave Deleterious Dissolved Substances Such as Hemicellulose." (Document AN2).

International Search Report issued by PCT International Searching Authority for Application No. PCT/FI97/00037. Mailing Date: May 8, 1997.

Hondel et. al "Development of a System for Analysis of Regulation Signals In Aspergillus," *Molecular Genetics of Filamentous Fungi*, pp. 29–38, Alan R. Liss, Inc. (1985).

Nyyssönen, E. et al., "Efficient Production of Antibody Fragments by the Filamentous Fungus *Trichoderma reesi*," Bio/Technology vol. (May 11, 1993).

Hotz, C. et al., "Production and Properties of Xylanases from Thermophilic Actinomycetes,"*Antoine van Leeuwenhoek* 59:1–7 (Kluwer Academic Publishers) (1991).

EMBL/GenBank/DDBJ database, Accession No. U08894 (Apr. 15, 1994).

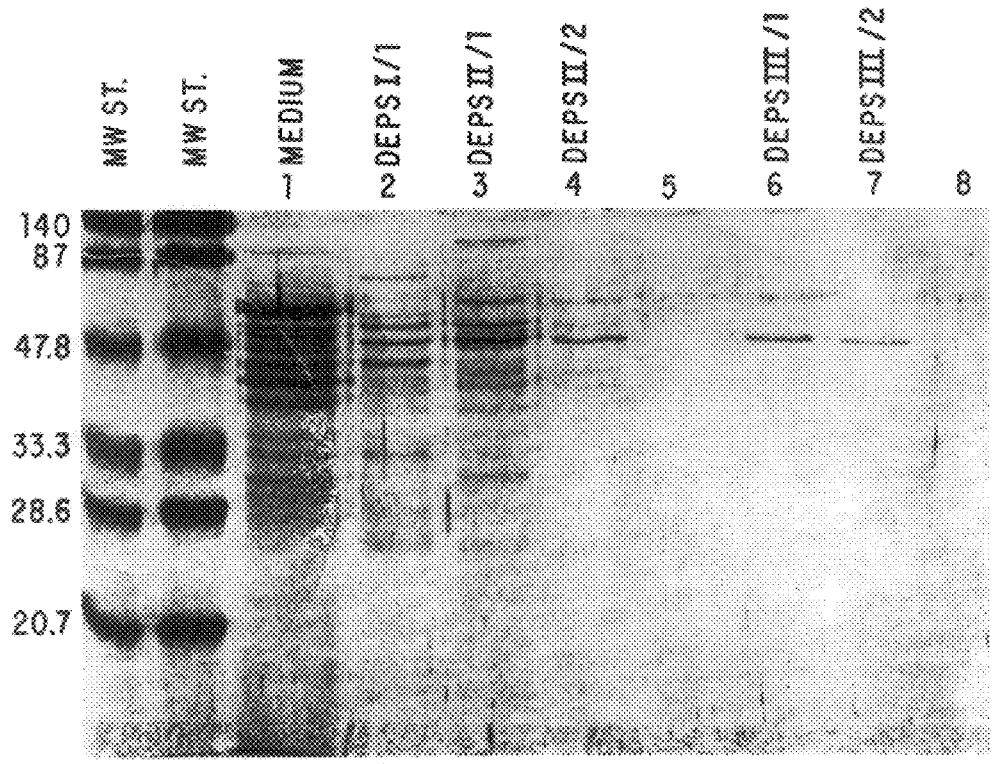
FIG.5  COOMASSIE
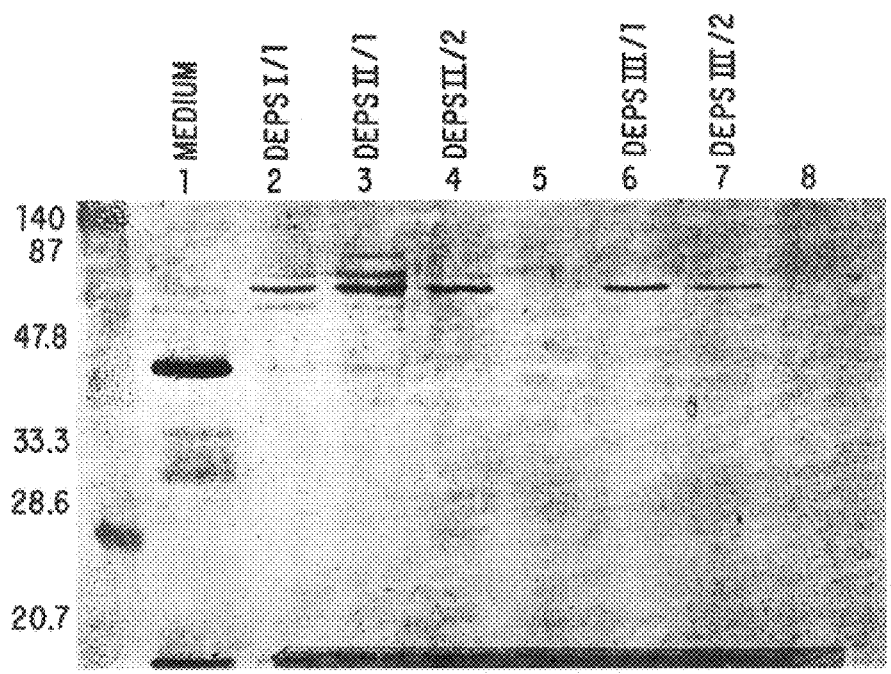
FIG.5A  WESTERN

COOMASSIE

WESTERN

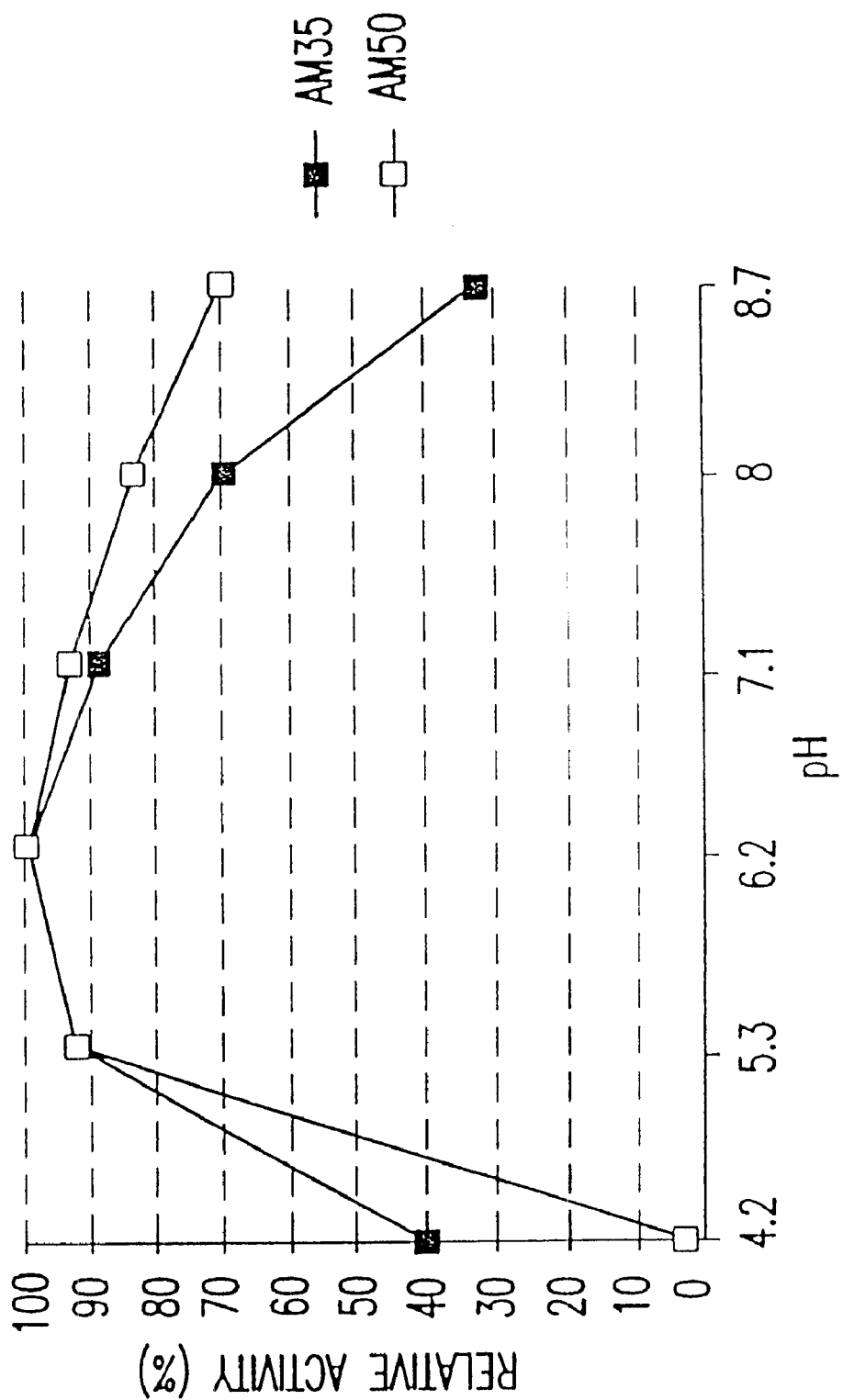

FIG. 13

```
        Y  D  I  Y  E  T  W  R  Y  N  A  P  S  I  E  G  T  R  T  F  Q  Q  F  W  S  V  R  Q  Q  K  R  T  S  G  T  I  I  T
        CATCGGCAACCACTTCGAGCTGGGGCCGCCCGGCCTGGGCGACGGCATGAACCTGGGCCAGCGACTACCAGATCATGGGCGACCAGAGCGGGTAGTCCACCGTCT
                |         |         |         |         |         |         |         |         |         |         |
                                                                                                                    990                                                                                                                  1100

I  G  N  H  F  D  A  W  A  R  A  G  M  N  L  G  S  H  D  Y  Q  I  M  A  T  E  G  Y  Q  S  S  G  S  S  T  V
        CCATCAGGCGAGGGTGGCAACCCGGGCAACCCCGGGTAACCCGGGTAACCCGGGCAACCCGGGTGCGTGGCGTGCTGCGACCCTCTCGCCGGGC
                |         |         |         |         |         |         |         |         |         |         |
                                                                                                                    1210

S  I  S  E  G  G  N  P  G  N  P  G  N  P  G  N  P  G  G  G  C  V  A  T  L  S  A  G
        CAGCAGTGGAGGCGACCGCTACAACCTCAACGTCTCGGTCAGCGGGCATCCCTACCGGCATGCCTACCGGCATGGACGTGCCTACCGGCATCATGCCCACCTGGAAGCAT
                |         |         |         |         |         |         |         |         |         |         |
                                                                                                                    1320

Q  Q  W  S  D  R  Y  N  L  N  V  S  V  S  G  S  N  N  W  T  V  R  M  D  V  P  Y  P  A  R  I  I  A  T  W  N  I
        CCAACGGCCCAGTGCCCCGAGTCCCAGGTGCTCATCGCCAGAGCCCAGGATCCAGCAACGGCAACTGGGGCGTGACGATCCAGCACAACGGCAACTGGACCTGGCCGACGGTCA
                |         |         |         |         |         |         |         |         |         |         |

H  A  Q  W  P  E  S  Q  V  L  I  A  R  P  N  G  N  G  N  N  W  G  V  T  I  Q  H  N  G  N  W  T  W  P  T  V
        CCTGTACCGCGGAACTGAGTTCCCGCCCCCCAAAGGTGGGCGGGGGCTCCCGGCCG
                                                                       ▲
                                                                      1375

```
R  C  I  D  V  P  N  G  N  T  A  D  G  T  Q  V  Q  L  Y  D  C  H  S  G  S  N  Q  Q  W  T  Y  T  S  S  G  E
TCCGGCATCTTCGGGCAACAAGTGCCTGGACGGGGGCACCCAGGTGCTCCAGATCTACAGATGCCACAGCTGTGGGAGCAACCAGCAAGTGGACTCCGGCC                                1540

F  R  I  F  G  N  K  C  L  D  A  G  G  S  S  N  G  A  V  V  Q  I  Y  S  C  W  G  G  A  N  Q  K  W  E  L  R  A
GACGGGCACCATCGTGGGCGTGCAGTCGGGCCTGTGCCTCGACGCGGTGGGCGGCAGCTCCAACGGGGCCGTGGTCCAGATCTACTCCTGCTGGGGCGGCGCCAACCAGAAGTGGGAGCTGCGGGCCAACCA                  1650

D  G  T  I  V  G  V  Q  S  G  L  C  L  D  A  V  G  G  G  T  G  N  G  T  R  L  Q  L  Y  S  C  W  G  G  N  N  Q
GAAGTGGTCCTACAACGCCTGATCCCCGGCTGAGTTGAGGGCGGCACCGGTACGGGTGCTCCGGACCGTCGGAACCGGCACCCGTCCCTTGTTCGTCCAGGACGGAAGGA               1760

K  W  S  Y  N  A
CCGGTCTGAGCAGGCCGGGCCATCGGACACCATGGTGGAGGCCAGGGGTCGTATTCCGACTCCCGGAAGTGGAGGTGTTCCTCCACCTGA                                  1864
```

FIG.14B

```
         10        20        30        40        50        60
AM50   MGVNAFPRPGARRFTGGLYRALAAATVSVVGVVTALTVTQPASAAASTLAEGAAQHNRYF
       | :|::|||||:       ||| |::|::::::::||::: || ||::|||:::||| :|||
U08894 MPINVMPRPGARK------RALLAGAVGLLTAAAALVAPSPAVAAESTLGAAAAQSGRYF
         10                20        30        40        50

70        80        90       100       110       120
AM50   GVAIAANRLTDSVYTNIANREFNSVTAENEMKIDATEPQQGRFDFTQADRIYNWARQNGK
       |:|||::||:||:||:||||||| ||||||||||||||::|:|:|: ||||||||| ||||
U08894 GTAIASGRLNDSTYTTIANREFNMVTAENEMKIDATEPNRGQFNFSSADRIYNWAVQNGK
         60        70        80        90       100       110

130       140       150       160       170       180
AM50   QVRGHTLAWHSQQPQWMQNLSGQALRQAMINHIQGVMSYYRGKIPIWDVVNEAFEDGNSG
       |||||||||||||| |||:||| :|||||||:||:|||::|:||| ||||||||||:||||
U08894 QVRGHTLAWHSQQPGWMQSLSGSSLRQAMIDHINGVMAHYKGKIVQWDVVNEAFADGNSG
        120       130       140       150       160       170

190       200       210       220       230       240
AM50   RRCDSNLQRTGNDWIEVAFRTARQGDPSAKLCYNDYNIENWNAAKTQAVYNMVRDFKSRG
       | |||||||||||||||||||||::||:|||||||||||||||| ||||:||||||||| ||
U08894 GRRDSNLQRTGNDWIEVAFRTARNADPNAKLCYNDYNIENWNWAKTQGVYNMVRDFKQRG
        180       190       200       210       220       230

250       260       270       280       290       300
AM50   VPIDCVGFQSHFNSGNPYNPNFRTTLQQFAALGVDVEVTELDIENAPAQTYASVIRDCLA
       ||||||||||||||||:|||:||||||||:||||||||::|||||::|:: |||:|:::||||
U08894 VPIDCVGFQSHFNSGSPYNSNFRTTLQNFAALGVDVAITELDIQGASPTTYANVVNDCLA
        240       250       260       270       280       290

310       320       330       340       350       360
AM50   VDRCTGITVWGVRDSDSWRSYQNPLLFDNNGNKKQAYYAVLDALNEGSDDGGGPSNPPVS
       |:||  ||||||||||:|||||  |:|||||:|||||:||  |||:|| :|||:|:
U08894 VSRCLGITVWGVRDTDSWRSDQTPLLFDGNGNKKAAYSAVLNAL-----NGGGTSE----
        300       310       320       330       340
```

FIG. 15

```
              370       380       390       400       410       420
AM50    PPPGGGSGQIRGVASNRCIDVPNGNTADGTQVQLYDCHSGSNQQWTYTSSGEFRIFGNKC
        |||:::::|  |:||:|:||:||||::|:||:|:||:|||:|:|||||||:|  |:|::||||
U08894  PPPASDAGTIKGVGSGRCLDVPNASTSDGVQLQLWDCHGGTNQQWTYTDSQELRVYGNKC
          350       360       370       380       390       400

430       440       450       460       470       480
AM50    LDAGGSSNGAVVQIYSCWGGANQKWELRADGTIVGVQSGLCLDAVGGGTGNGTRLQLYSC
        |||:|::||: |||
U08894  LDAAGTGNGTKVQI
          410
```

FIG. 15A

```
              10         20         30         40         50         60
AM50    MGVNAFPRPGARRFTGGLYRALAAATVSVVGVVTALTVTQPASAAASTLAEGAAQHNRYF
        ||  |:||:|:||  :    |||  :|:|:|::|||:::: |  ||:|||:::||| :|||
M64551  MGSYALPRSGVRRSIRVL---LAALVVGVLGTATALIAPPGAHAAESTLGAAAAQSGRYF
              10         20         30         40         50

70         80         90        100        110        120
AM50    GVAIAANRLTDSVYTNIANREFNSVTAENEMKIDATEPQQGRFDFTQADRIYNWARQNGK
        |:|||::||:||:||:||||  ||||||||||||||||||:|:|:|:  |||:||||  ||||
M64551  GTAIASGRLSDSTYTSIAGREFNMVTAENEMKIDATEPQRGQFNFSSADRVYNWAVQNGK
              60         70         80         90        100        110

130        140        150        160        170        180
AM50    QVRGHTLAWHSQQPQWMQNLSGQALRQAMINHIQGVMSYYRGKIPIWDVVNEAFEDGNSG
        ||||||||||||||| |||:|||::||||||:||:|||::|:|||  ||||||||||:||:||
M64551  QVRGHTLAWHSQQPGWMQSLSGRPLRQAMIDHINGVMAHYKGKIVQWDVVNEAFADGSSG
             120        130        140        150        160        170

190        200        210        220        230        240
AM50    RRCDSNLQRTGNDWIEVAFRTARQGDPSAKLCYNDYNIENWNAAKTQAVYNMVRDFKSRG
        |  ||||||:|||||||||||||||  ::||||||||||||:|||| :|||||||||||||  ||
M64551  ARRDSNLQRSGNDWIEVAFRTARAADPSAKLCYNDYNVENWTWAKTQAMYNMVRDFKQRG
             180        190        200        210        220        230

250        260        270        280        290        300
AM50    VPIDCVGFQSHFNSGNPYNPNFRTTLQQFAALGVDVEVTELDIENAPAQTYASVIRDCLA
        |||||||||||||||:|||:|||||||||:|||||||||||::|||||:::||| |||:|::||||
M64551  VPIDCVGFQSHFNSGSPYNSNFRTTLQNFAALGVDVAITELDIQGAPASTYANVTNDCLA
             240        250        260        270        280        290

310        320        330        340        350        360
AM50    VDRCTGITVWGVRDSDSWRSYQNPLLFDNNGNKKQAYYAVLDALNEGSDDGGGPSNPPVS
        |:|| ||||||||||||||||||:|||||:|:|:||:|| ||||||     :||::|||
M64551  VSRCLGITVWGVRDSDSWRSEQTPLLFNNDGSKKAAYTAVLDAL-----NGGDSSEPP--
             300        310        320        330        340        350

370        380        390        400        410        420
AM50    PPPGGGSGQIRGVASNRCIDVPNGNTADGTQVQLYDCHSGSNQQWTYTSSGEFRIFGNKC
        :::|||:||:|:|||:|||||:||||||:|||||:|||||:||||  |:|:|::|:|||
M64551  ----ADGGQIKGVGSGRCLDVPDASTSDGTQLQLWDCHSGTNQQWAATDAGELRVYGDKC
                  360        370        380        390        400
```

FIG. 15B

```
              430       440       450       460       470       480
AM50    LDAGGSSNGAVVQIYSCWGGANQKWELRADGTIVGVQSGLCLDAVGGGTGNGTRLQLYSC
        |||:|:|||: ||||||||||:|||| |::||::|||||||||||||:||:||| :|||:|
M64551  LDAAGTSNGSKVQIYSCWGGDNQKWRLNSDGSVVGVQSGLCLDAVGNGTANGTLIQLYTC
           410       420       430       440       450       460

490
AM50    WGGNNQKWSYNA
        :|:||:|:
M64551  SNGSNQRWTRT
           470
```

FIG. 15C pALK945

MAN...T GGT CGC *GAC ACC ACC...AM35*
        G   R   *D*   *T*   *T*
*man1* sequence    AM35 sequence pALK948

MAN...T GGT CGC GAC AAG CGC *GAC ACC ACC...AM35*
      G   R   D   K   R   *D*   *T*   *T*
            KEX2-linker
*man1* sequence            AM35 sequence pALK1021

MAN...T GGC CAG TGT GGA GGT *GAC ACC ACC ATC ACC CAG AAC...AM35*
      G   Q   C   G   G   *D*  *T*  *T*  *I*  *T*  *Q*  *N*
    *man1* sequence    AM35 sequence pALK1022

MAN...T GGC CAG TGT GGA GGT CGC GAC AAG CGC *GAC ACC ACC...AM35*
      G   Q   C   G   G   R   D   K   R   *D*  *T*  *T*
                      KEX-linker
   *man1* sequence               AM35 sequence

FIG. 19

PRODUCTION AND SECRETION OF PROTEINS OF BACTERIAL ORIGIN IN FILAMENTOUS FUNGI

CROSS REFERENCE TO RELATED APPLICATIONS

This application is a continuation of U.S. appl. Ser. No 08/590,563, filed Jan. 26, 1996, now U.S. Pat. No. 6,300,114, which is a continuation-in-part of U.S. appl. Ser. No. 08/468,812, filed Jun. 6, 1995, now U.S. Pat. No. 5,935,836, which is a continuation-in-part of U.S. appl. Ser. No. 08/332,412 filed Oct. 31, 1994 now ABN which is a continuation-in-part of U.S. Appl. Ser. No. 08/282,001, filed Jul. 29, 1994 now ABN.

FIELD OF THE INVENTION

The present invention is directed to the production of proteins of bacterial origin in the filamentous fungi, for example in Aspergillus and Trichoderma. Preferably, the proteins originate from actinomycetes. The compositions of the invention are useful for modifying plant biomass properties, especially to reduce the lignin content. The invention is also directed to the area of thermostable xylanases that are active at high temperatures and to a method for bleaching with the aid of the enzyme compositions of the invention.

BACKGROUND OF THE INVENTION

The aim of kraft pulp bleaching is to remove the residual lignin that is left in pulp after kraft cooking. Traditionally, this has been done using chlorine-containing chemicals. Because of environmental concerns and consumer demands, alternative bleaching technologies have been desired.

The first biotechnical approach to this problem was to attack the lignin directly with lignin degrading enzymes. However, the chemistry of enzymatic lignin degradation seems to be very complicated and difficult to control.

Lignin can be degraded, if the whole microorganism that produces ligninases is used. However, treatment times are relatively long. For example, treatment times may take days, and the microorganisms need supplemental nutrients to work. It can also be difficult to control the growth of other, undesired, microbes. The use of lignin degradation by isolated ligninases or by microorganisms is the subject of much research. (see, for example, Farrell, R. L. et al., *Lignocellulosics* 305–315 (1992); Jurasek, L., *Lignocellulosics* 317–325 (1992)).

In addition to cellulose and lignin, wood pulp contains hemicellulose. Another approach is to attack hemicellulose—the third main component of wood. The hemicellulose in native hardwood is mainly xylan, while in softwood the hemicellulose is mainly glucomannans and some xylan. During kraft cooking, part of the xylan is dissolved into the cooking liquor. Towards the end of the cooking period when the alkali concentration decreases, part of the dissolved and modified xylan reprecipitates back onto the cellulose fiber.

In 1986, it was noticed that xylanase pretreatment of unbleached kraft pulp results in a lessened need for chemicals in the bleaching process (Viikari, L. et al., Proceedings of the 3rd Int. Conf. on Biotechnology in the Pulp Paper Ind., Stockholm (1986), pp. 67–69). Xylanase pretreatment of kraft pulp partially hydrolyses the xylan in kraft pulp. This makes the pulp structure more porous and enables more efficient removal of lignin fragments in the subsequent bleaching and extraction stages. Later, in several laboratories, the xylanase pretreatment was reported to be useful in conjunction with bleaching sequences consisting of $Cl_2$, $ClO_2$, $H_2O_2$, $O_2$ and $O_3$. See reviews in Viikari, L. et al., *FEMS Microbiol. Rev.* 13: (1994—in press); Viikari, L. et al., in: Saddler, J. N., ed., *Bioconversion of Forest and Agricultural Plant Residues*, C-A-B International (1993), pp. 131–182; Grant, R., Pulp and Paper Int. (September 1993), pp. 56–57; Senior & Hamilton, *J. Pulp & Paper*:111–114 (September 1992); Bajpai & Bajpai, *Process Biochem.* 27:319–325 (1992); Onysko, A., *Biotech. Adv.* 11:179–198 (1993); and Viikari, L. et al., *J. Paper and Timber* 73:384–389 (1991).

As a direct result of the better bleachability of the pulp after such a xylanase treatment, there is a reduction of the subsequent consumption of bleaching chemicals, which when chloride containing chemicals are used, leads to a reduced formation of environmentally undesired organochlorine compounds. Also as a direct result of the better bleachability of pulp after a xylanase treatment, it is possible to produce a product with a final brightness where such brightness would otherwise be hard to achieve (such as totally chlorine free (TCF) bleaching using peroxide). Because of the substrate specificity of the xylanase enzyme, cellulose fibers are not harmed and the strength properties of the product are well within acceptable limits.

However, it is not as simple as merely adding a xylanase treatment step. Most commercial xylanases designed for pulp bleaching are not very thermotolerant, especially when neutral or alkaline pH conditions are used. In practice, xylanases are generally inefficient or inactive at temperatures higher than 60° C.

The cloning of xylanases has been reported from Actinomadura sp. FC7 (Ethier, J.-F. et al., in: *Industrial Microorganisms: Basic and Applied Molecular Genetics*, R. Baltz et al., eds, (Proc. 5th ASM Conf. Gen. Mol. Biol. Indust. Microorg., Oct. 11–15, 1992, Bloomington, Ind., poster C25); bacteria (e.g. Ghangas, G. S. et al., *J. Bacteriol.* 171:2963–2969 (1989); Lin, L.-L., Thomson, J. A., *Mol. Gen. Genet.* 228:55–61 (1991); Shareck, F. et al., *Gene* 107:75–82 (1991); Scheirlinck, T. et al., *Appl Microbiol Biotechnol.* 33:534–541 (1990); Whitehead, T. R., Lee, D. A., *Curr. Microbiol.* 23:15–19 (1991)); and fungi (Boucher, F. et al., *Nucleic Acids Res.* 16:9874 (1988); Ito, K. et al., *Biosci. Biotec. Biochem.* 56:906–912 (1992); Maat, J. et al., in Visser, J. et al., eds., *Xylans and Xylanases* (Elsevier Science, Amsterdam), pp. 349–360 (1992); van den Broeck, H. et al., EP 463,706 A1 (1992), WO 93/25671 and WO 93/25693). It has been proposed by some researchers that the former genus Actinomadura should be divided into two genuses, Actinomadura and Microtetraspora, the latter including, e.g. the former *A. flexuosa* (Kroppenstedt et al., *System. Appl. Microbiol.* 13: 148–160 (1990).

It is known that *Thermomonospora fusca* produces thermostable and alkaline stable xylanases (EP 473,545, Sandoz). The use of hemicellulose hydrolyzing enzymes in different bleaching sequences is discussed in WO 89/08738, EP 383,999, WO 91/02791, EP 395,792, EP 386,888, EP 473,545, EP 489,104 and WO 91/05908. The use of hemicellulolytic enzymes for improved water removal from mechanical pulp is discussed in EP 262,040, EP 334,739 and EP 351,655 and DE 4,000,558. When the hydrolysis of biomass to liquid fuels or chemicals is considered, the conversion of both cellulose and hemicellulose is essential to obtain a high yield (Viikari et al., "Hemicellulases for Industrial Applications," In: *Bioconversion of Forest and Agricultural Wastes*, Saddler, J., ed., CAB International, USA (1993)). Also, in the feed industry, there is a need to use a suitable combination of enzyme activities to degrade the high β-glucan and hemicellulose containing substrate.

A xylanase that is active at an alkaline pH would decrease the need to acidify the pulp prior to xylanase treatment. In addition, the temperatures of many modern kraft cooking and bleaching processes are relatively high, well above the 50° C. that is suitable for many of the commercial bleaching enzymes. Accordingly, a need exists for thermostable xylanase preparations that are stable at alkaline pH's for use in wood pulp bleaching processes.

The efficient and cost-effective production of thermostable xylanases is a problem, because thermostable xylanases originate mainly from relatively unstudied bacteria, which often produce only minimal or very small amounts of xylanase. Further, there may be little or no experience of cultivating these microbes in a fermentor or no fermentation processes available. Furthermore, these microbes may be unsuitable for industrial scale production. On the other hand, filamentous fungi like Aspergillus and Trichoderma are known to produce large quantities of proteins, on an industrial scale. In particular, these fungi have been shown to be suitable for production of homologous or heterologous proteins of fungal origin.

There are, however, very few reports of producing proteins of bacterial origin in filamentous fungi and as far as we know, no reports of the production of proteins of bacterial origin in Trichoderma. Accordingly, a need exists for efficient and cost-effective production of thermostable xylanases of bacterial origin. According to this invention our solution is production in the filamentous fungi and preferably in Trichoderma.

SUMMARY OF THE INVENTION

The invention is directed inter alia, to a method of expressing and secreting proteins of bacterial origin with a high level of expression and secretion. As much as 10-fold greater production and secretion levels than that previously observed have been obtained. The invention, however, may result in either lesser or greater levels of expression.

It is therefore an object of this invention to produce protein of bacterial origin in filamentous fungi such as Aspergillus or Trichoderma. Preferably, the host is Trichoderma and the proteins originate from actinomycetes.

It is further an object of this invention to provide recombinant vectors comprising a DNA sequence encoding a bacterial protein, wherein said bacterial protein encoding sequence is fused in frame with the sequence of a secreted enzyme. Preferably the bacterial protein originates from actinomycetes and the enzyme it is fused to is selected from the group consisting of homologous secretable proteins from filamentous fungi. Most preferably the enzyme is Trichoderma cellulase or hemicellulase, or at least a functional domain of said cellulase or hemicellulase. More preferably the protein from actinomycetes is a xylanase and most preferably an Actinomadura xylanase.

It is further an object of this invention to provide culture medium from the culture of hosts, into which said recombinant vectors have been transformed. Preferably the host is a Trichoderma. More preferably the host is *Trichoderma reesei*.

It is further an object of this invention to provide a method of enzyme-aided bleaching comprising adding said culture medium to pulp.

It is further an object of this invention to provide a method for chemically treating plant biomass with said culture medium.

FIGS.

Figure 1:
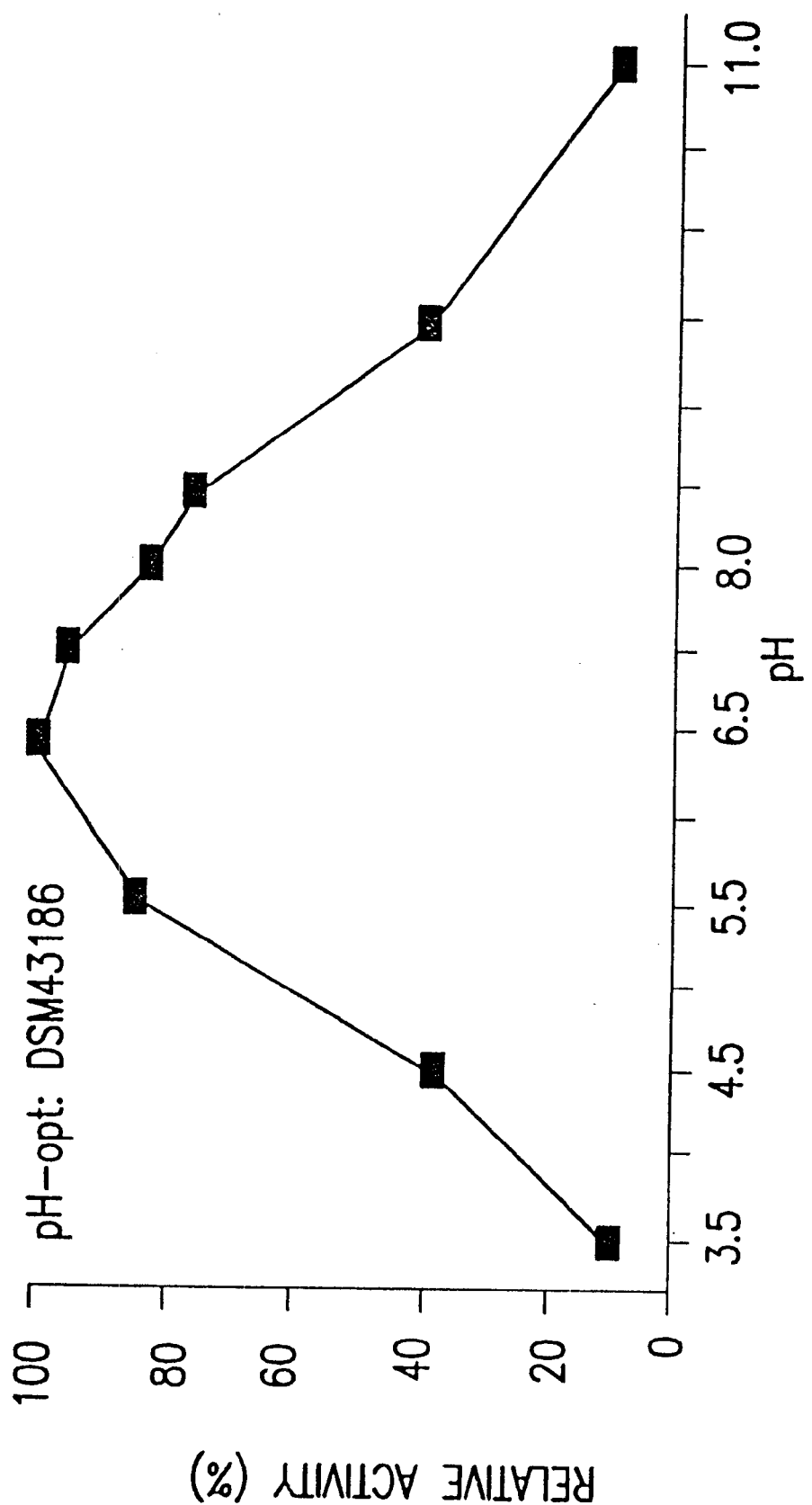
FIG. 1 shows the effect of pH on *A. flexuosa* (DSM43186) xylanase activity (culture supernatant).

FIG. 5 shows the Coomassie Brilliant Blue protein staining pattern of the various chromatographic pools. Two leftmost lanes: molecular weight markers; lane 1: medium; lane 2: DEPS (Pool I/1); lanes 3 and 4: DEPS (Pool II/1 and II/2, respectively); lane 5: empty; lanes 6 and 7: DEPS (Pool III/1 and III/2, respectively); lane 8: empty. DEPS: Fractions after the DEAE chromatography shown in FIG. 3 and the Phenyl Sepharose chromatography shown in FIG. 4.

FIG. 5A shows the Western blot analysis of the various chromatographic pools stained in FIG. 5. Polyclonal antiserum raised against the *T. fusca* TfxA xylanase was used for detection. Leftmost lane: molecular weight markers; lane 1: medium; lane 2: DEPS (Pool I/1); lanes 3 and 4: DEPS (Pool II/1 and II/2, respectively); lane 5: empty; lanes 6 and 7: DEPS (Pool III/1 and III/2, respectively); lane 8: empty. DEPS: Fractions after the DEAE chromatography shown in FIG. 3 and the Phenyl Sepharose chromatography shown in FIG. 4.

Figure 6:
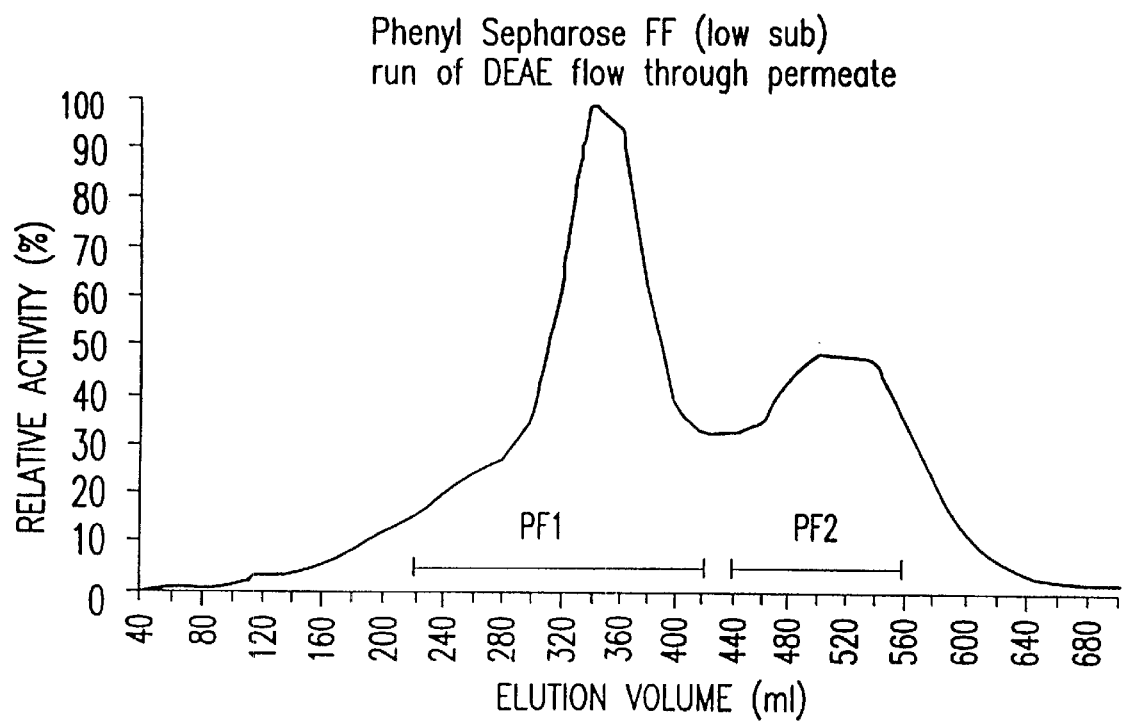

FIG. 6 shows the Phenyl Sepharose FF chromatography elution profile of DEAE flow through permeate. The tubes that were combined to provide sample PF1 and PF2 are indicated.

Figure 6A:
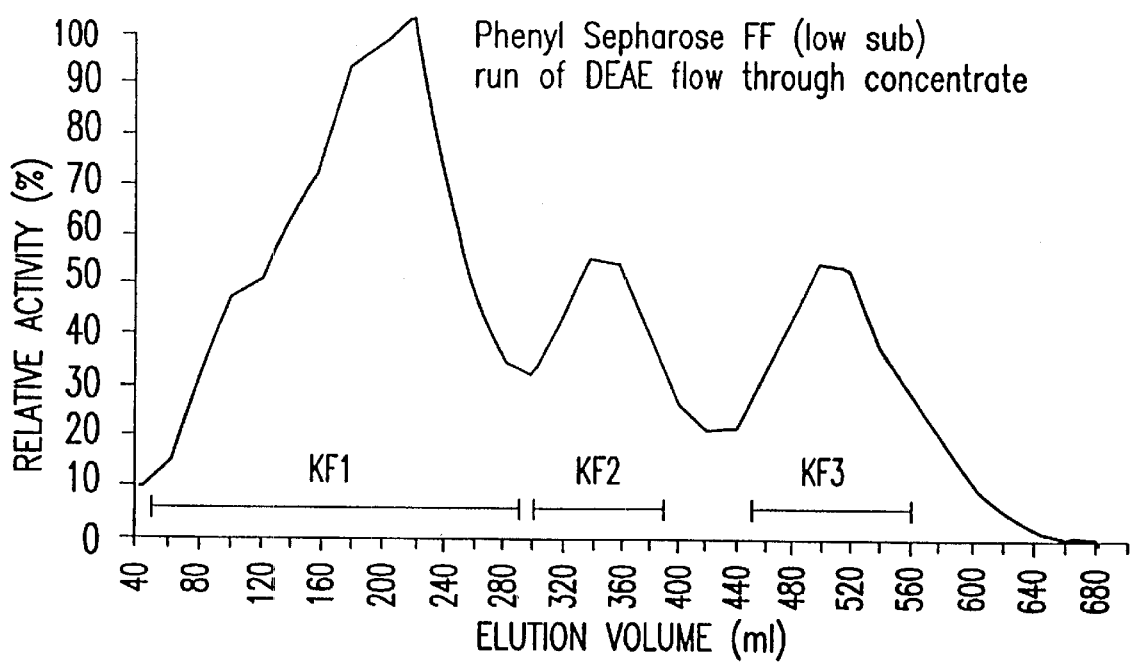

FIG. 6A shows the Phenyl Sepharose FF chromatography elution profile of DEAE flow through concentrate. The tubes that were combined to provide sample KF1, KF2 and KF3 are indicated.

Figure 7:
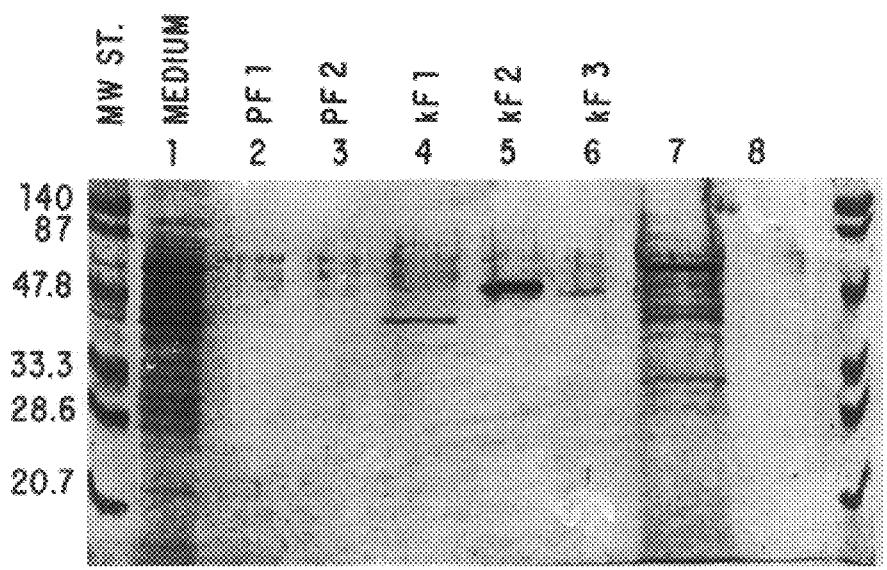

FIG. 7 shows the Coomassie Blue protein staining pattern of the various chromatographic pools. Abbreviations are as in FIGS. 6 and 6A. Leftmost and rightmost lanes: molecular weight markers; lane 1: medium; lane 2: PF1; lane 3: PF2; lane 4: KF1; lane 5: KF2; lane 6: KF3.

Figure 7A:
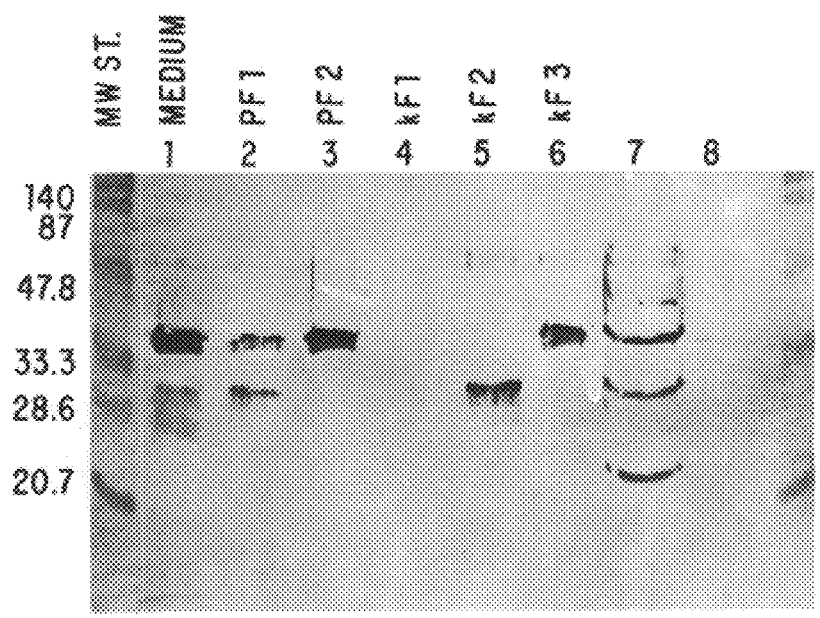

FIG. 7A shows the Western blot analysis of the various chromatographic pools stained for protein in FIG. 7. Polyclonal antiserum raised against the *T. fusca* TfxA xylanase was used for detection. Abbreviations are as in FIGS. 6 and 6A. Leftmost and rightmost lanes: molecular weight markers; lane 1: medium; lane 2: PF1; lane 3: PF2; lane 4: KF1; lane 5: KF2; lane 6: KF3.

Figure 8:
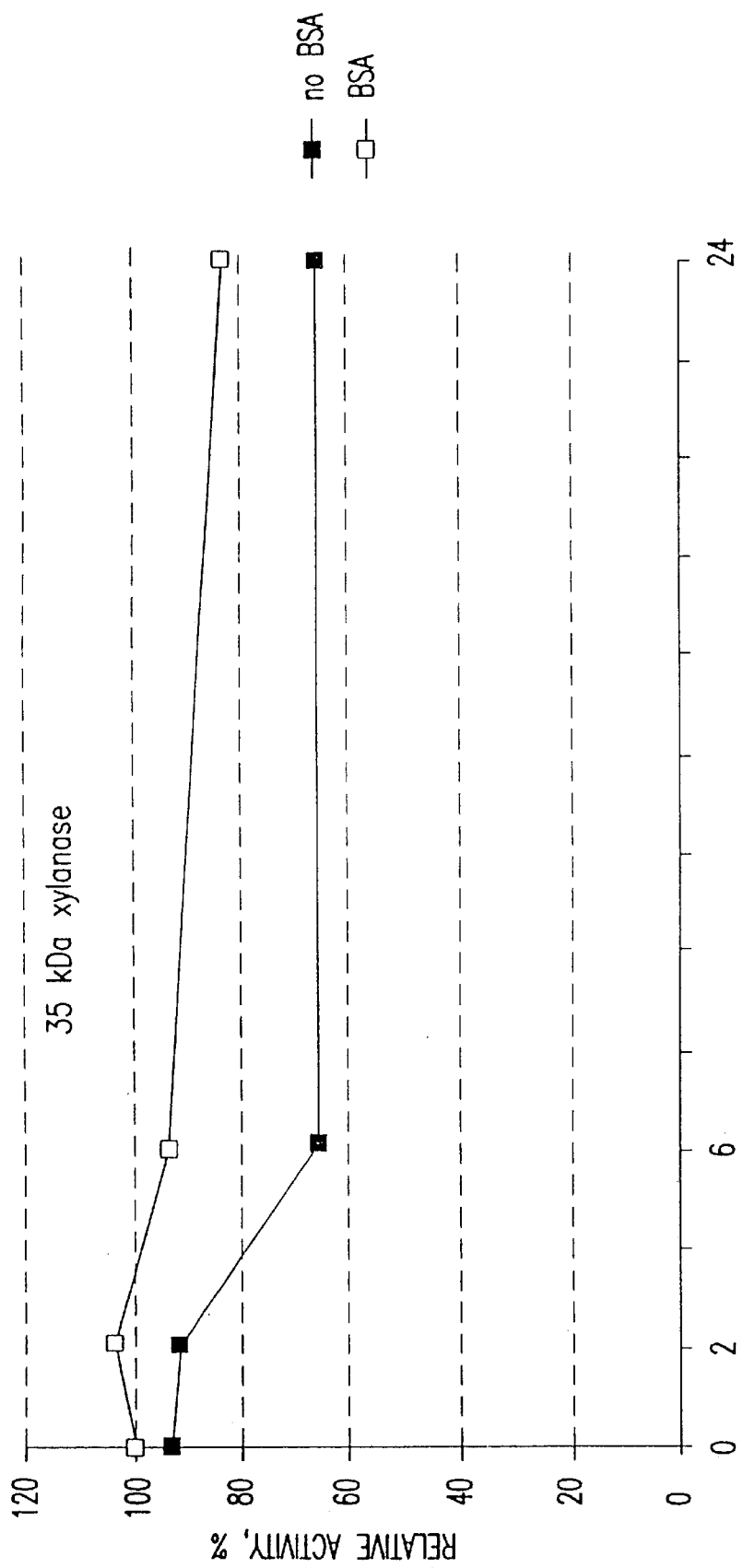

FIG. 8 shows the effect of BSA on the thermostability of the 35 kDa xylanase. Closed squares: no BSA; open squares: with BSA.

Figure 9:
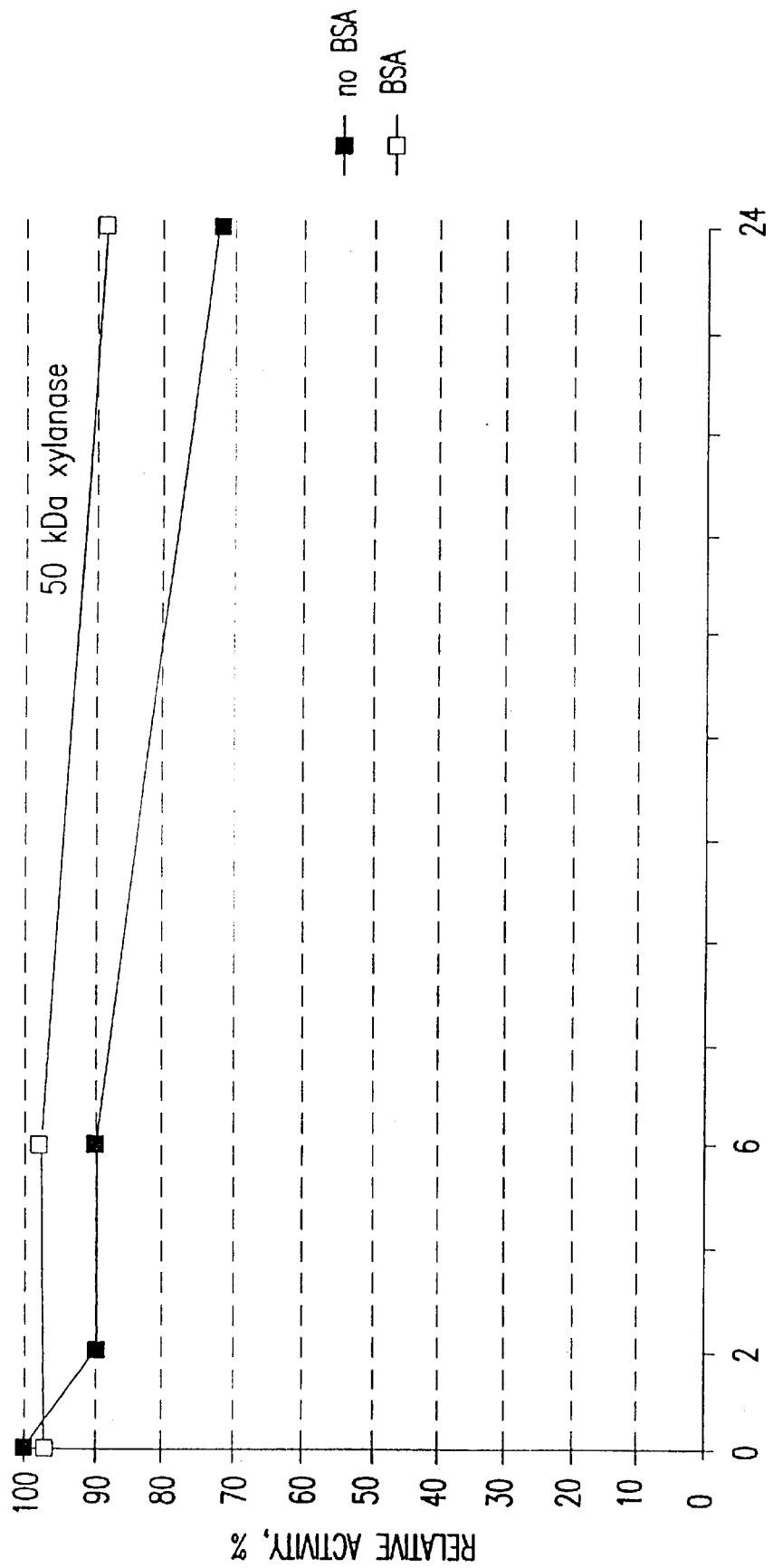

FIG. 9 shows the effect of BSA on the thermostability of the 50 kDa xylanase. Closed squares: no BSA; open squares: with BSA.

Figure 10:
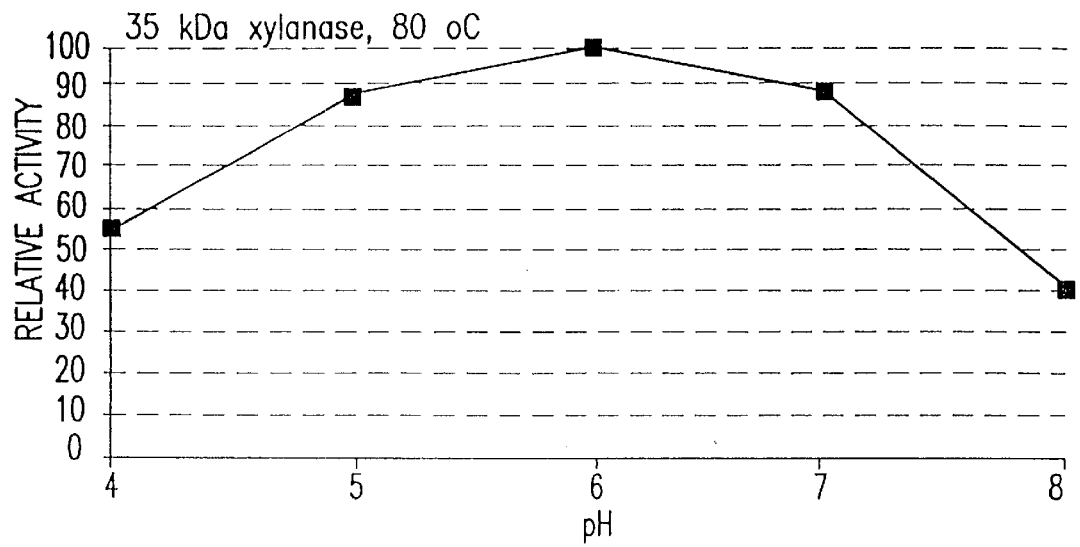
Figure 10A:
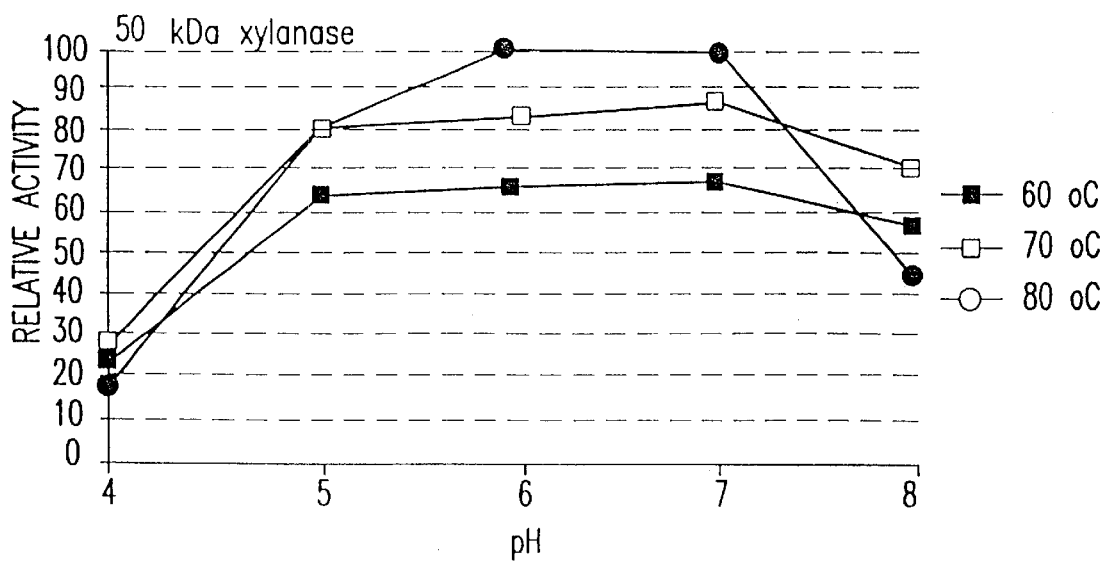

FIG. 10 consists of FIGS. 10A–10B.

FIG. 10 shows the effect of pH on the activity of the 35 kDa xylanase at 80° C.

FIG. 10A shows the effect of pH on the activity of the 50 kDa xylanase at 60° C. (closed squares), 70° C. (open squares) and 80° C. (closed circles).

FIG. 10B shows the effect of pH on the activity of the 35 kDa (closed squares) and the 50 kDa (open squares) xylanases at 60° C. with 60 minute incubations.

Figure 11:
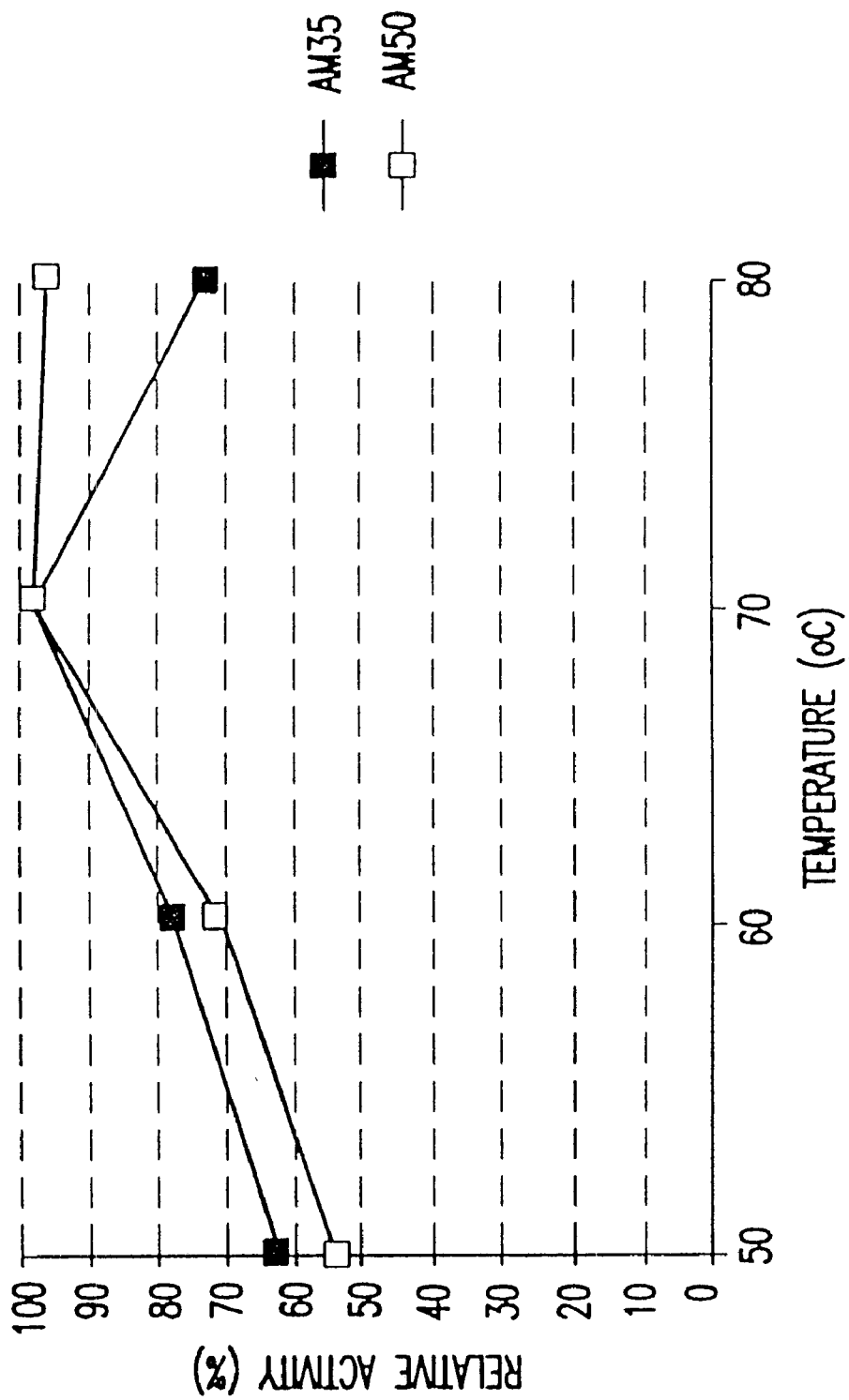

FIG. 11 shows the effect of temperature on the activity of the 35 kDa (closed squares) and the 50 kDa (open squares) at pH 7 with 60 minute incubations.

Figure 12:
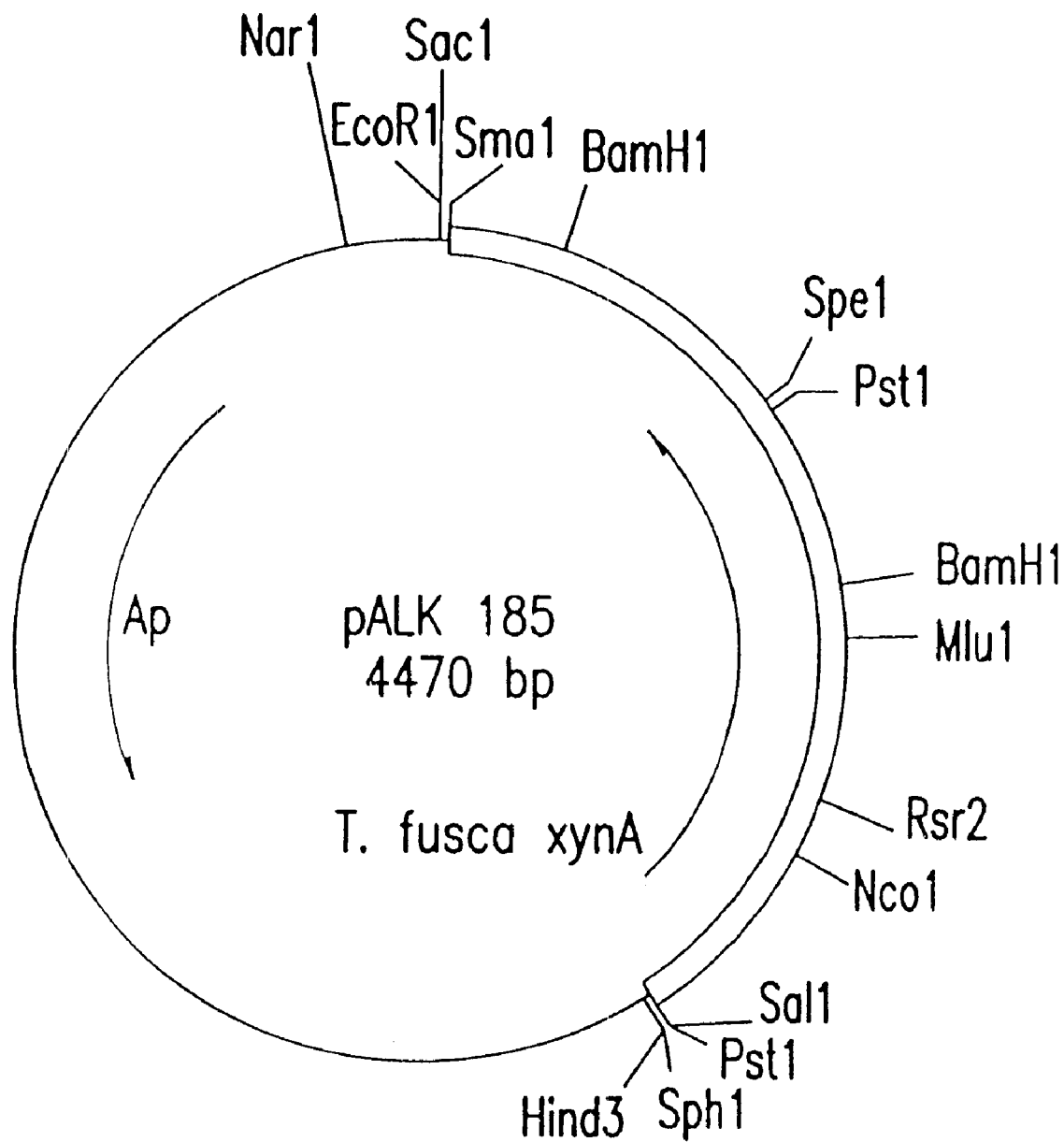

FIG. 12 is map of plasmid pALK185 (4470 bp).

FIGS. 13 and 13A show the DNA sequence (SEQ ID NO:1) and the amino acid sequence (SEQ ID NO:2) of 1375 bps of Actinomadura sp. DSM43186 35 kDa xylanase.

FIGS. 14–14B shows the DNA sequence (SEQ ID NO:3) and amino acid sequence (SEQ ID NO:4) of 1864 bps of Actinomadura sp. DSM43186 50 kDa xylanase.

FIGS. 15 and 15A show a homology comparison at the amino acid level between the AM50-peptide (SEQ ID NO:5) derived from the 1864 bps insert and the Actinomadura sp. FC7 xylanase II (accession no. U08894) gene (SEQ ID NO:6) The figure shows there was 70.7% identity in a 434 amino acid overlap.

FIGS. 15B and 15C show a homology comparison at the amino acid level between the AM50-peptide (SEQ ID NO:7) derived from the 1864 bps insert and the *Streptomyces lividans* xylanase A (xlna) gene (accession no. M64551) (SEQ ID NO: 8) The figure shows there was 70.3% identity in a 489 amino acid overlap.

Figure 16:
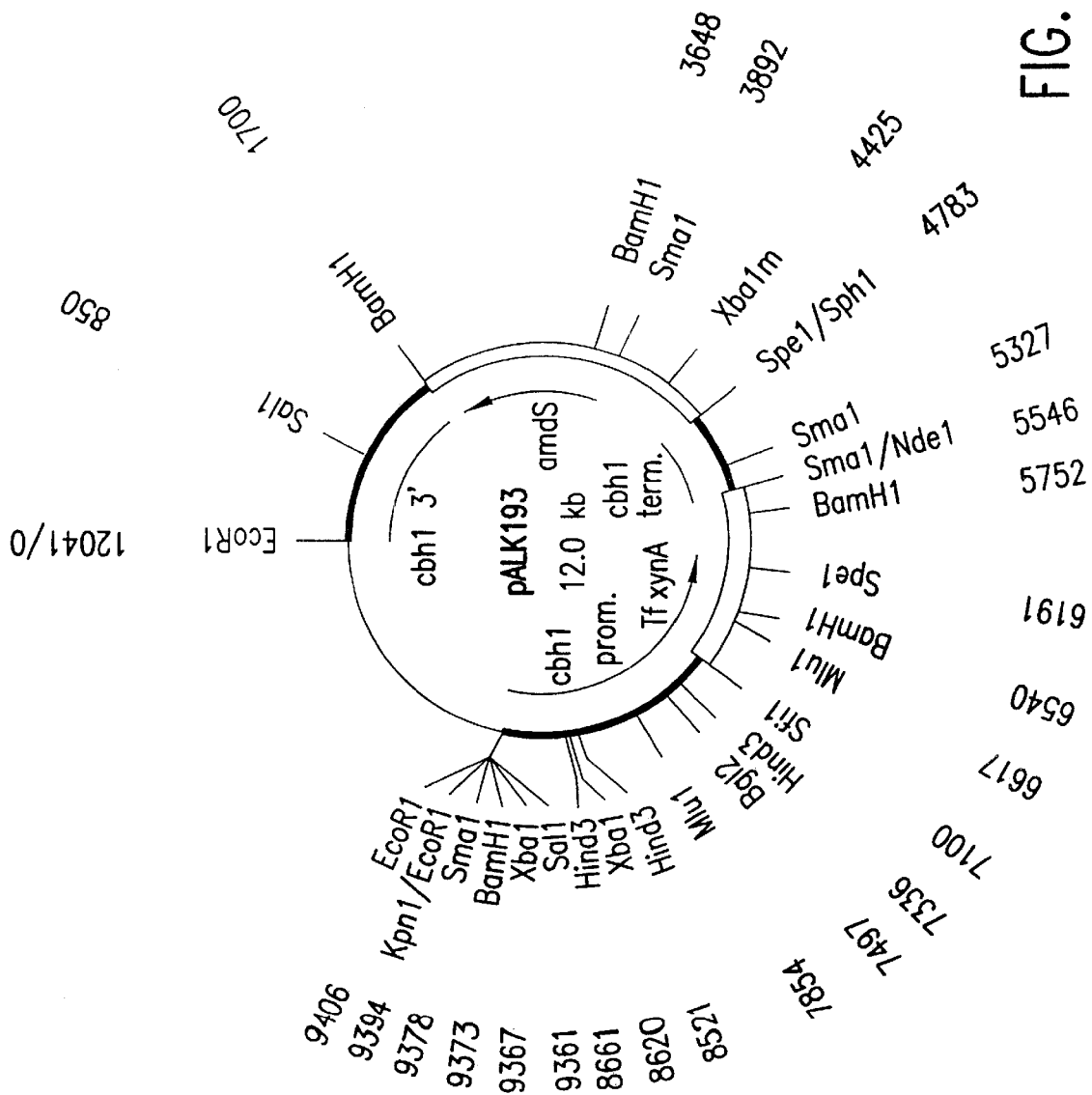

FIG. 16 shows the expression cassette pALK193 constructed for the *T. fusca* xylanase gene, xynA expression in *T reesei*.

Figure 17:
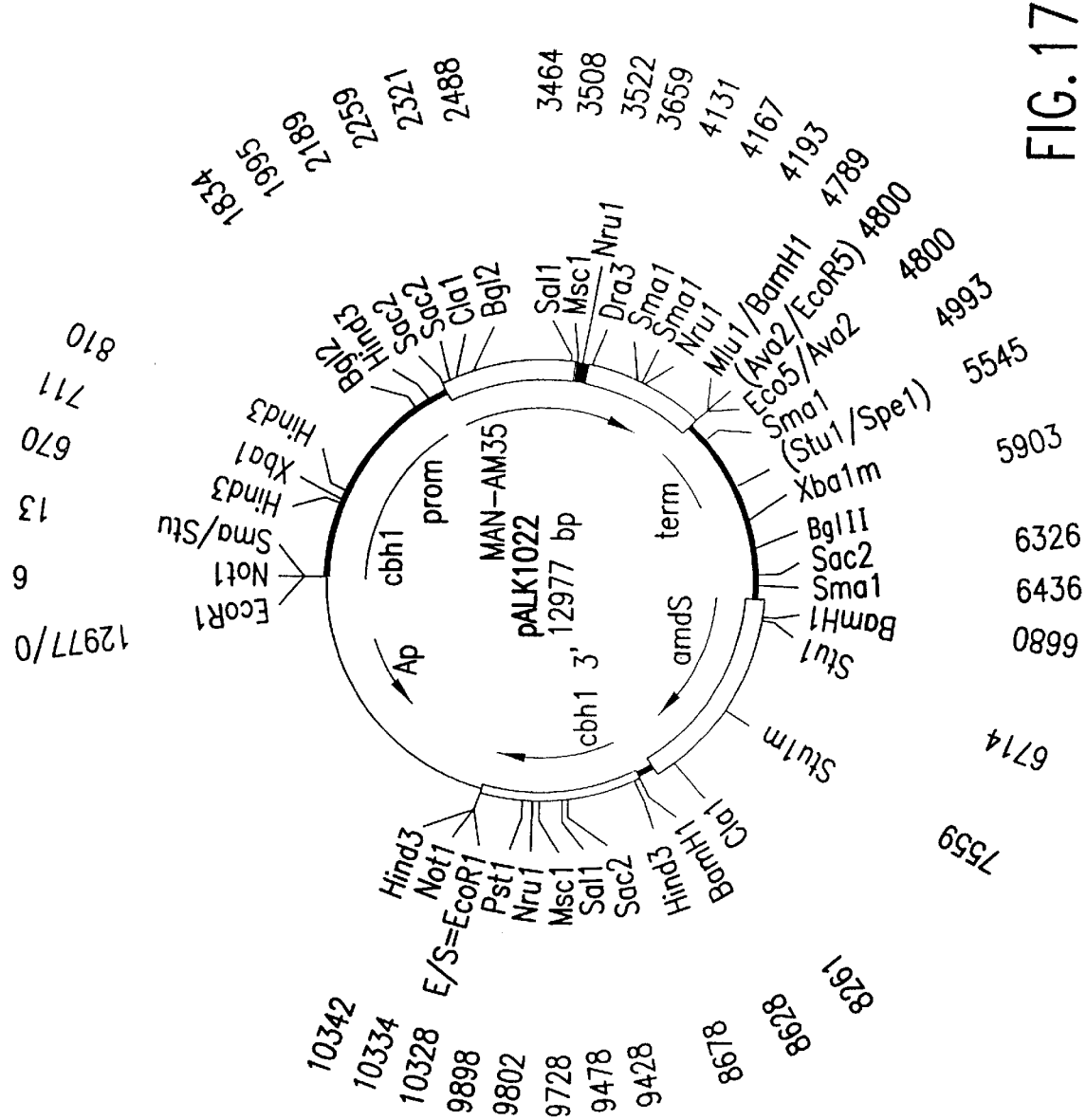

FIG. 17 is a map of plasmid pALK 1022 (12977 bp).

Figure 18:
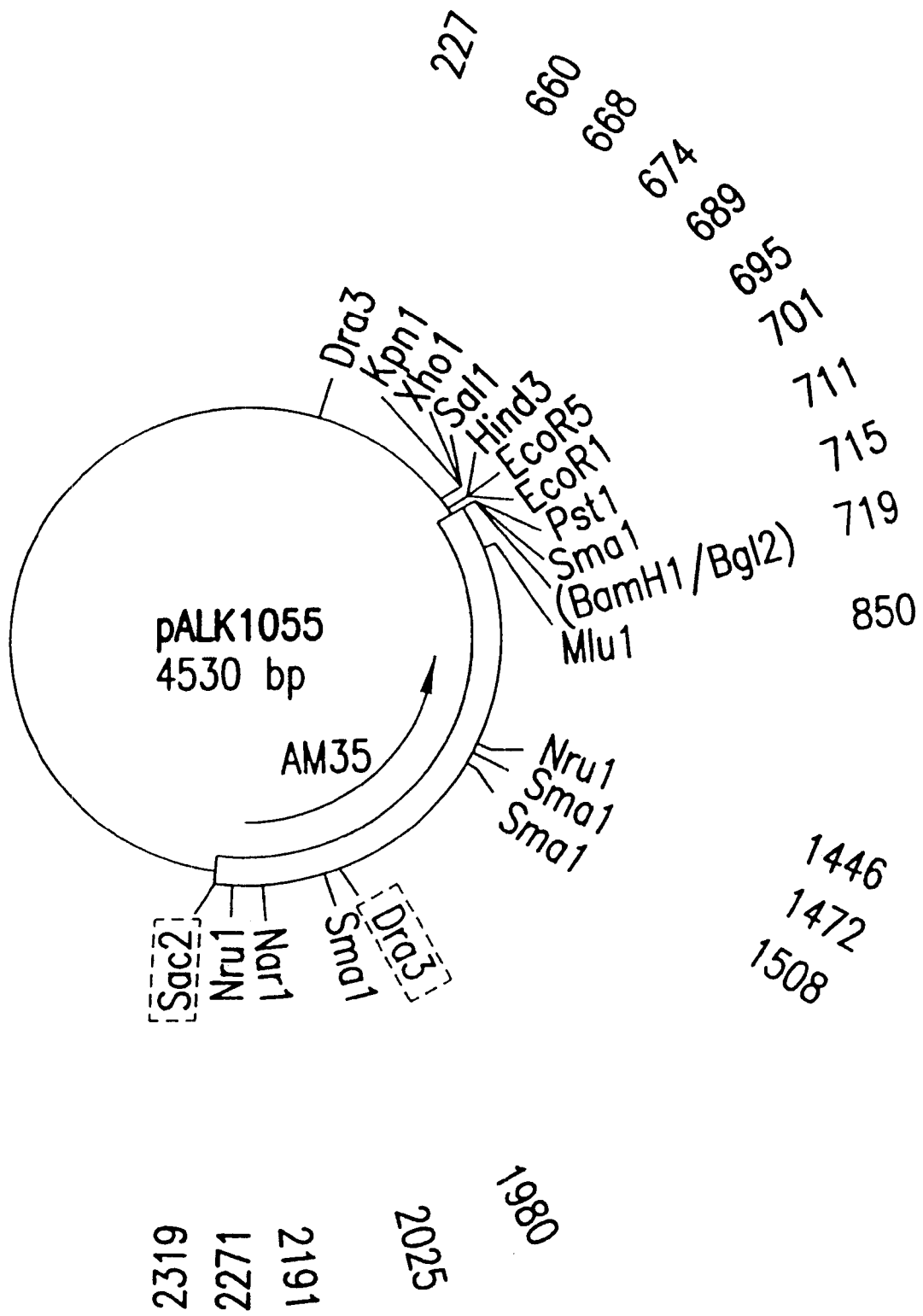

FIG. 18 is a map of plasmid pALK 1055(4355 bp).

FIG. 19 shows the DNA and amino acid sequences of the fusions between the manl core/hinge and the AM35 gene for pALK945 (SEQ ID NOS:9–10) pALK948, (SEQ ID NOS:11–12) pALK1021 (SEQ ID NOS:13–14) and pALK1022 (SEQ ID NOS:15–16).

Figure 20:
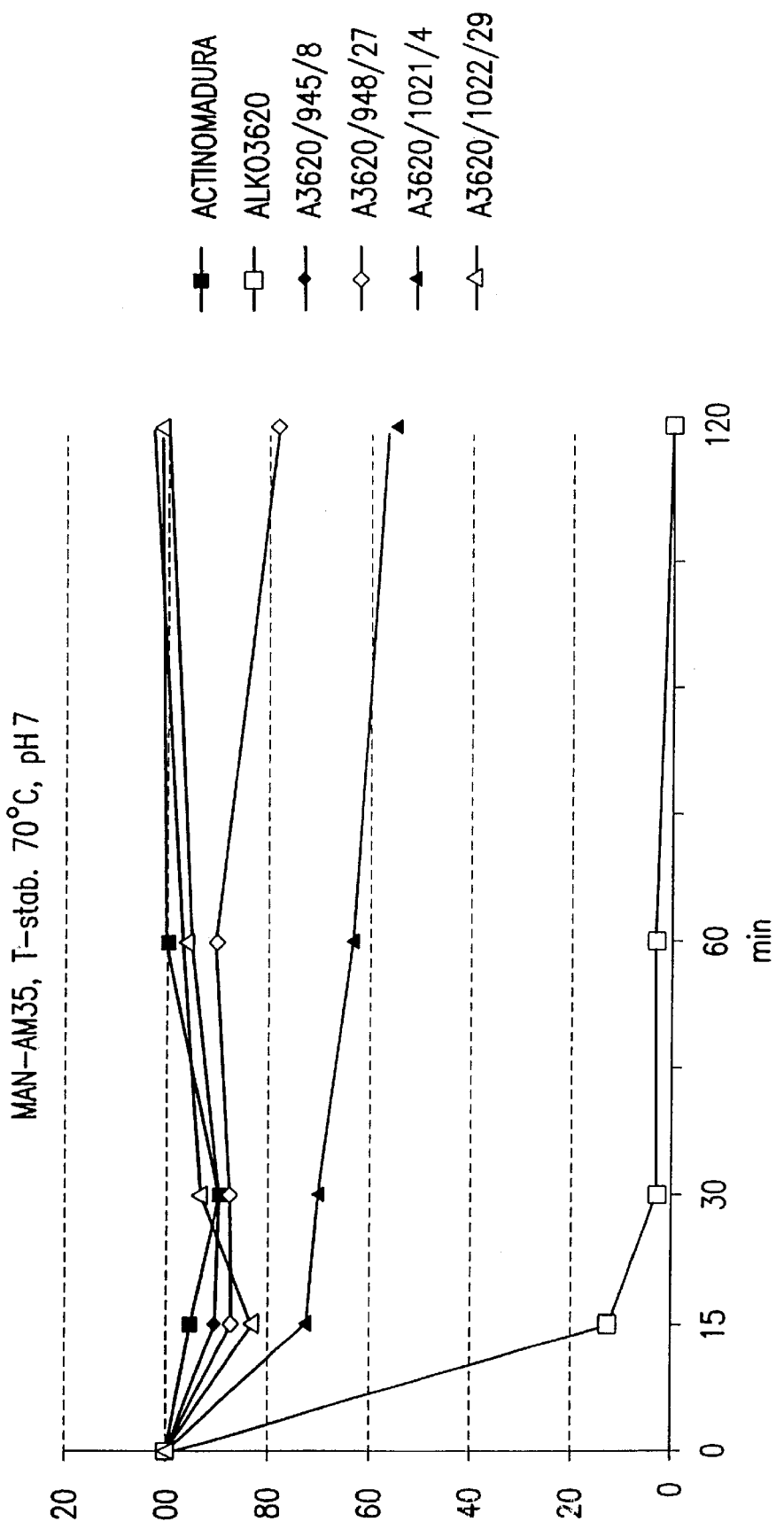

FIG. 20 shows the thermal stability of xylanase activity from culture supernatants of transformants producing Actinomadura 35 kDa xylanase.

Figure 21:
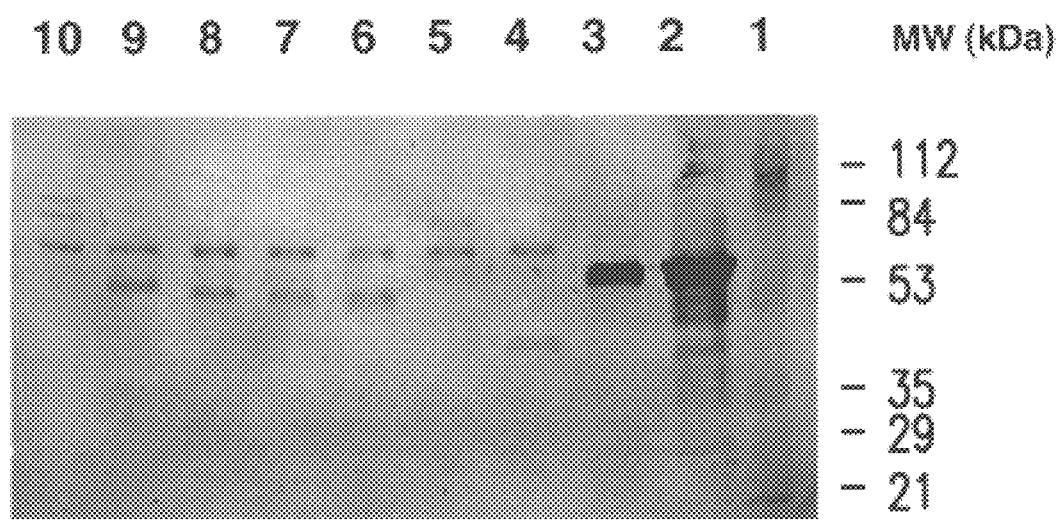

FIG. 21 shows a Western blot analysis of culture supernatants from transformants producing *Actinomadura xylanase*. The molecular weight of the β-mannanase protein in the culture medium of the host strain ALKO3620 (lanes 4 and 5) and of all the transformants (lanes 6–10) is somewhat larger than that of the purified 53 kDa β-mannanase protein sample lanes 2 and 3. In addition to the native β-mannanase, the transformants ALKO3620/pALK945/8, ALKO3620/pALK948/27 and ALKO3620/pALK1022/29 (lanes 6–9) produce a smaller protein (about 50 kDa) that reacted with the polyclonal mannanase antibody. This band represents the shortened mannanase protein obtained from the fusion constructs, and shows that the extracellular proteases have processed the fusion. In the strain ALKO3620/pALK1021/4 (lane 10) two bands with molecular weights of about 60 and 70 kDa are obtained. These bands originate from the unprocessed fusion protein (mannanase+*Actinomadura xylanase*.)

DEPOSITS

Plasmid pALK923, pALK938, pALK939, pALK940, pALK941 and pALK1056 were deposited at the Deutsche Sammlung von Mikroorganismen und Zellkulturen GmbH, Mascheroder Weg 1 b, D-38124 Braunschweig, Germany assigned accession numbers DSM 9322, DSM 9899, DSM 9900, DSM 9901, DSM 9902 and DSM 9903, respectively. pALK 923 was deposited on Jul. 29, 1994, and pALK 938–941 and pALK1056 were deposited on Apr. 3, 1995.

Plasmids pALK927 and pALK928 (that gave a positive signal with the *S. lividans* xlnA oligomer probe and contained the gene for the 50 kDa *Actinomadura xylanase*) were deposited at the DSM on Sep. 27, 1994, and assigned accession numbers DSM 9447 and DSM 9448, respectively.

DETAILED DESCRIPTION OF THE PREFERRED EMBODIMENTS

I. Definitions

In the description that follows, a number of terms used in recombinant DNA technology are extensively utilized. In order to provide a clearer and consistent understanding of the specification and claims, including the scope to be given such terms, the following definitions are provided.

Xylanase. As used herein, a xylanase is a hemicellulase that cuts the β-1,4 bonds within the xylosic chain of xylan, (xylan is a polymer of D-xylose residues that are joined through β-1,4 linkages). Xylanase activity is synonymous with xylanolytic activity.

By an amino acid sequence that is an "equivalent" of a specific amino acid sequence is meant an amino acid sequence that is not identical to the specific amino acid sequence, but rather contains at least some amino acid changes (deletion, substitutions, inversions, insertions, etc) that do not essentially affect the biological activity of the protein as compared to a similar activity of the specific amino acid sequence, when used for a desired purpose. Preferably, an "equivalent" amino acid sequence contains at least 85%–99% homology at the amino acid level to the specific amino acid sequence, most preferably at least 90% and in an especially highly preferable embodiment, at least 95% homology, at the amino acid level.

By the "biological" activity of a xylanase amino acid sequence of the invention is meant the enzymatic, functional (such as, for example, the secretion signal, or sequence of a specific domain) or the immunological activity of such amino acid sequence.

By a host that is "substantially incapable" of synthesizing one or more enzymes is meant a host in which the activity of one or more of the listed enzymes is depressed, deficient, or absent when compared to the wild-type.

Enzyme preparation. By "enzyme preparation" is meant a composition containing enzymes that have been extracted from (either partially or completely purified from) a microbe or the medium used to grow such microbe. "Extracted from" means any method by which the desired enzymes are separated from the cellular mass and includes breaking cells and also simply removing the culture medium from spent cells. Therefore, the term "enzyme preparation" includes compositions comprising medium previously used to culture a desired microbe(s) and any enzymes which the microbe(s) has secreted into such medium during the culture.

Enzyme-aided bleaching. By "enzyme-aided bleaching" is meant the extraction of lignin from cellulose pulp after the action of hemicellulose degrading enzymes with or without lignin degrading enzymes. Removal of the lignin may be restricted by hemicelluloses either physically (through reprecipitation onto the fiber surface during cooking) or chemically (through lignin-carbohydrate complexes). The hemicellulase activity partially degrades the hemicellulose, which enhances the extractability of lignins by conventional bleaching chemicals (like chlorine, chlorine dioxide, peroxide, etc.) (Viikari et al., "Bleaching with Enzymes" in *Biotechnology in the Pulp and Paper Industry*, Proc. 3rd Int. Conf., Stockholm, pp. 67–69 (1986); Viikari et al., "Applications of Enzymes in Bleaching" in *Proc. 4th Int. Symp. Wood and Pulping Chemistry*, Paris, Vol. 1, pp. 151–154 (1987); Kantelinen et al., "Hemicellulases and their Potential Role in Bleaching" in *International Pulp Bleaching Conference, Tappi Proceedings*, pp. 1–9 (1988)). The advantage of this improved bleachability is a lower consumption of bleaching chemicals and lower environmental loads or higher final brightness values. In the past, this has often been referred to as biobleaching.

Homologous. By an enzyme "homologous" to a host of the invention is meant that an untransformed strain of the same species as the host species naturally produces some amount of the native protein; by a gene "homologous" to a host of the invention is meant a gene found in the genome of an untransformed strain of the same species as the host species. By an enzyme "heterologous" to a host of the invention is meant that an untransformed strain of the same species as the host species does not naturally produce some amount of the native protein; by a gene "heterologous" to a host of the invention is meant a gene not found in the genome of an untransformed strain of the same species as the host species.

Cloning vehicle. A plasmid or phage DNA or other DNA sequence (such as a linear DNA) which provides an appropriate nucleic acid environment for the transfer of a gene of interest into a host cell. The cloning vehicles of the invention may be designed to replicate autonomously in prokaryotic and eukaryotic hosts. In fungal hosts such as Trichoderma, the cloning vehicles generally do not autonomously replicate and instead, merely provide a vehicle for the transport of the gene of interest into the Trichoderma host for subsequent insertion into the Trichoderma genome. The cloning vehicle may be further characterized by one or a small number of endonuclease recognition sites at which such DNA sequences may be cut in a determinable fashion without loss of an essential biological function of the vehicle, and into which DNA may be spliced in order to bring about replication and cloning of such DNA. The cloning vehicle may further contain a marker suitable for use in the identification of cells transformed with the cloning vehicle. Markers, for example, are antibiotic resistance. Alternatively, such markers may be provided on a cloning vehicle which is separate from that supplying the gene of interest. The word "vector" is sometimes used for "cloning vehicle."

Expression vehicle. A vehicle or vector similar to a cloning vehicle but which is capable of expressing a gene of interest, after transformation into a desired host.

When a fungal host is used, the gene of interest is preferably provided to a fungal host as part of a cloning or expression vehicle that integrates into the fungal chromosome. Sequences which derive from the cloning vehicle or expression vehicle may also be integrated with the gene of interest during the integration process. For example, in *T. reesei*, the gene of interest can be directed to the cbhl locus.

The gene of interest may preferably be placed under the control of (i.e., operably linked to) certain control sequences such as promoter sequences provided by the vector (which integrate with the gene of interest). If desired, such control sequences may be provided by the host's chromosome as a result of the locus of insertion.

Expression control sequences on an expression vector will vary depending on whether the vector is designed to express a certain gene in a prokaryotic or eukaryotic host (for example, a shuttle vector may provide a gene for selection in bacterial hosts) and may additionally contain transcriptional elements such as, enhancer elements, termination sequences, and/or translational initiation and termination sites.

I. Identification and Isolation of *Actinomadura flexuosa* Xylanases

Two xylanases have been identified, purified and cloned from *Actinomadura flexuosa*. Both of these xylanases have a pH optimum and thermostability that are desirable for the enzyme-aided bleaching of wood pulp. One of these xylanases has a molecular weight of about 35 kDa (AM35) and the other has a molecular weight of about 50 kDa (AM50).

The optimal temperature range for *Actinomadura flexuosa* xylanases in crude preparations is 70–80° C. at pH 6–7. At pH 8, the optimum temperature range of this xylanase preparation is 60–70° C. This is useful in kraft pulp bleaching because after kraft cooking, the pH of the pulp is alkaline.

In purified preparations, AM35 retains 80% of its activity, and AM50 retains 90% of its activity after 24 hours when incubated in the presence of BSA. At 80° C., both AM35 and AM50 are most active at pH 6 but both exhibit a broad activity plateau between pH 5–pH 7, wherein about 80% of the activity is retained.

For the isolation of AM35 and AM50, the host *Actinomadura flexuosa* is available as depository accession number DSM43186 from Deutsche Sammlung von Mikroorganismen und Zellkulturen GmbH, Mascheroder Weg 1b, D-38124 Braunschweig, Germany. Both forms can be purified by passage through a series of chromatographic columns. A first purification step by DEAE Sepharose CL-4B retains about half of the xylanase activity when the sample is applied at pH 8.6–9 in 12.5 mM $Na_2HPO_4$; the other half is found in the flow through.

Elution of the bound xylanase activity with a salt gradient results in an elution of a sharp, earlier eluting peak of activity and a broad, later eluting peak of activity. The sharp, earlier eluting peak retains its homogeneity when subjected to phenyl Sepharose CL-4B chromatography. Samples taken from the later, broad peak of activity separate into at least two peaks when subjected to Phenyl Sepharose CL-4B chromatography. There is only weak cross-reactivity of these later eluting xylanases with a polyclonal antibody directed against *Thermomonospora fusca* xylanase.

By SDS-PAGE, the molecular weight of the xylanase in these pools from the DEAE retentate was about 50 kDa, while the molecular weights of the xylanases in the DEAE flow through was 30, 35, 40 and 50 kDa. Thus, *Actinomadura flexuosa* contains three to four xylanase protein bands.

II Xylanase Enzyme-Aided Bleaching Using the *Actinomadura flexuosa* Xylanases

The present invention comprehends a method for chemically treating plant biomass under conditions of high temperature of 50–80° C. and pH 5–8, and especially 60° C.–80° C., pH 6–7 and most preferably 70° C. and pH 7.0 for one hour. In a preferred embodiment, plant biomass is bleached with xylanases that are able to hydrolyze xylan chains in wood pulp at neutral or moderately alkaline pH and high temperature (60° C.).

Wood pulp is a composite material consisting primarily of a matrix of cellulose, hemicellulose, and lignin. A common procedure for wood pulp production is chemical pulping. One typical mode of chemical pulping is alkaline sulphate cooking, so called kraft cooking. Under the process conditions (high temperatures and high alkalinity), the cooking chemicals extract the lignin out of the pulp. However, not all of the lignin is removed during cooking, but part of it, (about 5%), remains in the pulp. This residual lignin has to be removed in order to get pulp suitable for paper production.

Many processes have been developed for the removal of lignin. Typically, the wood pulp is treated with chlorine or other toxic chemicals in order to remove the lignin component and provide a bleached pulp. However, the toxic by-products of this chemical treatment have a negative impact upon the health and stability of the environment into which they are released. Consequently, there is a great need for developing alternative, more environmentally protective techniques to achieve pulp bleaching. Treatment of the cooked pulp with enzymes that degrade the hemicellulose component, e.g., xylan, in the pulp, modifies the pulp so that the lignin becomes easier to remove. This leads to improved bleachability which in turn gives the advantages of lower bleaching chemical consumption and lower environmental loads and/or higher final brightness.

Under the method of the present invention, an enzyme-aided beaching technique is developed whereby thermostable and neutral xylanases can be used in such conditions that the need to adjust the pH and temperature after the cooking step is decreased or eliminated. The processing conditions of the invention may additionally act to reduce cellulase activity in the enzyme preparation or culture medium.

In a preferred embodiment, the process. of the invention is carried out in vitro in wood pulp. The process involves placing the enzyme preparation, culture medium, or concentrated mixture containing xylanase into contact with the wood pulp. Routine calculations enable those in the art to determine the optimum treatment time depending upon the result desired, the concentration and specific activity of the xylanase enzyme used, the type and concentration of pulp used, pH and temperature of the acidic liquor, and other parameter variables.

The method of the present invention may be applied alone or as a supplement to other treatments that reduce the lignin content of wood pulp, increase its drainability and/or decrease its water retention. In a preferred embodiment, the present invention is used to enhance brightness properties of the wood pulp by treatment of chemical pulps, i.e., those pulps containing lignin that has been chemically modified through chemical treatment.

In a preferred embodiment, the xylanases used in the methods of the invention are preferably those of *Actinomadura flexuosa*, and especially the 35 kDa and/or 50 kDa xylanases of *Actinomadura flexuosa*. Especially, culture medium that contains the enzymes secreted as a result of the growth of the cells are useful in the methods of the invention, as are the culture medium that can be provided by a recombinant host that has been transformed with the xylanase encoding genes of the invention.

III. Genetic Engineering of the Hosts of the Invention

The problem of producing bacterial proteins, preferably xylanases in a cost-effective manner in a large scale is solved by producing the proteins in filamentous fungi, e.g. Aspergillis or Trichoderma. The process for efficiently producing bacterial proteins in filamentous fungi is facilitated through the cloning of genetic sequences that encode the desired bacterial protein activity and through the expression of such genetic sequences in filamentous fungi. As used herein, the term "genetic sequences" is intended to refer to a nucleic acid molecule (preferably DNA). Genetic sequences that encode the desired proteins are derived from a variety of bacterial sources. These sources include actinomycetous DNA, cDNA, synthetic DNA and combinations thereof, preferably actinomycetous DNA, cDNA, synthetic DNA and combinations thereof encoding xylanase, most preferably Actinomadura genomic DNA, cDNA, synthetic DNA and combinations thereof. Vector systems may be used to produce hosts for the production of the enzyme preparations of the invention. Such vector construction (a) may further provide a separate vector construction (b) which encodes at least one desired gene to be integrated to the genome of the host and (c) a selectable marker coupled to (a) or (b). Alternatively, a separate vector may be used for the marker.

A nucleic acid molecule, such as DNA, is said to be "capable of expressing" a polypeptide if it contains expression control sequences which contain transcriptional regulatory information and such sequences are "operably linked" to the nucleotide sequence which encodes the polypeptide.

An operable linkage is a linkage in which a sequence is connected to a regulatory sequence (or sequences) in such a way as to place expression of the sequence under the influence or control of the regulatory sequence. Two DNA sequences (such as a protein encoding sequence and a promoter region sequence linked to the 5' end of the encoding sequence) are said to be operably linked if induction of promoter function results in the transcription of the protein encoding sequence mRNA and if the nature of the linkage between the two DNA sequences does not (1) result in the introduction of a frame-shift mutation, (2) interfere with the ability of the expression regulatory sequences to direct the expression of the mRNA, antisense RNA, or protein, or (3) in-terfere with the ability of the template to be transcribed by the promoter region sequence. Thus, a promoter region would be operably linked to a DNA sequence if the promoter were capable of effecting transcription of that DNA sequence.

The precise nature of the regulatory regions needed for gene expression may vary between species or cell types, but shall in general include, as necessary, 5' non-transcribing and 5' non-translating (non-coding) sequences involved with initiation of transcription and translation respectively. Expression of the protein in the transformed hosts requires the use of regulatory regions functional in such hosts. A wide variety of transcriptional and translational regulatory sequences can be employed. In eukaryotes, where transcription is not linked to translation, such control regions may or may not provide an initiator methionine (AUG) codon, depending on whether the cloned sequence contains such a methionine. Such regions will, in general, include a promoter region sufficient to direct the initiation of RNA synthesis in the host cell.

As is widely known, translation of eukaryotic mRNA is initiated at the codon which encodes the first methionine. For this reason, it is preferable to ensure that the linkage between a eukaryotic promoter and a DNA sequence which encodes the protein, or a functional derivative thereof, does not contain any intervening codons which are capable of encoding a methionine. The presence of such codons results either in a formation of a fusion protein (if the AUG codon is in the same reading frame as the protein encoding DNA sequence) or a frame-shift mutation (if the AUG codon is not in the same reading frame as the protein encoding sequence).

In a preferred embodiment, a desired protein is secreted into the surrounding medium due to the presence of a secretion signal sequence. If a desired protein does not possess its own signal sequence, or if such signal sequence does not function well in the host, then the protein's coding sequence may be operably linked to a signal sequence homologous or heterologous to the host. The desired coding sequence may be linked to any signal sequence which will allow secretion of the protein from the host. Such signal sequences may be designed with or without specific protease sites such that the signal peptide sequence is amenable to subsequent removal. Alternatively, a host that leaks the protein into the medium may be used, for example a host with a mutation in its membrane.

If desired, the non-transcribed and/or non-translated regions 3' to the sequence coding for a protein can be obtained by the above-described cloning methods. The 3'-non-transcribed region may be retained for its transcriptional termination regulatory sequence elements; the 3-non-translated region may be retained for its translational termination regulatory sequence elements, or for those elements which direct polyadenylation in eukaryotic cells.

The vectors of the invention may further comprise other operably linked regulatory elements such as enhancer sequences.

In a preferred embodiment, genetically stable transformants are constructed whereby a desired protein's DNA is integrated into the host chromosome. The coding sequence for the desired protein may be from any source. Such integration may occur de novo within the cell or, in a most preferred embodiment, be assisted by transformation with a vector which functionally inserts itself into the host chromosome, for example, DNA elements which promote integration of DNA sequences in chromosomes.

Cells that have stably integrated the introduced DNA into their chromosomes are selected by also introducing one or more markers which allow for selection of host cells which contain the expression vector in the chromosome, for example the marker may provide biocide resistance, e.g., resistance to antibiotics, or heavy metals, such as copper, or the like. The selectable marker gene can either be directly linked to the DNA gene sequences to be expressed, or introduced into the same cell by co-transfection.

Factors of importance in selecting a particular plasmid or viral vector include: the ease with which recipient cells that contain the vector may be recognized and selected from those recipient cells which do not contain the vector; the number of copies of the vector which are desired in a particular host; and whether it is desirable to be able to "shuttle" the vector between host cells of different species.

Once the vector or DNA sequence containing the construct(s) is prepared for expression, the DNA construct(s) is introduced into an appropriate host cell by any of a variety of suitable means, including transformation as described above. After the introduction of the vector, recipient cells are grown in a selective medium, which selects for the growth of transformed cells. Expression of the cloned gene sequence(s) results in the production of the desired protein, or in the production of a fragment of this protein. This expression can take place in a continuous manner in the transformed cells, or in a controlled manner.

Accordingly, the bacterial protein encoding sequences may be operably linked to any desired vector and transformed into a selected filamentous fungi host, preferably Trichoderma host, so as to provide for expression of such proteins in that host.

To facilitate secretion of the bacterial protein, the bacterial encoding sequences may be fused in frame to other sequences so as to construct DNA encoding a fusion protein. For example, a recombinant vector encoding a xylanase gene from bacterial origin is fused with the sequence of a Trichoderma cellulase or hemicellulase, or at least one functional domain (i.e. that part of the core which contains signals or sequences that permit the proteins or fusion constructions to be secreted) of said cellulase or hemicellulase as described in U.S. Pat. No. 5,298,405, WO 93/24622 and in GenBank submission L25310, each incorporated herein by reference. Especially, the enzyme is selected from the group consisting of CBHI, CBHII, EGI, EGII XYLI, XYLII and mannanase (MANI), or a domain thereof, such as the secretion signal or the core sequence. Mannanase has the same domain structure as that of the cellulases: a core domain, containing the active site, a hinge domain containing a serine-threonine rich region, and a tail, containing the binding domain.

If a xylanase gene of bacterial origin is fused in frame to an Aspergillus sequence, the sequence is selected from the group consisting of secretable proteins like *A. niger* or *A. niger* var *awamori* glucoamylases or *A. oryzae* proteases or at least one functional domain of said secretable proteins.

Fusion peptides can be constructed that contain an N-terminal mannanase or cellobiohydrolase or endoglucanase core domain or the core and the hinge domains from the same, fused to the Actinomadura xylanase sequence. The result is a protein that contains N-terminal mannanase or cellobiohydrolase or endoglucanase core or core and hinge regions, and a C-terminal Actinomadura xylanase. The fusion protein contains both the mannanase or cellobiohydrolase or endoglucanase and xylanase activities of the various domains as provided in the fusion construct. A further alternative is to use a gene coding for an inactive mannanase or cellobiohydrolase or endoglucanse core domain or the core and hinge domains from the same, fused to Actinomadura xylanase sequences. The resulting fusion protein then contains the inactive enzyme domain fused to a desired bacterial sequence.

It should be noted, however, that the whole core region may not be necessary to obtain secretion of the desired fusion protein . A shorter fragment of this domain may also be used, particularly a fragment of the domain containing secretory signals for the protein of interest. Such a fragment should be longer than the signal sequence, but may still be shorter than the whole core region.

Fusion proteins can also be constructed such that the mannanase or cellobiohydrolase or endogluanase tail or a desired fragment thereof, is included, placed before the Actinomadura xylanase sequence, especially so as to allow use of a nonspecific protease site in the tail as a protease site for the recovery of the xylanase sequence from the expressed fusion protein. Alternatively, fusion proteins can be constructed that provide for a protease site in a linker that is placed before the Actinomadura xylanase, with or without tail sequences.

Accordingly, this invention results in the production and secretion of bacterial proteins in filamentous fungi. The bacterial protein is encoded as a fusion to a gene of a homologous secretable protein of the filamentous fungi, thereby resulting in a high level of expression and secretion. The improvement in secretion of bacterial proteins is tenfold compared to the production and secretion of bacterial proteins without a fusion of the bacterial protein encoding gene to a homologous fungal gene encoding a secreted protein. When a mammalian protein like chymosin is produced as a fusion protein in Aspergillus, the level of production has been only 10–20% of the production levels of this invention (WO 90/15860). Similarly, the production level of immunoglobulins in Trichoderma has been only 10–20% of the production levels of this invention (WO 92/01797).

IV. The Enzyme Preparations of the Invention

According to the invention, there is provided enzyme compositions useful in a method for enzyme-aided bleaching and pulp and paper processing. There is also provided a method for producing an enzyme preparation partially or completely deficient in cellulolytic activity (that is, in the ability to completely degrade cellulose to glucose) and enriched in xylanases desirable for pulp and paper processing. By "deficient in cellulolytic activity" is meant a reduced, lowered, depressed, or repressed capacity to degrade cellulose to glucose. Such cellulolytic activity deficient preparations, and the making of same by recombinant DNA methods, are described in U.S. Pat. No. 5,298,405, incorporated herein by reference. As described herein, xylanases may be provided directly by the hosts of the invention (the hosts themselves are placed in the wood processing medium). Alternatively, used medium from the growth of the hosts, or purified enzymes therefrom, can be used. Further, if desired activities are present in more than one recombinant host, such preparations may be isolated from the appropriate hosts and combined prior to use in the method of the invention.

The enzyme preparations of the invention satisfy the requirements of specific needs in various applications in the pulp and paper industry. For example, if the intended application is improvement of the strength of the mechanical mass of the pulp, then the enzyme preparations of the invention may provide enzymes that enhance or facilitate the ability of cellulose fibers to bind together. In a similar manner, in the application of pulp milling, the enzyme preparations of the invention may provide enzymes that enhance or facilitate such swelling.

To obtain the enzyme preparations of the invention, the native or recombinant hosts described above having the desired properties (that is, hosts capable of expressing large quantities of the desired xylanase enzymes and optionally, those which are substantially incapable of expressing one or more cellulase enzymes) are cultivated under suitable conditions, the desired enzymes are secreted from the hosts into the culture medium, and the enzyme preparation is recovered from said culture medium by methods known in the art.

The enzyme preparation can be produced by cultivating the recombinant host or native strain in a fermentor. For example, the enzyme preparation of the present invention can be produced in a liquid cultivation medium that contains oat spelt xylans as the main carbon source as described by Morosoli (*Biochem J.* 239:587–592 (1986)).

The enzyme preparation is the culture medium with or without the native or transformed host cells, or is recovered from the same by the application of methods well known in the art. However, because the xylanase enzymes are secreted into the culture media and display activity in the ambient conditions of the hemicellulolytic liquor, it is an advantage of the invention that the enzyme preparations of the invention may be utilized directly from the culture medium with no further purification. If desired, such preparations may be lyophilized or the enzymatic activity otherwise concentrated and/or stabilized for storage. The enzyme preparations of the invention are very economical to provide and use because (1) the enzymes may be used in a crude form; isolation of a specific enzyme from the culture fluid is unnecessary and (2) because the enzymes are secreted into the culture medium, only the culture medium need be recovered to obtain the desired enzyme preparation; there is no need to extract an enzyme from the hosts.

If desired, an expressed protein may be further purified in accordance with conventional conditions, such as extraction, precipitation, chromatography, affinity chromatography, electrophoresis, or the like.

The invention is described in more detail in the following examples, These examples show only a few concrete applications of the invention. It is self evident for one skilled in the art to create several similar applications. Hence the examples should not be interpreted to narrow the scope of the invention only to clarify the use of the invention.

EXAMPLES

Example 1

*Actinomadura flexuosa* DSM43186 Shake Flask and Fermentor Cultivations

The strain *Actinomadura flexuosa* DSM43186 was streaked on rolled oats mineral medium plate (Deutsche Sammlung von Mikroorganismen und Zellkulturen GmbH [German collection of microorganisms and cell cultures], *DSM Catalogue of strains*, 3rd ed., Braunschweig, Germany (1983)); 1 liter contains 20 g agar, 20 g rolled oats, 1 ml trace element solution containing 100 mg $FeSO_4 \times 7H_2O$, 100 mg $MnCl_2 \times 4H_2O$, 100 mg $ZnSO_4 \times 7H_2O$/100 ml; pH 9.0) and incubated at 50° C. until sporulating. A sporulating colony was inoculated in 10 ml of XPYB medium (Greiner-Mai, E. et al., *System. Appl. Microbiol.* 9:97–109 (1987); Holtz, C. et al., *Antonie van Leeuwenhoek* 59:1–7 (1991)); 1 liter contains 5 g oats spelt xylan, 5 g peptone from casein, 5 g yeast extract, 5 g beef extract, 0.74 g $CaCl_2 \times 2H_2O$; pH 9.0) and was incubated at 55° C. in a rotary shaker (250 rpm) for two to three days. An inoculum of 5 ml was then transferred to 250 ml of the same medium and incubated at the same conditions for three days. Xylanase activity obtained was 17 nkat/ml (measured at pH 6.0, 60° C., 5 min reaction; Bailey, M. J. et al., *J. Biotechnol* 23:257–270 (1992).

The procedure for two 1 l fermentations (Biostat M, B. Braun, Melsungen, Germany) was prepared as above. 10% (v/v) inoculum was used for the fermentations. The pH was maintained at pH 7.8±0.2 by addition of ammonia (12.5% (v/v)) and phosphoric acid (17% (v/v)), the fermentation temperature was 50° C. The fermentor was stirred at 400 rpm and the air flow was 1 l/min. The xylanase activities obtained were 32 and 58 nkat/ml (pH 6.0, 60° C., 5 min reaction; Bailey, M. J. et al., *J. Biotechnol* 23:257–270 (1992).

Example 2

Determination of the Optimal pH and Temperature of *Actinomadura flexuosa* Xylanase Activity from the Culture Supernatant Xylanase activities throughout the Examples were measured according to Bailey, M. J. et al., *J. Biotechnol* 23:257–270 (1992) using 1% (w/v) birch xylan (Roth 7500) as a substrate. The assay conditions are, if not otherwise stated, pH 5.3 and 50° C., with an incubation time of 5 min.

(Bailey, M. et al., *J. Biotechnol*. 23:257–270 (1992)). One xylanase unit (1 nkat) is defied as the amount of enzyme that produces reducing carbohydrates having a reducing power corresponding to one nmol of xylose in one second from birch xylan under assay conditions. Defining the International Unit as the amount of enzyme that produces one micromole of measured end-products in one minute from the polymeric substrate, then 1 IU=16.67 nkat.

To determine the optimal pH for the Actinomadura xylanase activity, samples from the shake flask cultivation (culture supernatant) were diluted in McIlvain's buffers (0.25 M citric acid–0.5 M $Na_2HPO_4$) of pH-range 3.0–11.0. The final pHs of the enzyme buffer mixtures were 3.5, 4.5, 5.4, 6.4, 7.2, 8.0, 8.5, 9.7 and 11.2. Xylanase activity was measured at each pH at 50° C., 5 min reaction. The xylanase activity exhibited 80–100% of its maximum activity in the pH range of about 5.4–8.0. The enzyme had its maximum activity at about pH 6.4 (FIG. 1).

Figure 2:
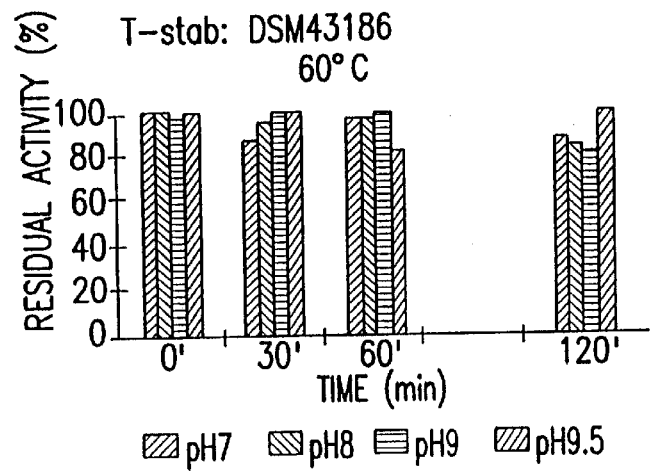
FIGS. 2, 2A and 2B show the effect of temperature on *A. flexuosa* (DSM43186) xylanase activity (culture supernatant). On each figure, the four bars at each time point represent pH 7, pH 8, pH 9 and pH 9.5, respectively from left to right.
Figure 2A:
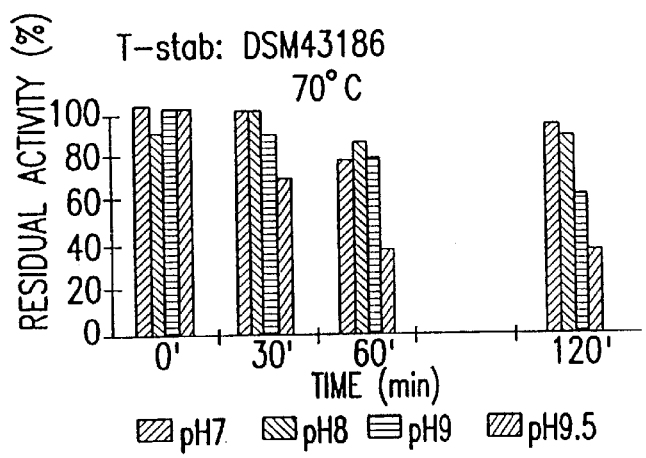
Figure 2B:
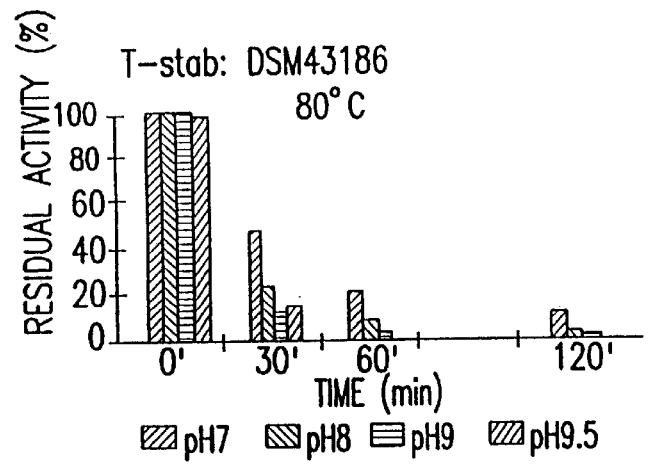

For the thermal stability determination, samples from the culture supernatant were diluted in McIlvain's buffers. BSA was added to a concentration of 100 μg/ml and pepstatin A (10 μg/ml) as well as phenyl methyl sulfonyl fluoride (PMSF, 174 μg/ml) were added as protease inhibitors. The final pHs of the enzyme buffer mixtures were 6.9, 7.8, 9.0 and 9.4. Samples were incubated in the absence of the substrate at 60° C., 70° C. and 80° C. Samples were taken at intervals of 0, 30, 60 and 120 minutes and immediately cooled on ice prior to the residual xylanase activity determination at 50° C. (5 min reaction in the corresponding pH). The enzyme was very stable when incubated at 60° C. and 70° C.; after 120 minutes incubation at 70° C. at pH 9 over 60% of xylanase activity was retained (FIGS. 2, 2A and 2B).

Example 3

Purification of Actinomadura Xylanases

Purification of xylanases from Actinomadura growth medium was performed at +4° C. with chromatographic columns coupled to a FPLC apparatus (Pharmacia). Xylanase activity measurements were performed at 50° C. and at pH 6.5. Protein was monitored at 280 nm throughout the purification. Samples were run on polyacrylamide slab gels containing 0.1% SDS on a Bio-Rad Mini Protean II electrophoresis system and stained with Coomassie Brilliant Blue. A polyclonal antibody prepared against *Thermomonospora fusca* xylanase A (TfxA, obtained from Prof. David Wilson, Cornell University) was used to detect Actinomadura xylanase(s) in Western blots. In the detection, Promega's ProtoBlot® AP System was used.

A growth media of the two 1 l fermentations described above was pooled and centrifuged at 8,000 g for 30 min. The supernatant (1,500 ml) was diluted 1+2 with 12.5 mM $Na_2HPO_4$ pH 9 and adjusted to pH 8.6 with 1 M NaOH. This sample was applied, in two sets, on a DEAE Sepharose CL-6B (Pharmacia) ion-exchanger (2.5×29 cm) equilibrated with 12.5 mM $Na_2HPO_4$, pH 9, at 100 ml/h. The flow-through of both runs was combined and processed separately as described later.

Elution of the bound proteins from the DEAE-column was accomplished by a linear gradient (400 ml+400 ml) from 25 mM $Na_2HPO_4$ pH 9, to 25 mM $Na_2HPO_4$, pH 9 containing 1 M NaCl at a flow rate of 105 ml/h and fractions of 10 ml were collected. Two xylanase activity containing peaks could be collected (pool I and II), as well as a long "tailing" of the second peak (pool III).

The three pools (each combined from both DEAE runs) were adjusted to contain 2 M sodium chloride each and applied separately on a Phenyl Sepharose CL-4B (Pharmacia) column (2.5×15 cm) equilibrated with 25 mM $Na_2HPO_4$, pH 9 containing 2 M NaCl. Elution was performed at 100 ml/h with a two step gradient of 100% buffer A (25 mM $Na_2HPO_4$, pH 9) to 35% buffer B (25 mM $Na_2HPO_4$ containing 60% ethylene glycol) in 60 min followed by a steeper gradient from 35% B to 100% B in 60 min. Fractions of 7 ml (pool I) or 5 ml (pools II and III) were collected. The xylanase activity containing fractions of pool I obtained were pooled and named DEPS I. Both DEAE pools II and III resulted in two xylanase activity containing peaks named DEPS II/1, DEPS II/2 and DEPS III/1, DEPS III/2, respectively.

The flow-through of the DEAE runs (see above) was concentrated with a cut-off membrane of 30 kDa, and adjusted to contain 2 M NaCl. This sample was applied on a Phenyl Sepharose 6 FastFlow (low sub; Pharmacia) column (2.5×34 cm) equilibrated with 25 mM $Na_2HPO_4$, pH 9, containing 2 M NaCl. Elution was accomplished at 300 mlh$^{-1}$ with the same gradient as was used for DEAE pools on Phenyl Sepharose CL-6B and fractions of 10 ml were collected. Xylanase activity containing peaks obtained were named KFI, KFII and KFIII. The permeate from the concentration was subjected to an identical Phenyl Sepharose 6 FastFlow (low sub) run, and the xylanase activity containing fractions were named PFI and PFII.

All the DEPS, KF and PF peaks obtained were dialyzed against 25 mM $Na_2HPO_4$ overnight.

Figure 3:
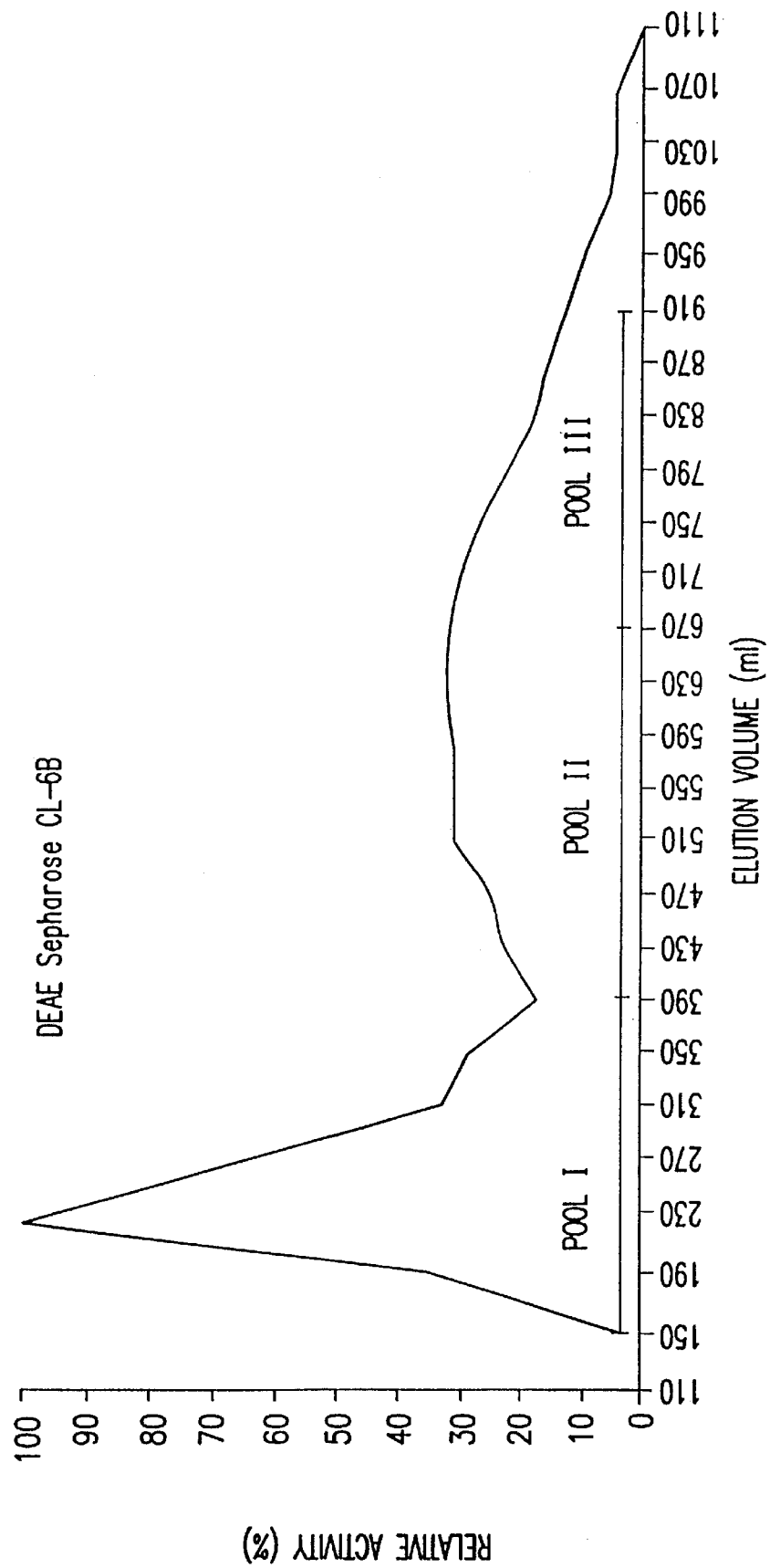
FIG. 3 shows the DEAE Sepharose CL-6B chromatography elution profile of *A. flexuosa* (DSM43186) xylanases.
Figure 4:
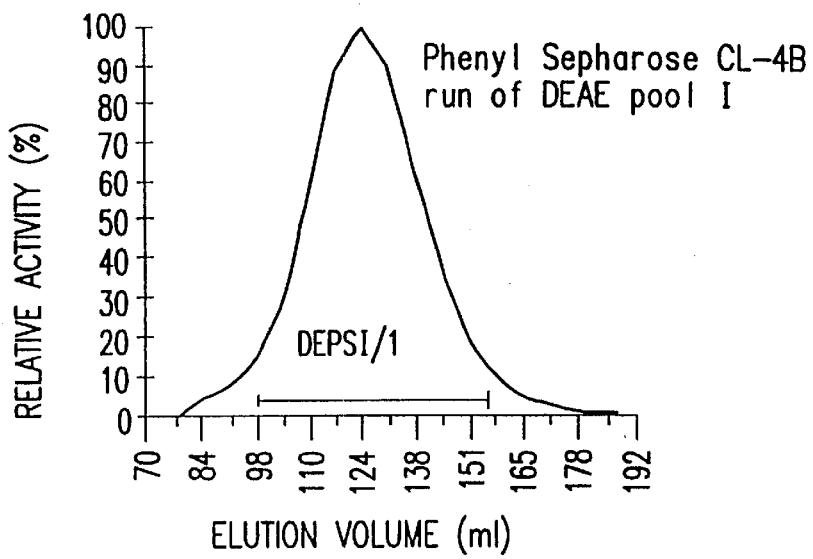
FIG. 4 shows the Phenyl Sepharose CL-4B chromatography elution profile of DEAE pool I of FIG. 3. The fractions that were combined to provide sample DEPS I/1 are indicated.
Figure 4A:
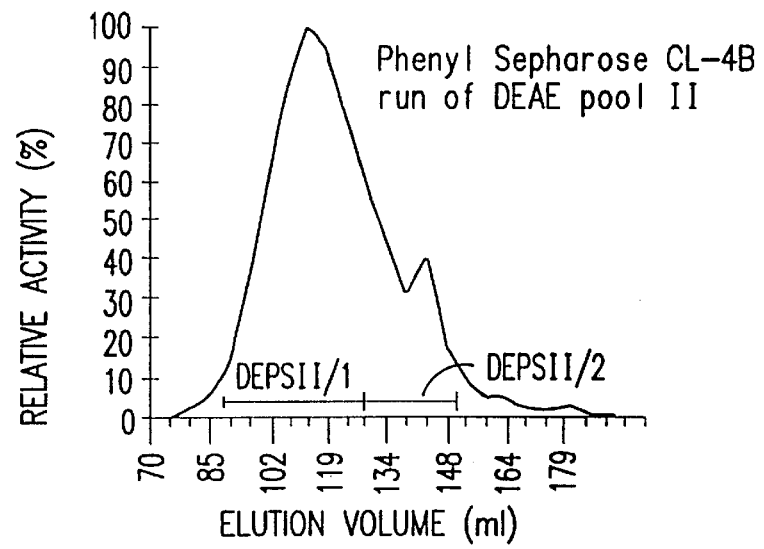
FIG. 4A shows the Phenyl Sepharose CL-4B chromatography elution profile of DEAE pool II of FIG. 3. The fractions that were combined to provide sample DEPS II/1 and DEPS II/2 are shown.
Figure 4B:
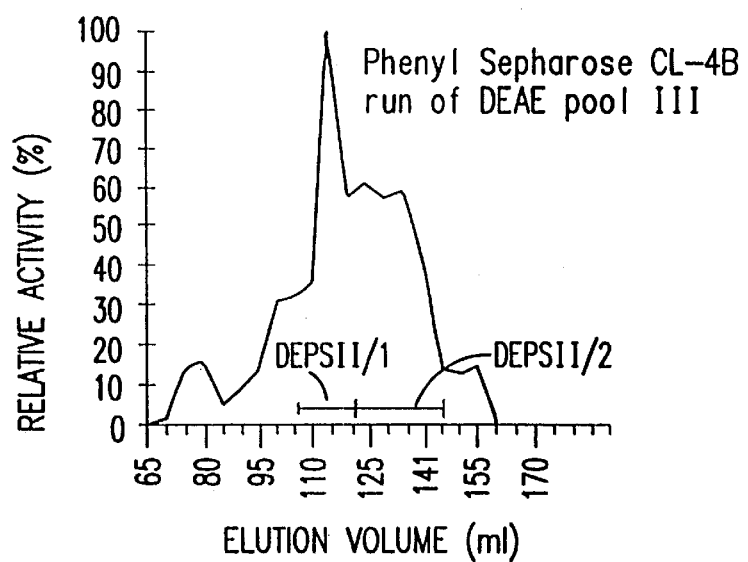
FIG. 4B shows the Phenyl Sepharose CL-4B chromatography elution profile of DEAE pool III of FIG. 3. The fractions that were combined to provide sample DEPS III/1 and DEPS III/2 are shown.

Roughly half of the xylanase activity was bound to DEAE Sepharose in the first purification step. Elution of the DEAE proteins from this ion-exchanger resulted in a quite sharp peak followed by a broad "peak" (FIG. 3). This broad "peak" was divided into two different pools. Each of these pools were further purified on a hydrophobic interaction chromatography (HIC) column (FIGS. 4, 4A and 4B). Some differences could be seen, in that pool I from DEAE resulted in a homogeneous peak on HIC (FIG. 4), but both pools II (FIG. 4A) and III (FIG. 4B) resulted in at least two peaks. Samples of these pools were run on SDS-PAGE and stained for protein with Coomassie Blue (FIG. 5) as well as analyzed by Western blots with *T. fusca* antibody (FIG. 5A). The antibody reacted only with two to three bands of smaller molecular mass (35 kDa or lower) from the growth medium and weakly with the proteins in these pools. The apparent molecular masses of the proteins in these pools were 50 kDa as estimated from SDS-PAGE with molecular mass standards. Pools DEPS II/2, DEPS III/1 and DEPS III/2 were the most pure.

The flow-through of the DEAE ion-exchanger was concentrated with a cut-off membrane of 30 kDa. Roughly half of the xylanase activity was found in the concentrate and half in the permeate. Both were purified further by hydrophobic interaction chromatography, resulting in two xylanase activity peaks for the permeate (FIG. 6) and three for the concentrate (FIG. 6A). These peaks were analyzed on SDS-PAGE as well as on Western blots (FIG. 7). The first peak, KF1, from the concentrate showed a band of 40 kDa apparent molecular mass on SDS-PAGE, but no reaction on Western blots. However, this peak had the highest xylanase activity. KF2 showed a band of 50 kDa on SDS-PAGE reacting weakly with the antibody, but a clear band of 30 kDa could be seen on Western blots. The third peak, KF3, showed a band of 35 kDa on Western blots. The concentrate contained xylanases with apparent molecular weights of 50, 40, 35 as well as 30 kDa. The first peak, PF1, from the permeate reacted with *T. fusca* antibody showing two bands of 35 kDa and 30 kDa, respectively. PF2, on the other hand, showed only one band of 35 kDa on Western blots.

As a summary, Actinomadura sp. DSM43186 growth medium contains xylanases with molecular mass of about 50, 40, 35 and 30 kDa. Of these, the 35 kDa and 50 kDa proteins appear as the major bands (on SDS-PAGE) of molecular mass. It is possible that the 40 kDa xylanase band on SDS-PAGE is a degradation product of the 50 kDa band on SDS-PAGE and that the 30 kDa band on SDS-PAGE is a degradation product of 35 kDa xylanase band on SDS-PAGE.

Example 4

Production and Sequencing of Peptides

A sample (12 ml) of pool I from the DEAE Sepharose CL-6B (FIG. 3) run was subjected to gel exclusion chromatography on a HighLoad 26/60 Superdex G75 column (Pharmacia) equilibrated with 25 mM $Na_2HPO_4$, pH 9 at 120 ml/h. A sample (25 ml) of the xylanase activity containing peak fraction obtained was diluted (1+1) with water and applied on a mono Q (Pharmacia) ion-exchanger equilibrated with 12.5 mM $Na_2HPO_4$, pH 9. Elution was performed at 30 ml/h with a linear gradient from 12.5 mM $Na_2HPO_4$, pH 9 to 12.5 mM $Na_2HPO_4$, pH 9 containing 0.5 M NaCl in 50 min. The xylanase activity containing peak (1 ml) was concentrated on a Centricon micro concentrator (cut-off 30 kDa) and eluted with 1% ammonium bicarbonate. This concentrated sample was evaporated and alkylated with vinylpyridin. The alkylated sample was digested with trypsin (modified trypsin, sequenal grade, Promega V5111). The digest was applied on a reverse phase column coupled to an HPLC, and peaks absorbing at 214 nm were collected manually. Each of the collected fractions were subjected to Edman degradation in a gas-pulsed-liquid-phase sequencer (Kalkkinen & Tilgmann, *J. Protein Chem.* 7:242–243 (1988)) and the released PTH amino acids were analyzed on-line by using narrow bore reverse phase HPLC.

Peptides obtained from the purified 50 kDa xylanase are listed in Table 1.

TABLE 1

Peptides (SEQ ID NO:17–22) from the purified 50 kDa xylanase

| Peptide | Sequence |
|---|---|
| # 1696 (SEQ ID NO:17) | Ala-Ala-Ser-Thr-Leu-Ala-Glu-Gly-Ala-Ala-Gln-His-Asn-Arg |
| # 1697 (SEQ ID NO:18) | Tyr-Phe-Gly-Val-Ala-Ile-Ala-Ala-Asn-Arg |
| # 1698 (SEQ ID NO:19) | Leu-Asn-Asp-Ser-Val-Tyr-Thr-Asn-Ile-Ala-Asn-Arg |
| # 1699 (SEQ ID NO:20) | Asn/Gly/X-Thr-Gly-Ile-Thr-Val-X-Gly-Val |
| # 1703 (SEQ ID NO:21) | His/Glu/Thr-Glu/Phe-Leu/Asn-Val/Ser-Tyr/Val-Asn/Thr-Met/Ala-Val/Glu-Asn/X-Glu/X-Met/X |
| # 1704 (SEQ ID NO:22) | Glu-Phe-Asn-Ser-Val-Thr-Ala-Glu-Asn-Glu-Meet-(Lys) |

The combination of the peptide sequences #1696 (SEQ ID NO:17) 1697 (SEQ ID NO:18) 1698 (SEQ ID NO:19) and 1704 (SEQ ID NO:22) corresponds with 75% similarity to amino acids 42–89 in *Streptomyces lividans* xylanase A. In addition, peptide #1699 (SEQ ID NO:20 shows 78% similarity to amino acids 301–309 in *S. lividans* XlnA (SEQ ID NO:27).

```
                      (SEQ ID NO 17)(SEQ ID NO 18)(SEQ ID NO 19)(SEQ ID NO 22)
Actinomadura              #1696          #1697         #1698         #1704
      50 kDa    1 AASTLAEGAAQHNR YFGVAIAANR LNDSVYTNIANR EFNSVTAENEMK 48
                  |.|||:.:|||  .| |||.|||..|  |.||.||.||.|  ||| ||||||||
  S.lividans   42 AESTLGAAAAQSGR YFGTAIASGR LSDSTYTSIAGR EFNMVTAENEMK 89
        XlnA     (SEQ ID NO 23)(SEQ ID NO 24) (SEQ ID NO 25)(SEQ ID NO 26)

(SEQ ID NO 20)
Actinomadura              #1699
      50 kDa       G
                   NTGITVXGV
                   ||||:||
  S.lividans       SRCLGITVWGVRD
        XlnA     300       310
                      (SEQ ID NO 27)
```

Example 5

The pH Properties and Temperature Stability of the Purified 35 kDa and 50 kDa Xylanases The temperature stability of the purified 35 and 50 kDa enzymes (±100 μg/ml BSA) was determined by incubating the enzyme samples at 70° C., pH 6.0 for a period of 0, 2, 6 and 24 hours after which the xylanase activity of the samples was determined (at pH 6.5, 60° C., 20 min reaction). In the samples into which BSA had been added, over 80% of the original activity could be measured even after 24 h of incubation (FIGS. 8 and 9 for the 35 kDa and the 50 kDa xylanases, respectively). When BSA was not added, still about 60% (35 kDa) or 70% (50 kDa) of the original activity was measured after 24 h of incubation (FIGS. 8 and 9).

The pH dependence was determined by incubating the enzyme samples at different pH values (pH 4–8) and at temperatures of 80° C. (35 kDa) and 60, 70 and 80° C. (50 kDa) for 20 minutes (35 kDa) or 10 minutes (50 kDa) or 10 minutes (50 kDa). At 80° C., the 35 kDa xylanase showed a pH optimum of around pH 6 having nearly 90% of its activity from about pH 5 to 7 (FIG. 10). At 60° C. and 70°, the 50 kDa xylanase showed a pH optimum of pH 5–7 and at 80°, a pH optimum of pH 6–7. The enzyme was very stable from pH 5–7 under these conditions (FIG. 10A). Incubation of both 35 kDa and 50 kDa xylanases at 60° C. for 60 minutes at pH values from 4.2 to 8.7 showed similar stability as found in the above experiment, except that the 50 kDa xylanase seems to be less stable at pH 4.2 under these conditions (FIG. 10B). Temperature dependence experiments at pH 7 with 60 minute incubations of the 35 kDa and 50 kDa xylanases with substrate at temperatures of 50, 60, 70 and 80° C. showed maximal activity at 70° C. for both enzymes (FIG. 11). The 50 kDa xylanase seemed from these results to be slightly more stable at 80° and ph & than the 35 kDa xylanase. On the other hand, the 35 kDa xylanase showed more activity and stability in the pH range of 4–5.

Example 6

Bleaching Experiments Using the Actinomadura Culture Supernatant

A sequence of bleaching trials was done to determine the usefulness of *Actinomadura flexuosa* xylanase in both ECF (elementary chlorine free) and TCF (totally chlorine free) bleaching of kraft pulp.

ECF Bleaching

Growth media containing *Actinomadura flexuosa* xylanase (see Example 1) was added to Finnish oxygen-delignified softwood kraft pulp (kappa number=15) in the amount of 50 or 100 nkat/g pulp dry matter, at pH 7 and 70° C. for 1 hour. This culture medium is very low in endoglucanases and cellulases. Reference pulp was kept under the same conditions without enzyme addition.

All pulps were then similarly bleached in two steps: chlorine dioxide and alkaline extraction. The absorbance of the filtrate at 280 nm was determined as a measure of dissolved lignin.

As can be seen in Table 2, after pretreatment with the xylanase more lignin was removed (as evidenced by the change in the $A^{280}$). The final pulps had 3–4 units higher brightness without losing the strength of the pulp (the viscosity change of 20 units is inside the normal variation of the method).

TABLE 2

|  | 0 nkat/g | 50 nkat/g | 100 nkat/g |
| --- | --- | --- | --- |
| Enzyme Stage |  |  |  |
| Consistency, % | 3 | 3 | 3 |
| Temperature, ° C. | 70 | 70 | 70 |
| pH at start/end | 7.0/7.1 | 7.0/7.2 | 7.2/7.4 |
| Retention time, min. | 60 | 60 | 60 |
| A280 (dil. 1/10) | 0.22 | 0.49 | 0.65 |
| ClO$_2$ Stage |  |  |  |
| Consistency, % | 3 | 3 | 3 |
| ClO$_2$-dosage, % | 2.3 | 2.3 | 2.3 |
| Temperature, ° C. | 60 | 60 | 60 |
| pH at end | 2.4 | 2.5 | 2.5 |
| Retention time, min. | 60 | 60 | 60 |
| Extraction Stage |  |  |  |
| Consistency, % | 10 | 10 | 10 |
| NaOH dosage, % | 1.5 | 1.5 | 1.5 |
| Temperature, ° C. | 70 | 70 | 70 |
| pH at end | 10.9 | 10.9 | 10.9 |
| Retention time, min. | 60 | 60 | 60 |
| Final Pulp |  |  |  |
| Brightness, % ISO | 56.7 | 59.9 | 60.6 |
| Kappa number | 6.6 | 5.6 | 5.4 |
| Viscosity dm$^3$/kg | 920 | 910 | 900 |

TCF Bleaching

Finnish oxygen-delignified softwood kraft pulp, with kappa number of 15, was treated with *Actinomadura flexuosa* xylanase using enzyme dosages of 50 and 100 nkat/g pulp dry matter. The treatment was done at pH 7 at 70° C. for 1 hour. Reference pulp was kept under the same conditions without enzyme addition.

After this, all the pulps were similarly bleached in two steps: metal removal by chelation with EDTA and hydrogen peroxide. The absorbance of the filtrate at 280 nm was determined as a measure of dissolved lignin.

Table 3 shows that according to the $A^{280}$ measurement and kappa number, significantly more lignin was removed after xylanase pretreatment, while the strength of the pulp (according the viscosity) remained good.

Example 7

Bleaching Experiments Using the Purified 35 kDa and 50 kDa Xylanases

The purified larger 50 kDa (AM50) xylanase and the smaller 35 kDa (AM35) xylanase (including also the 30 kDa xylanase) were used for bleaching experiments in a three-stage peroxide bleaching. The purified enzyme preparations were the same as used in the determination of the pH and temperature properties for the purified enzymes.

A control sample without any enzyme treatment was also included. The dry weight content and kappa number of the starting softwood pulp (V 541–18 (2129)) were 28.8% and 13.5, respectively. The starting brightness of the pulp was 37.1.

TABLE 3

|  | 0 nkat/g | 50 nkat/g | 100 nkat/g |
| --- | --- | --- | --- |
| Enzyme Stage |  |  |  |
| Consistency, % | 3 | 3 | 3 |
| Temperature, ° C. | 70 | 70 | 70 |

TABLE 3-continued

|  | 0 nkat/g | 50 nkat/g | 100 nkat/g |
|---|---|---|---|
| pH at start/end | 7.0/7.4 | 7.0/7.3 | 7.0/7.3 |
| Retention time, min. | 60 | 60 | 60 |
| Abs 280 nm (dil. 1/10) | 0.27 | 0.43 | 0.57 |
| Chelation Stage |  |  |  |
| Consistency, % | 3 | 3 | 3 |
| EDTA, % | 0.2 | 0.2 | 0.2 |
| Temperature, ° C. | 70 | 70 | 70 |
| pH at end | 5.5 | 5.6 | 5.8 |
| Retention time, min. | 60 | 60 | 60 |
| Abs 280 nm (dil. 1/10) | 0.24 | 0.44 | 0.64 |
| Consistency, % | 10 | 10 | 10 |
| $H_2O_2$ dosage, % | 3.0 | 3.0 | 3.0 |
| $H_2O_2$ consumption, % | 0.87 | 0.85 | 0.91 |
| DTPA, % | 0.2 | 0.2 | 0.2 |
| $MgSO_4$, % | 0.5 | 0.5 | 0.5 |
| NaOH, % | 3.0 | 3.0 | 3.0 |
| Temperature, ° C. | 80 | 80 | 80 |
| pH at end | 10.6 | 10.6 | 10.6 |
| Retention time, min. | 180 | 180 | 180 |
| Final Pulp |  |  |  |
| Brightness, % ISO | 71.9 | 72.9 | 73.0 |
| Kappa number | 9.0 | 8.3 | 7.9 |
| Viscosity $dm^3$/kg | 870 | 890 | 890 |

Enzyme Treatment and Dosage

The activity of the enzyme was measured at 60° C., pH 6.5, with birch wood xylan (Roth No. 7500) as a substrate. The enzyme dosage was 100 nkat/g of dry pulp. The Actinomadura xylanases were dissolved in 25 mM disodium phosphate buffer including 50 mM NaCl and the same amount of this buffer was added to the control sample. The pH of the pulp was adjusted with sulfuric acid.

Chelation

The chelation was performed by adding EDTA to 0.2% of dry weight and it was carried out at 3.0% consistency at 50° C. for one hour.

Peroxide Bleaching

The three peroxide bleaching stages (80° C., 180 min) were carried out the same way except that after each stage, one-third of the pulp was removed for testing. The conditions used were the following:

| Consistency | 10% |
|---|---|
| $H_2O_2$ | 3% |
| NaOH | 3% |
| DTPA | 0.2% |
| $MgSO_4$ | 0.5% |

The results with Ecopulp X-2000® enzyme preparation (Primalco Ltd. Biotec., Rajamäki, Finland) containing *T. reesei* xylanase II are also included. The starting pulp and all other treatments are the same except that the enzyme treatment (100 nkat/g of dry weight) was carried out in water, pH 5.0 at 50° C., which is close to the optimum of the *T. reesei* xyl II. The activity of the enzyme was measured at 60° C., pH 6.5, with birch wood xylan (Roth No. 7500) as substrate. The control sample was treated in the same way but without the enzyme.

The reducing sugars (% dry weight) were analyzed after the enzyme treatment and were the following:

|  | % |
|---|---|
| Control | 0.19 |
| AM50 | 1.18 |
| AM35 | 1.64 |
| Control | 0.20 |
| Ecopulp X-200 ® | 1.32 |

The results from the bleachings are shown in Table 4.

TABLE 4

|  | ISO Brightness | Kappa | Peroxide used (%) |
|---|---|---|---|
| P1 Stage |  |  |  |
| Control | 59.6 | 5.9 | 2.7 |
| AM50 | 62.3 | 6.3 | 2.7 |
| AM35 | 63.7 | 5.3 | 2.6 |
| Control | 62.2 | 5.9 | 2.2 |
| Ecopulp X-200 ® | 64.1 | 7.2 | 2.3 |
| P2 Stage |  |  |  |
| Control | 67.2 | 6.8 | 2.2 |
| AM50 | 69.7 | 4.8 | 2.4 |
| AM35 | 70.7 | 4.9 | 2.2 |
| Control | 68.8 | 7.7 | 2.2 |
| Ecopulp X-200 ® | 70.6 | 5.5 | 2. |

The use of AM50 and AM35 clearly increased the brightness obtained without increasing the amount of peroxide that was used.

Example 8

Isolation of the Chromosomal DNA and Construction of the Genomic Library

*Actinomadura flexuosa* sp. DSM43186 was cultivated in 50 ml of medium consisting of 10% (w/v) sucrose, 0.5% (w/v) oat spelt xylan, 0.5% (w/v) peptone from casein, 0.5% (w/v) yeast extract, 0.5% (w/v) beef extract, 0.074% (w/v) $CaCl_2 \times 2H_2O$, pH 7.4–7.5, in baffled shake flask for 2.5 days at 52° C. with shaking at 200 rpm. 2.5 ml of this culture was transferred to 50 ml of fresh medium supplemented with 0.8% glycine, and grown for 2 days at 50° C., 200 rpm. Cells were pelleted by centrifugation and washed with 10% sucrose-25 mM Tris-HCl (pH 8.0)-25 mM EDTA.

The chromosomal DNA was isolated according to Hopwood et al., Genetic manipulation of Streptomyces: A laboratory manual, The John Innes Foundation, Norwich, UK (1985). Briefly, the mycelium was lysed with lysozyme and 2×Kirby mixture (2 g sodium triisopropylnaphthalene sulphonate, 12 g sodium 4-amino-salicylate, 5 ml 2 M Tris-HCl (pH 8.0), 6 ml of Tris-HCl saturated phenol, made up to 100 ml with water). The DNA was precipitated with isopropanol and dissolved into TE (10 mM Tris-HCl, 1 mM EDTA, pH 8.0). RNA was digested with RNase.

The chromosomal DNA was partially digested with Sau3A (Boehringer) and size-fractionated in sucrose gradient (10–40% (w/v) sucrose in 1 M NaCl, 20 mM Tris-HCl, pH 8.0, 5 mM EDTA) run at 55,000 rpm for 6h at 22° C. in the Beckman TL-100 ultracentrifuge in the TLS-55 rotor. The gradient was divided in fractions, and those containing DNA of mainly 7–10 kb in size were used to construct a genomic Actinomadura library.

The predigested ZAP Express™ BamHI/CIAP Vector Cloning Kit (Stratagene) was used to construct the library and the instructions of the manufacturer were followed in all the subsequent steps. Briefly, about 200 ng of size-fractionated DNA was ligated into 1 μg of ZAP Express prepared arms, and packaged using Gigapack II packaging extract (Stratagene). The titer of the library was determined by infecting E. coli XL1-Blue MRF' cells with serial dilutions of the packaged phage and plating on NZY plates. The total titer of the ligation mixture was approximately $3 \times 10^7$ pfu/ml, with over 96% insert frequency. The library was used for screening without amplification.

Example 9A

Isolation of the Gene Encoding the 35 kDa Xylanase on the Basis of Hydrolyzing Activity on RBB-xylan Plates The genomic library of Actinomadura flexuosa sp. DSM43186 DNA in ZAP Express™ vector was screened for xylanolytic activity, as follows. the host, Stratagene E. coli XL-Blue MRF' cells were grown in LB+0.2% (w/v) maltose+10 mM $MgSO_4$ and adjusted to $OD_{600}$=0.5. The cells were infected with the recombinant library for 15 min at 37° C. and plated with NZY top agar on the NZY plates. The plates were incubated for 4 hrs at 42° C., overlaid with nitrocellulose filters saturated with 10 mM IPTG to induce the lacZ-fusion protein expression, and incubated over night at room temperature.

The filters were washed with 50 mM K-phosphate buffer (pH 6.8), and transferred onto RBB-xylan+Km plates. The plate has two layers; lower layer of 15 ml of regular LB+Km (40 μg/ml) and upper layer of 5 ml of RBB xylan (0.5% (w/v) RBB xylan, 1% (w/v) oats spelts xylan in LB+Km, buffered with 50 mM K-phosphate, pH 6.8). The plates were transferred to 50° C. for a second night to determine xylanolytic activity. Filters were removed, and the clear halo on the RBB-xylan+Km plates revealed the clones having xylanase activity. 22 positive plaques from the original NZY-plates were picked in SM buffer/chloroform.

The ZAP Express vector has been designed to allow simple, efficient in vivo excision and recircularization of any cloned insert contained within the lambda vector to form a phagemid containing the cloned insert. Briefly, the positive clones were incubated with XL1 Blue MRF' cells with the ExAssist helper phage. After heat denaturation (70° C., 15 min), and centrifugation, the excised phagemid pBK-CMV is packaged as filamentous phage particles in the supernatant. The rescued phagemid was mixed with XLOLR cells, and plated on LB/kanamycin (50 μg/ml) according to the manufacturer.

E. coli XLOLR cells transformed with the rescued phagemid DNAs were retested on RBB-xylan+Km. From the 22 originally positive clones 12 retained the xylanase activity. The phagemid DNAs were digested with EcoRI-PstI, electrophoresed, blotted onto a nylon membrane, and hybridized with a digoxigenin-labeled 1.15 kb T. fusca xylanase fragment from pALK185 (FIG. 12). The plasmid pALK185 contains the T. fusca xynA gene from pTX101 (Ghangas, G. S. et al., J. Bact. 171:2963–2969 (1994)). Four phagemids hybridized with the T. fusca DNA probe, indicating that they carried gene(s) sharing some homology with the T. fusca fragment. These phagemids were designated pALK938, pALK939, pALK940 and pALK941.

Example 9B

Isolation of the Gene Encoding for the 35 kDA Xylanase on the Basis of Hybridizing to the T. fusca xynA Gene The genomic library of Actinomadura flexuosa sp. DSM43186 DNA in ZAP Express™ vector was screened with a digoxigenin-labeled 1.15 kb T. fusca xylanase fragment from pALK185 (FIG. 12), according to supplier's instructions. 17 positive clones were picked. The phagemids were excised in vivo, as described above in example 9A. The E. coli clones harboring the positive phagemids were tested for xylanolytic activity on RBB-xylan, as described above in example 9A. 11 clones showed xylanolytic activity. One of the clones was chosen, and the plasmid was designated pALK1056.

Example 10

Isolation of the Gene Encoding the 35 kDa Xylanase on the Basis of Production of Polypeptide Recognized by the T. fusca TfxA Antibody The polyclonal antibody against Thermomonospora fusca 32 kDa xylanase, TfxA, was used to screen the Actinomadura genomic library. Stratagene XL1-Blue MRF' cells were grown in LB+0.2% maltose+10 mM $MgSO_4$ and diluted to $OD_{600}$=0.5. The cells were infected with the recombinant library for 15 min at 37° C. and plated with NZY top agar on the NZY plates. Plates were incubated for 3.5 hours at 42° C., overlaid with nitrocellulose filters saturated with 10 mM IPTG, and incubated overnight at room temperature. Detection was performed with the 1:1500 diluted T. fusca TfxA antibody using Promega's ProtoBlot® AP System. Twelve positive clones, of which the clone 1.1 clearly gave the strongest signal, were picked in SM buffer/chloroform, and purified with a second round of screening.

The phagemids were excised in vivo, as described above in example 9A. The phagemids were were then digested with EcoRI and PstI, electrophoresed, blotted onto a nylon membrane and hybridized with a digoxigenin-labeled 1.15 kb T. fusca xylanase fragment from pALK185 (FIG. 12). Of the Actinomadura flexuosa sp. DSM43186 chromosomal DNA, the T. fusca xynA probe hybridized to about a 4 kb EcoRI-Pst fragment. The clones were also tested for xylanolytic activity on RBB-xylan, as described above in example 9A. One clone (clone 1.1) was positive in both screens. The phagemid carried by this clone was designated pALK923.

Example 11

Restriction Enzyme Analysis and Sequencing of the Xylanase Gene Coding for the 35 kDa Protein The plasmids pALK938, pALK939, pALK940, pALK941, pALK1056 and pALK923 were analyzed by restriction enzyme analysis, and were used for sequencing of the xylanase gene. The DNA was sequenced by using ABI (Applied Biosystems) kits based on fluorescent-labeled T3 and T7 primers, or sequence-specific primers with fluorescent-labelled dideoxynucleotides, by the Taq dye primer cycle sequencing protocol in accordance with the supplier's instructions. Because of the high GC content in the Actinomadura DNA, the sequencing reactions were performed with 10% (v/v) DMSO, at annealing temperature of 58–60° C. Sequencing reactions were analyzed on ABI 373A sequencer, and the sequences obtained were characterized by using the Genetics Computer Group Sequence Analysis Software Package, version 7.2 The DNA sequence encoding the 35 kDa xylanase is presented in FIG. 13. The sequence shows an ORF (open reading frame) of 1035 bp, predicting a polypeptide of 344 amino acids, and corresponding to a protein with a molecular weight of about 37.5 kDa. A putative signal processing site is found after alanine 43, and the predicted mature protein has a calculated molecular weight of about 32.9 kDa. The sequence data is thus in good agreement with the 35 kDa xylanase purification results described in Example 3. The 35 kDa gene sequence appeared identical in all the tested clones, except in the pALK923 DNA. pALK923 contained 93 bp of unknown sequence at the N-terminus of the insert, after which the Actinomadura 35 kDa xylanase gene sequence started at the location corresponding to base pair 411 in FIGS. 13–13A.

Three positive plaques were picked after an overnight detection. These clones were named Act.xyl.50/13, Act.xyl.50/14 and Act.xyl50/15.

The phagemids containing the cloned Actinomadura insert were excised as described in Example 9A. To determine the xylanase activity, the *E. coli* clones were streaked on RBB-xylan+Km plates as described in Example 9A, using the strain producing the Actinomadura 35 kDa xylanase (from plasmid pALK923) as a positive control. The clones Act.xyl.50/13 and Act.xyl.50/14 showed xylanase activity, giving a clear halo around the colony.

TABLE 5

Oligonucleotide primers used in the detection of the gene coding for the Actinomadura 50 kDa xylanase

| Primer | DNA sequence |
| --- | --- |
| Actinomadura sp. DSM43186 | |
| #1696s | GCA/C/G/TGCA/C/G/TCAA/G/CAC/TAAC/TA/CG |
| #1703as | ACCATA/GTTA/GTAA/C/G/TACA/C/G/TA |
| #1704as | TTCATC/TTCA/GTTC/TTCA/C/G/TGC |
| S. lividans xlnA 331–369as | |
| | CGTGAGTTCAACATGGTGACGGCCGAGAACGAGATGAAG |
| S. lividans xlnA 257–284s | |
| | AGAGCGGCCGCTACTTCGGCACCGCCAT |
| S. lividans xlnA 530–561as | |
| | CACGCCGTTGATGTGGTCGATCATCGCCTGGC | s = sense; as = antisense

The sequence shows high homology towards xylanases from different organisms. At amino acid level, the gene shows about 76% homology towards the *T. fusca* XynA.

Example 12

Isolation of the 50 kDa Actinomadura Xylanase Gene

The genomic library of *Actinomadura flexuosa* sp. DSM43186 DNA in ZAP Express™ vector was screened using a DNA probe.

Oligonucleotide primers were designed based on the peptide sequences derived from the purified 50 kDa protein. The primer sequences are presented in Table 5. Because the combination of peptide sequences #1696 (SEQ ID NO:17), #1697 (SEQ ID NO:18), # 1698 (SEQ ID NO:19) and #1704 (SEQ ID NO:22) corresponds with 75% similarity to amino acids 42–89 in *Streptomyces lividans* xylanase A, a 39 bp antisense oligo was synthesized, from bases 331 to 369 in the *S. lividans* xlnA sequence. The *S. lividans* xlnA 331–369as probe (SEQ ID NO:31) and the primers #1704as (SEQ ID NO:30), #1703as (SEQ ID NO:29), #1696s (SEQ ID NO:28) were labeled with digoxigenin and terminal transferase, and used as probes in hybridization at 50° C. according to Boehringer, DIG DNA Labeling and Detection Nonradioactive, Applications Manual.

The #1704as (SEQ ID NO:30) and the *S. lividans* xlnA as (SEQ ID NO:31 probe recognized the same 1.0 kb EcoRI-PstI fragment in Actinomadura DNA. The fragment is different from the 4 kb fragment recognized by the *T fusca* xynA probe. Based on these results, the 39 mer *S. lividans* xlnA as probe was used to screen the Actinomadura library for the 50 kDa xylanase coding gene.

Example 13

Sequencing the Gene for the 50 kDa Xylanase Protein

The phagemid DNAs from the Act.xyl.50/13 and Act.xyl.50/14 were named pALK927 and pALK928, respectively. The *S. lividans* xlna 331–369as oligomer was used to sequence the Actinomadura insert. In addition, two oligomers corresponding to nucleotides 257–284 and 530–561 in the *S. lividans* xlnA sequence, as well as sequence-specific primers, were synthesized to obtain sequence from the cloned insert. The sequencing reactions were performed with 10% (v/v) DMSO, at the annealing temperature of 58° C. The sequencing was performed as described in Example 11. The sequence of the 1864 bps of the Actinomadura sp. DSM43186 50 kDa xylanase gene is presented in FIGS. 14–14A. Peptide sequences obtained from the purified 50 kDa protein are indicated by underlining of the derived amino acid sequence. The derived peptide sequence shows 70–71% identity towards Actinomadura sp. FC7 xylanase II (FIGS. 15–15A) and *S. lividans* xylanase A (FIGS. 15B–15C) proteins. The sequence shows an ORF of 1479 bpas, predicting a polypeptide of 492 amino acids, corresponding to a protein with a molecular weight of about 53.5 kDa.

Example 14

Fusion Proteins

A recombinant vector encoding a xylanase gene is prepared by fusing the xylanase encoding sequence with the sequence of a *T. reesei* cellulase or hemicellulase or at least one functional domain of said cellulase or hemicellulase, as described in U.S. Pat. No. 5,298,405, WO 93/24621 and in GenBank submission L25310, incorporated herein by reference. Especially, the enzyme is selected from the group consisting of CBHI, CBHII, EGI, EGII, XYLI, XYLII and mannanase (MANI), or a domain thereof, such as the secretion signal or the core sequence.

Fusion proteins can be constructed that contain an N-terminal mannanase or cellobiohydrolase or endoglucanase core domain or the core and the hinge domains from the same, fused to the Actinomadura xylanase sequence. The result is a protein that contains N-terminal mannanase or cellobiohydrolase or endoglucanase core or core and hinge regions, and a C-terminal Actinomadura xylanase. The fusion protein contains both the mannanase or cellobiohydrolase or endoglucanase and xylanase activities of the various domains as provided in the fusion construct.

Fusion proteins can also be constructed such that the mannanase or cellobiohydrolase or endogluanase tail or a desired fragment thereof, is included, placed before the Actinomadura xylanase sequence, especially so as to allow use of a nonspecific protease site in the tail as a protease site for the recovery of the xylanase sequence from the expressed fusion protein. Alternatively, fusion proteins can be constructed that provide for a protease site in a linker that is placed before the Actinomadura xylanase, with or without tail sequences.

Example 15

Hosts

The recombinant construct encoding the desired bacterial proteins or fusion proteins are prepared as above, and transformed into a filamentous fungi such as Aspergillus spp., preferably Trichoderma spp.

Example 16

Production of Thermomonospora Fusca xylanase in *T. reesei*

The expression cassette pALK193 (FIG. 16) was constructed for expression of the *T fusca* xylanase gene, xynA (Ghangas et al.,*J. Bacteriol* 171:2963–2969 (1989); Irwin et al., *App. & Environ. Microbiol.* 60:763–770 (1994)) in *T. reesei*. In the expression cassette, the *T. fusca* xylanase gene is fused to the *T. reesei* cellobiohydrolase 1 (cbhl) signal sequence that is proceeded by the cbhl promoter. The 9.4 kb pALK193 expression cassette was cut from the vector backbone by EcoRI restriction. It was then isolated, purified and transformed into *T. reesei* ALKO2221 strain. All the fragments and fusions were done by PCR (polymerase chain reaction) have been sequenced to ensure that no errors have occurred during the reaction.

The expression fragment pALK193 contains:

*T. reesei* cbhl promoter and signal sequence: The approximately 2.1 kb promoter sequence was derived from the plasmid pAMH110 (EP 0244.234—FIG. 15) and was originally isolated from *T. reesei* strain VTT-D-80133 (Teeri et al., *Bio/Technol.* 1:696–699 (1983)). The promoter, EcoRI-SacII fragment in pAMH110, was filled in full promoter by adding the missing 10 bps after SacII (before ATG) in the construction by using PCR method. Also, the signal sequence and the exact fusion of the *T. fusca* xylanase gene to the cbhl signal sequence were done by PCR. The sequence of the cbhl signal sequence and the promoter area preceding the ATG is published in Shoemaker et al., *Bio/Technol.* 1:691–696 (1983). The last 15 nucleotides of the *T. reesei* L27 cbhl promoter (the SacII site is underlined) are CCGCGGACTGGCATC (Shoemaker et al. (1983)). The cbhl promoter from the *T. reesei* strain VTT-D-80133 has been sequenced in our laboratory, and one nucleotide difference in the DNA sequence was found within the above mentioned region. In the *T. reesei* strain VTT-D-80133 the sequence preceding the ATG is CCGCGGACTGCGCATC (the SacII site is underlined, the additional cytosine in the DNA sequence is bolded).

*T. fusca* xylanase gene (xynA): The cloning of the xynA gene is published in Ghangas et al., *J. Bacteriol.* 171:2963–2969 (1989), and the sequence of the gene is published in Irwin et al, *App. & Environ. Microbiol.* 60:763–770 (1994). The sequence coding for the mature enzyme was fused to the cbhl signal sequence. About a 0.7 kb xynA terminator region, to the SmaI site after the STOP codon of the xynA coding region, precedes the cbhl terminator fragment in the construction.

*T. reesei* cbhl terminator: The 0.7 kb terminator fragment starting 113 bp before the STOP of the cbhl gene was derived from the plasmid pAMH110 (originally isolated from *T. reesei* VTT-D-80133 (Teeri et al., *Bio/Technol.* 1:696–699 (1983)). The NdeI-PstI fragment was obtained from pAMH110. This fragment contains three TAA codons in all reading frames preceding the 0.7 kb AvaII fragment.

*A. nidulans* amdS gene: The gene has been isolated from *Aspergillus nidulans* VH1-TRSX6. It encodes acetamidase (Hynes et al., "Isolation of genomic clones containing the amdS gene of *Aspergillus nidulans* and their use in the analysis of the structural and regulatory mutations," *Mol. Cell. Biol.* 3: 1430–1439 (1983)). Acetamidase enables the strain to grow by using acetamide as the only nitrogen source and this characteristic was used for selecting the transformants. The 3.1 kb fragment (SpeI-XbaI) from the plasmid p3SP2 (Kelly J. and Hynes M., "Transformation of *Aspergillus niger* by the amdS gene of *Aspergillus nidulans*," EMBO J. 4: 475479 (1985)) is used in the plasmids. The fragment contains 1007 bps of the promoter area, 1897 bps of the coding region (introns included) and the 183 bps terminator area of the amdS gene.

*T. reesei* cbhl 3'-fragment: The fragment was isolated from *T. reesei* ALKO2466 by using plasmid rescue (1.7 kb, BamHI-EcoRI, starting 1.4 kb after the gene's STOP codon, Suominen et al., "High frequency one-step gene replacement in *Trichoderma reesei* II. Effects of deletions of individual cellulase genes," *Mol. Gen Genet.* 241: 523–530 (1993)). Strain ALKO2466 derives from the strain ALKO233 (Harkki et al., "Genetic engineering of Trichoderma to produce strains with novel cellulase profiles," *Enzyme Microb. Technol.* 13: 227–233 (1991)). The 3'-fragment is used together with the promoter area (described above) to target the *T. fusca* xynA gene to the cbhl locus by homologous recombination.

Standard DNA methods were used for construction of the vectors (Sambrook et al., "Molecular Cloning: A Laboratory Manual, 2nd ed. Cold Spring Harbor Laboratory Press, Cold Spring Harbor, N.Y., 1989). The restriction enzymes, T4 DNA ligase, Klenow fragment of the DNA polymerase I, T4 DNA polymerase, polynucleotide kinase and Taq polymerase were from Boehringer (Mannheim, FRG) and New England Biolabs (Beverly, Mass., USA). Each enzyme was used according to the supplier's instructions. Plasmid DNA was isolated by using Qiagen columns (Qiagen GmbH, Dusseldorf, FRG) or Promega Magic Minipreps (Promega, Madison, Wis., USA) according to the manufacturer's protocols. The oligonucleotides used in the PCR-reactions and in sequencing reactions were synthesized by a ABI (Applied Biosystems, Foster City, Calif., USA) 381A DNA Synthesizer. DNA sequencing was done using ABI kits based on fluorescence-labelled primers, or when sequence-specific primers were used, on fluoresence-labelled dideoxynucleotides, by the Taq cycle sequencing method according to the supplier's instructions. Sequencing reactions were analyzed on an ABI 373A sequencer.

DNA fragments for cloning or transformations were isolated from low-melting-point agarose gels (FMC Bioproducts, Rockland, Me., USA) by freeze-thaw-phenol method (Benson, "A rapid procedure for isolating DNA fragments from agarose gels." Biotechniques 2:66–58 1984) or by using the GeneClean® or Mermaid Kits™ (Bio 101 Inc., La Jolla, Calif., USA) according to the supplier's instructions).

T. reesei ALKO2221 was transformed as described by Penttilä et al., "A versatile transformation system for the cellulolytic filamentous fungus Trichoderma reesei," Gene 61: 155–164 (1987)) with the modifications described in Karhunen et al., "High frequency one-step gene replacement in Trichoderma reesei I. Endoglucanase I overproduction," Mol. Gen. Genet 241: 515–522) (1993). T. reesei transformants were transferred on a selective medium and purified through conidia. Transformants were stabilized by growing them on selective slants for two generations prior to sporulating on potato dextrose agar.

The culture supernatants were analyzed by measuring the xylanase activity produced, by running samples on SDS-PAGE and by performing Western blots. Polyclonal antibody against T. fusca xylanase and purified T. fusca xylanase used in the Western blots were obtained from Dr. David Wilson (Cornell University, New York).

The xylanase activity from the culture supernatants was measured as in Bailey et al.,. "Interlaboratory testing of methods for assay of xylanase activity." J. Biotechnol. 23:257–270 (1992), with the modification described below. The supernatants were incubated at 60° C. for 20 hours in 1:5 diluted McIlvain's buffer (stock buffer 0.25 M citric acid—0.5M $Na_2HPO_4$) with 200 μg/ml BSA to destroy T. reesei's own xylanase activity. After the incubation, xylanase activity was measured in McIlvain's buffer at pH 6.5, 60° C. T. fusca supernatant's xylanase activity was unaffected by the 20 hours' incubation used prior to the reaction but the incubation used did destroy host's xylanase activity. The xylanase activity produced by the best pALK193 transformants was about 900 nkat/ml.

The T. fusca xylanase produced by the T. reesei transformants was not detectable on SDS-PAGE but was detected on the Western blots. The amount of the T. fusca xylanase produced by the transformants, based on the estimation from the Western blots where purified T. fusca xylanase was used as a control, was about 50–100 mg/l.

Example 17

T. reesei β-mannanase and Actinomadura Xylanase Fusions

The Trichoderma reesei strains were constructed for Actinomadura flexuosa xylanase production (35 kDa xylanase, AM35). Strains overproduce Actinomadura xylanase and are unable to produce T. reesei's endoglucanase II and cellobiohydrolase I . Such cellulolytic activity-deficient preparations, and the making of same by recombinant DNA methods, are described in U.S. Pat. No. 5,298,405 incorporated herein by reference or Suominen et al., (High frequency one-step gene replacement in Trichoderma reesei II. Effects of deletions of individual cellulase genes," Mol. Gen. Genet. 241: 523–530 (1993)). For the overproduction of Actinomadura xylanase, the AM35 gene was fused to the T. reesei mannanase 1 gene's core/hinge region and the gene fusion was expressed from the strong cbh1 promoter. Different protease cleavage sites were added between the mannanase and xylanase encoding sequences.

The plasmids pALK945, pALK948, pALK1021 and pALK1022 (FIG. 17) that were used in the construction of the Actinomadura xylanase overproducing strains, are otherwise identical to each other, except that the fusion between the man1 core/hinge and AM35 sequences differs (see FIG. 19, and below).

The plasmids pALK945, pALK948, pALK 1021 and pALK 1022 contain the following elements:

(1) the cbh1 (cellobiohydrolase 1) promoter: The promoter is from Trichoderma reesei VTT-D-80133 (Teeri et al., "The molecular cloning of the major cellulase gene from Trichoderma reesei," Bio/Technology 1: 696–699 (1983)). The 2.2 kb EcoRI-SacII fragment (Karhunen et al., "High frequency one-step gene replacement in Trichoderma reesei I. Endoglucanase I overproduction," Mol. Gen. Genet. 241: 515–522 (1993)) was used in the construct. The sequence of the promoter area preceding the ATG was published by Shoemaker et al., "Molecular cloning of exo-cellobiohydrolase from Trichoderma reesei strain L27," Bio/Technology 1: 691–696(1983)). The last 15 nucleotides of the T. reesei L27 cbh1 promoter (the SacII site is underlined) are CCGCGGACTGGCATC (SEQ ID NO:34) (Shoemaker et al. (1983)). The cbh1 promoter from the T. reesei strain VTT-D-80133 has been sequenced in our laboratory, and one nucleotide difference in the DNA sequence was found within the above mentioned region. In the T. reesei strain VTT-D-80133 the sequence preceding the ATG is CCGCGGACTGCGCATC (SEQ ID NO :35) (the SacII site is underlined, the additional cytosine in the DNA sequence is bolded).

The nucleotides missing from the promoter (10 bps after the SacII to the ATG) were added and the exact promoter fusion to the first ATG of the T. reesei man1 (see below) was done by using the PCR (polymerase chain reaction) method. The fusion and the PCR fragment have been sequenced to ensure that no errors occurred during the reaction. The promoter area also serves as a homologous DNA (together with the cbh1 3'-fragment; see below) to target the integration of the transforming DNA into the cbh1 locus.

(2) the man1 gene's core/hinge region: The man1 gene codes for β-mannanase that degrades mannans/glucomannans (Stålbrand et al., "Cloning and expression in Saccharomyces cerevisiae of a Trichoderma reesei β-mannanase gene containing a cellulose binding domain," Appl. Environ. Microbiol. 61: 1090–1097 (1995)). The gene has been isolated from T. reesei QM6a and its sequence is known (Stålbrand et al., 1995). The 1.35 kb DNA fragment from nucleotides 1 to 1347 coding for the man1 core/hinge region (amino acids from 1 to 379) was used in plasmids pALK945 and pALK948. The DNA fragment from nucleotides 1 to 1359 (amino acids 1 to 383) was used in plasmids pALK1021 and pALK1022. The man1 core/hinge region was linked, from its C-terminal end, to the AM35 gene by using the PCR method to obtain four different fusions.

(3) the AM35 gene: The nucleotide sequence (SEQ ID NO:1) and deduced amino acid sequence (SEQ ID NO:2) of the AM35 gene encoding a 35 kDa xylanase is presented in FIG. 13. (Also see U.S. Pat. No. 5,437,992- Bodie et al.) The gene was cloned from a genomic library of Actinomadura (Microtetraspora) flexuosa DSM43186 by using a plate activity assay (Example 9A). A 1.3 kb fragment from nucleotide 542 (the N-terminal Asp) to the MluI site about 250 bps after the end of the gene (pALK1055, FIG. 18) was used in all plasmids. The gene was linked, from its N-terminal end, to the mal core/hinge sequence by using four different fusions.

(4) the mal core/hinge—AM35 fusions: manl core/hinge was fused to the AM35 with or without a KEX-linker sequence. The fusion was done by PCR and the following amino acid sequences were formed (see FIG. 19 for the DNA sequences) (SEQ ID NOS:9, 11, 13 and 15):

manl core/hinge+synthetic sequence+AM35 sequence

| pALK945 | ...PLYGRDTT... | =additional R |
| pALK945 | ...PLYGRDKRDTT... | =KEX2-linker added |
| pALK1021 | ...PLYGQCGGDTT... | =no new amino acids |
| pALK1022 | ...PLYGQCGGRDKRDTT... | =KEX2-linker added |

The fusion sequences were sequenced to ensure that no unwanted alterations had taken place.

The linker sequence used in the plasmid pALK945 has been used in the production of murine anti-2-phenyloxazolone IgG1 antibody from *T. reesei* as a fusion to the cellobiohydrolase I core/hinge region (WO 92/01797; Nyyssönen et al., "Efficient production of antibody fragments by the filamentous fungus *Trichoderma reesei*," *Bio/Technology* 11: 591–595 (1993)). The fusions were cleaved at a low frequency by an extracellular, hitherto uncharacterisized *T. reesei* protease. The cleavage was made after the tyrosine residue in the CBHI linker region, two amino acids before the authentic N-terminus of the heavy chain Fd chain.

The linker sequences in the plasmids pALK948 and pALK1022 carried a synthetic spacer peptide, containing a KEX2-like protein processing signal, preceding the mature Actinomadura xylanase.

(5) the cbhl terminator: The 739 bp AvaII fragment (Karhunen et al., "High frequency one-step gene replacement in *Trichoderma reesei* I. Endoglucanase I overproduction," *Mol Gen. Genet.* 241: 515–522 (1993)) starting 113 bp before the STOP of the cbhl gene was added after the AM35 gene to ensure termination of transcription.

(6) the amdS gene: The gene has been isolated from *Aspergillus nidulans* VH1-TRSX6. It encodes acetamidase (Hynes et al., "Isolation of genomic clones containing the amdS gene of *Aspergillus nidulans* and their use in the analysis of the structural and regulatory mutations," *Mol. Cell. Biol.* 3: 1430–1439 (1983)). Acetamidase enables the strain to grow by using acetamide as the only nitrogen source and this characteristic was used for selecting the transformants. The 3.1 kb fragment (SpeI–XbaI) from the plasmid p3SR2 (Kelly J. and Hynes M., "Transformation of *Aspergillus niger* by the amdS gene of *Aspergillus nidulans*," *EMBO J.* 4: 475–479 (1985)) is used in the plasmids. The fragment contains 1007 bps of the promoter area, 1897 bps of the coding region (introns included) and the 183 bps terminator area of the amdS gene.

(7) the cbhl 3'-fragment: The fragment was isolated from *T. reesei* ALKO2466 by using plasmid rescue (1.7 kb, BamHI-EcoRI, starting 1.4 kb after the gene's STOP codon, Suominen et al., "High frequency one-step gene replacement in *Trichoderma reesei* II. Effects of deletions of individual cellulase genes," *Mol. Gen Genet.* 241: 523–530 (1993)). Strain ALKO2466 derives from the strain ALKO233 (Harkki et al, "Genetic engineering of Trichoderma to produce strains with novel cellulase profiles," *Enzyme Microb. Technol.* 13: 227–233 (1991)). The 3'-fragment is used together with the promoter area (described above) to target the manl-AM35 gene fusion to the cbhl locus by homologous recombination.

Standard DNA methods used in the construction of vectors pALK945, pALK948, pALK1021 and pALK1022 are described in Example 16. The 10.3 kb expression cassette was cut from the vector backbone by EcoRI restriction. The expression cassettes were then isolated, purified and transformed into ALKO3620 as described in Example 16.

In the host strain ALKO3620, the egl2 gene has been replaced by the 3.3 kb XbaI-BglII fragment of the ble gene from *Streptoalloteichus hindustanus* (Mattern et al., "A vector of Aspergillus transformation conferring phleomycin resistance," *Fungal Genet. Newlett*35: . 25 (1988), Drocourt et al., "Cassettes of the *Streptoalloteichus hindustanus* ble gene for transformation of lower and higher eukaryotes to phleomycin resistance," *Nucl. Acids. Res.* 18: 4009 (1990)) using the recombinant DNA methods described in U.S. Pat. No. 5,298,405, incorporated herein by reference.

Example 18

Characteristics of the Actinomadura Xylanase Producing Transformants

The purified amdS transformants were grown in shake flasks in a medium containing 4% whey, 1.5% complex nitrogen source derived from grain, 1.5% $KH_2PO_4$ and 0.5% $(NH_4)_2SO_4$. Cultures were maintained at 30° C. and 250 rpm for 7 days.

The culture supernatants were subjected to SDS-polyacrylamide gel electrophoresis (PAGE). CHBI was detected by Western blotting and immunostaining using a CBHI specific monoclonal antibody (CI-258 (Aho et al., "Monoclonal antibodies against core and cellulose-binding domains of *Trichoderma reesei* cellobiohydrolases I and II and endoglucanase I," *Eur. J. Biochem.* 200: 643–649 (1991)) and the ProtoBlot Western blot AP system (Promega) according to the recommendations of the manufacturer.

The *T. reesei* strains ALKO3620/pALK945/8, ALKO3620/pALK948/27, ALKO3620/pALK1021/4 and ALKO3620/pALK1022/29 do not contain the cbhl gene. The cbhl gene is replaced by the amdS marker gene and the manl-AM35 fusion construct in pALK945, pALK948, pALK1021, pALK1022 expression cassettes. The cbhl gene replacement was verified in Southern hybridisations. The host strain ALKO3620 used in the transformations is deficient of the egl2 gene (replaced by ble gene from *Streptoalloteichus hindustanus* (Mattern et al., 1988, Drocourt et al., 1990). Thus the strains do not produce Trichoderma's cellulase components EGII and CBHI.

The xylanase activities of the CBHI negative transformants were determined as described in Examples 2 and 5. Xylanase activities were measured according to Bailey, M. et al., "Interlaboratory testing of methods for assay of xylanase activity," *J. Biotechnol.* 23: 257–270 (1992) using 1% (w/v) birch xylan (Roth 7500) as a substrate. The assay conditions were either, pH 5.3 and 50° C., with an incubation time of 5 min. in 50 mM $Na_2HPO_4$ buffer (Bailey, M. et al. (1992)) or pH 7 and 70° C., with an incubation time of 5 min. in 1:5 diluted McIlvain's buffer (Stock buffer:0.25 M citric acid—0.5M $Na_2HPO_4$), containing 100 μg/ml. of BSA. One xylanase unit (1 nkat) is defined as the amount of enzyme that produces reducing carbohydrates having a reducing power corresponding to one nmol of xylose in one second from birch xylan under assay conditions. Defining the International Unit as the amount of enzyme that produces one micromole of measured end-products in one minute from polymeric substrate, then 1IU=16.67 nkat. The xylanase activity of one transformant per each transformation is presented in Table 1. The corresponding production levels of the transformants as estimated from the specific activity of purified AM35 xylanase (18.000 BXU/mg at pH 7.0 and 70° C.) are shown on Table 5.

TABLE 5

The xylanase activity and estimated production level of *T. reesei* transformants producing Actinomadura 35 kDa xylanase. The result from one transformant from each fusion is shown.

|  | BXU/ml (pH 5.3, 50° C.) | BXU/ml (pH 7.0, 70° C.) | AM35 xylanase g/l (estimate) |
|---|---|---|---|
| Actinomadura culture medium |  | 440 | — |
| ALKO3620 | 3,564 | 356 | — |
| ALKO3620/ pALK945/8 | 10,974 | 14,971 | 0.83 |
| ALKO3620/ pALK948/27 | 6,693 | 11,924 | 0.66 |
| ALKO3620/ pALK1021/4 | 8,398 | 9,797 | 0.54 |
| ALKO3620/ pALK1022/29 | 7,935 | 14,866 | 0.83 |

The xylanase activity of the *T. reesei* host strain ALKO3620 is about ten times lower at optimum conditions for the AM35 protein (pH 7 and 70° C.) than it is under the conditions optimal for the *T. reesei* xylanase (pH 5.3, 50° C.). The lowest activity and production level was obtained with a transformant containing a fusion construct without any protease processing site (ALKO3620/pALK1021/4).

For the thermal stability determination, samples from the culture supernatants were diluted in McIlvain's buffers. BSA was added as carrier protein to a concentration of 100 μg/ml. The xylanase activity was measured by incubating the enzyme samples at 70° C., pH 7.0 for a period of 0, 15, 30 and 120 min. after which the xylanase activity of the samples was determined at pH 7, 70° C., in a 5 min. reaction. The results are shown in FIG. 20. The thermal stability of the AM35 protein produced by recombinant *T. reesei* strains transformed with the pALK945 and pALK1022 plasmids was identical with Actinomadura xylanase. The AM35 protein produced by pALK948 and pALK1021 transformants was less stable (FIG. 20).

Samples from the culture supernatants were run on polyacrylamide slab gels containing 0.1% SDS on Bio-Rad Mini Protean II electrophoresis system. A polyclonal antibody prepared against the purified β-mannanase (pI 5.4) of *T. reesei* RutC30 (Stålbrand et al., "Cloning and expression in *Saccharomyce scerevisiae* of a *Trichoderma reesei* β-mannanase gene containing a cellulose binding domain," *Appl. Environ. Microbiol.* 61: 1090–1097 (1995)) was used to detect the mannanase in Western blots. In the detection, Promega's ProtoBlot® AP System was used. The Western result is shown in FIG. 21. The molecular weight of the β-mannanase protein in the culture medium of the host strain ALKO3620 (lanes 4 and 5) and of all the transformants (lanes 6–10) is somewhat larger than that of the purified 53 kDa β-mannanase protein sample (Stålbrand et al., "Purification and characterization of two β-mannanases from *Trichoderma reesei*," *J. Biotechnol.* 29: 229–242 (1993)), lanes 2 and 3. In addition to the native β-mannanase, the transformants ALKO3620/pALK945/8, ALKO3620/pALK948/27 and ALKO3620/pALK1022/29 (lanes 6–9) produce a smaller protein (about 50 kDa) reacts with the polyclonal mannanase antibody. This band represents the shortened mannanase protein obtained from the fusion constructs, and shows that the extracellular proteases have processed the fusion. In the strain ALKO3620/pALK1021/4 (lane 10) two bands with molecular weights of about 60 and 70 kDa are obtained. These bands originate from the unprocessed fusion protein (mannanase+Actinomadura xylanase)

When Actinomycetes xylanase is expressed in *T. reesei* as a fusion of a homologous gene, high production levels of the heterologous protein can be achieved. When Actinomadura AM35 gene was expressed under the cbh1 promoter as a mannanase fusion, the level of xylanase produced was about 500–800 mg/l (Example 18). When *T. fusca* xynA was expressed in *T. reesei* by linking it to the same promoter (cbh1), without a fusion to homologous gene, only 50–100 mg/l of xylanase was produced (Example 16). Homology between the two Actinomycetes xylanases, Actinomadura xylanase AM35 and *T. fusca* xylanase A is 76% at amino acid level.

Example 19

Bleaching Experiments Using the Actinomadura Xylanase Secreted from Trichoderma as a Mannanase Fusion Protein A sequence of bleaching trials was done to determine the usefulness of the Actinomadura xylanase activity secreted from *Trichoderma reesei* as a mannanase fusion protein in TCF (totally chlorine free) bleaching of kraft pulp.

Culture filtrates (Example 18) of three different transformants were added to Finnish oxygen-delignified softwood kraft pulp (kappa number 16) in the amount of 100 nkat/g pulp dry matter. The enzyme treatments were done at pH 7 and 80° C. for one hour at 3.0% pulp consistency. Reference pulp was treated in the same way but without enzyme addition. Bleaching was performed with QP sequence. The chelation (Q) stage was performed by adding EDTA to 0.2% of dry matter and it was carried out at 3.0% consistency at 50° C. for one hour. The peroxide bleaching (P) stage was carried out at 80° C. for three hours. The conditions were the following: consistency 10%, $H_2O_2$ 3.0%, NaOH 3.0%, diethylene triamine pentaacetic acid "(DTPA)", 0.2% and $MgSO_4$ 0.5%. The results are shown in Table 6.

TABLE 6

| Enzyme Treatment | Ref. | ALKO3620/ pALK945/8 | ALKO3620/ pALK948/27 | ALKO3620/ pALK1022/29 |
|---|---|---|---|---|
| Consistency, % | 3 | 3 | 3 | 3 |
| Retention time, h | 1 | 1 | 1 | 1 |
| Enzyme Dosage, nkat/g pulp dry matter | 0 | 100 | 100 | 100 |
| Temperature, ° C. | 80 | 80 | 80 | 80 |
| pH, start/end | 7.1/6.9 | 6.9/6.9 | 7.0/7.0 | 7.0/7.3 |
| Chelation Stage (See conditions in the text) |  |  |  |  |
| Peroxide Bleaching (See conditions in the text) |  |  |  |  |
| Brightness, % | 64.2 | 66.2 | 65.5 | 65.9 |
| Viscosity, ml/g | 840 | 850 | 850 | 870 |
| Peroxide Consumption, % | 2.3 | 2.3 | 2.3 | 2.3 |

The use of Actinomadura xylanase activity-containing culture filtrates of transformants ALKO3620/pALK945/8, ALKO3620 /pALK948/27 and ALKO3620/pALK1022/29 as a pretreatment of pulp in the peroxide bleaching at 80° C. increased the brightness (2 units at its best with the transformant ALKO3620/pALK945/8) obtained without increasing the amount of peroxide that was consumed. Also enzyme treatments did not affect the viscosity of the pulp. Pulp was also treated ith the culture filtrates mentioned above at pH 7 and 70° C. for one hour. The brightness values were similar compared with the values obtained when the enzyme pretreatments were performed at pH 7 and 80° C.

Example 20

Bacterial Protein Expressed in Aspergillus

Either a *T. reesei* β-mannanase and Actinomadura xylanase fusion (See Ex. 17) or an Aspergillus glucomylase and Actinomadura xylanase fusion is prepared. A recombinant vector encoding a xylanase gene is prepared by fusing the xylanase encoding sequence of an Aspergillus secretable protein. The protein is preferably *A. niger* or *A. niger var awamori* glucoamylase; or a domain thereof, such as the secretion signal or the core sequence or such part of the core, which contains signals necessary for secretion of the protein. (Stoffer et al., "Production, purification and characterization of the catalytic domain of glucoamylase from *Aspergillus niger*." Biochem. J. 292:197–202 (1993); Svensson et al., "Structure-Function relationship in amylases, Ed. R. B. Friedman. Biotechnology of Amylodextrin Oligosaccharides. ACS Symposium Serium 458:28–43 (1991); Boel et al., EMBO . 3:1581–1585 (1984).

Fusion proteins can be constructed that contain an N-termial glucoamylase core domain or the core and the hinge domains from the same, fused to the Actinomadura xylanase sequence. The result is a protein that contains N-terminal glucoamylase core or core and hinge regions, and a C-terminal Actinomadura xylanase. The fusion protein contains both the mannanase or glucoamylase and xylanase activities of the various domains as provided in the fusion construct.

Fusion proteins can also be constructed such that the glucoamylase tail or a desired fragment thereof, is included, placed before the Actinomadura xylanase sequence, especially so as to allow use of a nonspecific protease site in the tail as a protease site for the recovery of the xylanase sequence from the expressed fusion protein. Alternatively, fusion proteins can be constructed that provide for a protease site in a linker that is placed before the Actinomadura xylanase, with or without tail sequences.

The expression vector uses a *A. niger* glucoamylase promoter. (Boel et al., *EMBO J.* 3:1581–1585 (1984)). The transformation host may be some *Aspergillus niger* strain (Kelly and Hynes, "Transformation of *Aspergillus niger* by the amds gene from *Aspergillus nidulans. EMBO J.* 4:475479 (1985)) or for example *Aspergillus niger var awamor* strain ATCC 38854. The chosen Aspergillus strain is transformed similar to that described by Kelly and Hynes. (Transformation of Aspergillus niger by the amds gene from *Aspergillus nidulans. EMBO J.* 4:475–479 (1985)).

The Actinomadura xylanase producing transformants are then characterized similar to Example 18 with modification obvious to a person skilled in the art. The culture medium used may be Aspergillus complete medium. (Rowlands et al., *Mol. Gen. Genet.* 126:201–216 (1973).

All references cited herein are incorporated herein by reference. While this invention has been described in detail and with reference to specific embodiments thereof, it will be apparent to one skilled in the art that various changes and modifications could be made therein without departing from the spirit and scope thereof.

---

SEQUENCE LISTING (1) GENERAL INFORMATION:

(iii) NUMBER OF SEQUENCES: 39

(2) INFORMATION FOR SEQ ID NO:1:

(i) SEQUENCE CHARACTERISTICS:
        (A) LENGTH: 1375 base pairs
        (B) TYPE: nucleic acid
        (C) STRANDEDNESS: Not Relevant
        (D) TOPOLOGY: linear (ii) MOLECULE TYPE: DNA (genomic)

(ix) FEATURE:
        (A) NAME/KEY: CDS
        (B) LOCATION: 303..1334

(xi) SEQUENCE DESCRIPTION: SEQ ID NO:1:

```
CCCGGGTATT CATGTGAATG ATTAGCAACA GTTATGTTAC GGAGATATTT CTGAGAGTGT      60

TGACAGGTCG TGAAGTCGGT CCGATACTTT CGAGCTAGCT CCGATAGTTT TCGATACGCC     120

GGCACATCGA GCACGTCGGA CGAGTCACGC GCCACGTCGG TTTTCCGCCG CACGCCGCGC     180

AGAGCGGCCG GAGAACCCCC GCGTGTCCGC GGCATCGGTG CCGGTCCGTC GTTCGCCGCC     240

GACCGCGCGC CGGGTCGCGA CACGCCAGCC CCCATCGGCC CTTCTTCACG AGGAAGCCGT     300
```

```
AC ATG AAC GAA CCC CTC ACC ATC ACG CAG GCC AGG CGC CGC AGA CGC        347
   Met Asn Glu Pro Leu Thr Ile Thr Gln Ala Arg Arg Arg Arg Arg
    1               5                  10                  15

CTC GGC CTC CGG CGC ATC GTC ACC AGT GCC TTC GCC CTG GCA CTC GCC        395
Leu Gly Leu Arg Arg Ile Val Thr Ser Ala Phe Ala Leu Ala Leu Ala
                 20                  25                  30

ATC GCC GGT GCG CTG CTG CCC GGC ACG GCC CAC GCC GAC ACC ACC ATC        443
Ile Ala Gly Ala Leu Leu Pro Gly Thr Ala His Ala Asp Thr Thr Ile
             35                  40                  45

ACC CAG AAC CAG ACC GGG TAC GAC AAC GGC TAC TTC TAC TCG TTC TGG        491
Thr Gln Asn Gln Thr Gly Tyr Asp Asn Gly Tyr Phe Tyr Ser Phe Trp
         50                  55                  60

ACC GAC GCG CCC GGG ACC GTC TCC ATG ACC CTC CAC TCG GGC GGC AGC        539
Thr Asp Ala Pro Gly Thr Val Ser Met Thr Leu His Ser Gly Gly Ser
     65                  70                  75

TAC AGC ACC TCG TGG CGG AAC ACC GGG AAC TTC GTC GCC GGC AAG GGC        587
Tyr Ser Thr Ser Trp Arg Asn Thr Gly Asn Phe Val Ala Gly Lys Gly
 80                  85                  90                  95

TGG TCC ACC GGG GGA CGG CGG ACC GTG ACC TAC AAC GCC TCC TTC AAC        635
Trp Ser Thr Gly Gly Arg Arg Thr Val Thr Tyr Asn Ala Ser Phe Asn
                100                 105                 110

CCG TCG GGT AAC GGC TAC CTC ACG CTC TAC GGC TGG ACC AGG AAC CCG        683
Pro Ser Gly Asn Gly Tyr Leu Thr Leu Tyr Gly Trp Thr Arg Asn Pro
             115                 120                 125

CTC GTC GAG TAC TAC ATC GTC GAG AGC TGG GGC ACC TAC CGG CCC ACC        731
Leu Val Glu Tyr Tyr Ile Val Glu Ser Trp Gly Thr Tyr Arg Pro Thr
         130                 135                 140

GGC ACC TAC AAG GGC ACC GTC ACC ACC GAC GGG GGA ACG TAC GAC ATC        779
Gly Thr Tyr Lys Gly Thr Val Thr Thr Asp Gly Gly Thr Tyr Asp Ile
    145                 150                 155

TAC GAG ACC TGG CGG TAC AAC GCG CCG TCC ATC GAG GGC ACC CGG ACC        827
Tyr Glu Thr Trp Arg Tyr Asn Ala Pro Ser Ile Glu Gly Thr Arg Thr
160                 165                 170                 175

TTC CAG CAG TTC TGG AGC GTC CGG CAG CAG AAG CGG ACC AGC GGC ACC        875
Phe Gln Gln Phe Trp Ser Val Arg Gln Gln Lys Arg Thr Ser Gly Thr
                180                 185                 190

ATC ACC ATC GGC AAC CAC TTC GAC GCC TGG GCC CGC GCC GGC ATG AAC        923
Ile Thr Ile Gly Asn His Phe Asp Ala Trp Ala Arg Ala Gly Met Asn
             195                 200                 205

CTG GGC AGC CAC GAC TAC CAG ATC ATG GCG ACC GAG GGC TAC CAG AGC        971
Leu Gly Ser His Asp Tyr Gln Ile Met Ala Thr Glu Gly Tyr Gln Ser
         210                 215                 220

AGC GGT AGC TCC ACC GTC TCC ATC AGC GAG GGT GGC AAC CCC GGC AAC       1019
Ser Gly Ser Ser Thr Val Ser Ile Ser Glu Gly Gly Asn Pro Gly Asn
    225                 230                 235

CCG GGT AAC CCC GGC AAC CCC GGC AAC CCC GGT AAC CCG GGT AAC CCC       1067
Pro Gly Asn Pro Gly Asn Pro Gly Asn Pro Gly Asn Pro Gly Asn Pro
240                 245                 250                 255

GGC GGT GGC TGC GTC GCG ACC CTC TCC GCC GGC CAG CAG TGG AGC GAC       1115
Gly Gly Gly Cys Val Ala Thr Leu Ser Ala Gly Gln Gln Trp Ser Asp
                260                 265                 270

CGC TAC AAC CTC AAC GTC TCG GTC AGC GGC TCG AAC AAC TGG ACG GTC       1163
Arg Tyr Asn Leu Asn Val Ser Val Ser Gly Ser Asn Asn Trp Thr Val
             275                 280                 285

CGG ATG GAC GTG CCC TAC CCG GCC CGC ATC ATC GCC ACC TGG AAC ATC       1211
Arg Met Asp Val Pro Tyr Pro Ala Arg Ile Ile Ala Thr Trp Asn Ile
         290                 295                 300

CAC GCC CAG TGG CCC GAG TCC CAG GTG CTC ATC GCC AGA CCC AAC GGC       1259
His Ala Gln Trp Pro Glu Ser Gln Val Leu Ile Ala Arg Pro Asn Gly
```

```
              305                 310                 315
AAC GGC AAC AAC TGG GGC GTG ACG ATC CAG CAC AAC GGC AAC TGG ACC      1307
Asn Gly Asn Asn Trp Gly Val Thr Ile Gln His Asn Gly Asn Trp Thr
320                 325                 330                 335

TGG CCG ACG GTC ACC TGT ACC GCG AAC TGAGTTCCCG CCCCCAAAGG            1354
Trp Pro Thr Val Thr Cys Thr Ala Asn
                340

TGGCGCGGCG GCTCCCGGCC G                                              1375
```

(2) INFORMATION FOR SEQ ID NO:2:

(i) SEQUENCE CHARACTERISTICS:
        (A) LENGTH: 344 amino acids
        (B) TYPE: amino acid
        (D) TOPOLOGY: linear (ii) MOLECULE TYPE: protein (xi) SEQUENCE DESCRIPTION: SEQ ID NO:2:

```
Met Asn Glu Pro Leu Thr Ile Thr Gln Ala Arg Arg Arg Arg Arg Leu
 1               5                  10                  15

Gly Leu Arg Arg Ile Val Thr Ser Ala Phe Ala Leu Ala Leu Ala Ile
                20                  25                  30

Ala Gly Ala Leu Leu Pro Gly Thr Ala His Ala Asp Thr Thr Ile Thr
            35                  40                  45

Gln Asn Gln Thr Gly Tyr Asp Asn Gly Tyr Phe Tyr Ser Phe Trp Thr
    50                  55                  60

Asp Ala Pro Gly Thr Val Ser Met Thr Leu His Ser Gly Gly Ser Tyr
65                  70                  75                  80

Ser Thr Ser Trp Arg Asn Thr Gly Asn Phe Val Ala Gly Lys Gly Trp
                85                  90                  95

Ser Thr Gly Gly Arg Arg Thr Val Thr Tyr Asn Ala Ser Phe Asn Pro
            100                 105                 110

Ser Gly Asn Gly Tyr Leu Thr Leu Tyr Gly Trp Thr Arg Asn Pro Leu
    115                 120                 125

Val Glu Tyr Tyr Ile Val Glu Ser Trp Gly Thr Tyr Arg Pro Thr Gly
130                 135                 140

Thr Tyr Lys Gly Thr Val Thr Thr Asp Gly Gly Thr Tyr Asp Ile Tyr
145                 150                 155                 160

Glu Thr Trp Arg Tyr Asn Ala Pro Ser Ile Glu Gly Thr Arg Thr Phe
                165                 170                 175

Gln Gln Phe Trp Ser Val Arg Gln Gln Lys Arg Thr Ser Gly Thr Ile
            180                 185                 190

Thr Ile Gly Asn His Phe Asp Ala Trp Ala Arg Ala Gly Met Asn Leu
    195                 200                 205

Gly Ser His Asp Tyr Gln Ile Met Ala Thr Glu Gly Tyr Gln Ser Ser
210                 215                 220

Gly Ser Ser Thr Val Ser Ile Ser Glu Gly Asn Pro Gly Asn Pro
225                 230                 235                 240

Gly Asn Pro Gly Asn Pro Gly Asn Pro Gly Asn Pro Gly
                245                 250                 255

Gly Gly Cys Val Ala Thr Leu Ser Ala Gly Gln Gln Trp Ser Asp Arg
            260                 265                 270

Tyr Asn Leu Asn Val Ser Val Ser Gly Ser Asn Asn Trp Thr Val Arg
    275                 280                 285

Met Asp Val Pro Tyr Pro Ala Arg Ile Ile Ala Thr Trp Asn Ile His
```

```
                        290                 295                 300
Ala Gln Trp Pro Glu Ser Gln Val Leu Ile Ala Arg Pro Asn Gly Asn
305                 310                 315                 320

Gly Asn Asn Trp Gly Val Thr Ile Gln His Asn Gly Asn Trp Thr Trp
                325                 330                 335

Pro Thr Val Thr Cys Thr Ala Asn
            340

(2) INFORMATION FOR SEQ ID NO:3:

(i) SEQUENCE CHARACTERISTICS:
        (A) LENGTH: 1864 base pairs
        (B) TYPE: nucleic acid
        (C) STRANDEDNESS: Not Relevant
        (D) TOPOLOGY: Not Relevant (ii) MOLECULE TYPE: DNA (genomic)

(vi) ORIGINAL SOURCE:
        (A) ORGANISM: Actinomadura
        (B) STRAIN: DSM43186

(ix) FEATURE:
        (A) NAME/KEY: CDS
        (B) LOCATION: 194..1669

(xi) SEQUENCE DESCRIPTION: SEQ ID NO:3:

TTCGGCAGCC TATTGACAAA TTTCGTGAAT GTTTCCCACA CTTGCTCTGC AGACGGCCCC      60

GCCGATCATG GGTGCACCGG TCGGCGGGAC CGTGCTCCGA CGCCATTCGG GGGTGTGCGC     120

CTGCGGGCGC GGCGTCGATC CCGCGGGGAC TCCCGCGGTT CCCTTTCCGT GTCCCTCTAA    180
```

TGGAGGCTCA GGC ATG GGC GTG AAC GCC TTC CCC AGA CCC GGA GCT CGG         229
               Met Gly Val Asn Ala Phe Pro Arg Pro Gly Ala Arg
                345                 350                 355

CGG TTC ACC GGC GGG CTG TAC CGG GCC CTG GCC GCG GCC ACG GTG AGC       277
Arg Phe Thr Gly Gly Leu Tyr Arg Ala Leu Ala Ala Ala Thr Val Ser
            360                 365                 370

GTG GTC GGC GTG GTC ACG GCC CTG ACG GTG ACC CAG CCC GCC AGC GCC       325
Val Val Gly Val Val Thr Ala Leu Thr Val Thr Gln Pro Ala Ser Ala
        375                 380                 385

GCG GCG AGC ACG CTC GCC GAG GGT GCC GCG CAG CAC AAC CGG TAC TTC       373
Ala Ala Ser Thr Leu Ala Glu Gly Ala Ala Gln His Asn Arg Tyr Phe
    390                 395                 400

GGC GTG GCC ATC GCC GCG AAC AGG CTC ACC GAC TCG GTC TAC ACC AAC       421
Gly Val Ala Ile Ala Ala Asn Arg Leu Thr Asp Ser Val Tyr Thr Asn
405                 410                 415                 420

ATC GCG AAC CGC GAG TTC AAC TCG GTG ACG GCC GAG AAC GAG ATG AAG       469
Ile Ala Asn Arg Glu Phe Asn Ser Val Thr Ala Glu Asn Glu Met Lys
                425                 430                 435

ATC GAC GCC ACC GAG CCG CAG CAG GGG CGG TTC GAC TTC ACC CAG GCC       517
Ile Asp Ala Thr Glu Pro Gln Gln Gly Arg Phe Asp Phe Thr Gln Ala
            440                 445                 450

GAC CGG ATC TAC AAC TGG GCG CGC CAG AAC GGC AAG CAG GTC CGC GGC       565
Asp Arg Ile Tyr Asn Trp Ala Arg Gln Asn Gly Lys Gln Val Arg Gly
        455                 460                 465

CAC ACC CTG GCC TGG CAC TCG CAG CAG CCG CAG TGG ATG CAG AAC CTC       613
His Thr Leu Ala Trp His Ser Gln Gln Pro Gln Trp Met Gln Asn Leu
    470                 475                 480

AGC GGC CAG GCC CTG CGC CAG GCG ATG ATC AAC CAC ATC CAG GGG GTC       661
Ser Gly Gln Ala Leu Arg Gln Ala Met Ile Asn His Ile Gln Gly Val
485                 490                 495                 500

ATG TCC TAC TAC CGG GGC AAG ATC CCG ATC TGG GAC GTG GTG AAC GAG       709

```
                                          -continued

Met Ser Tyr Tyr Arg Gly Lys Ile Pro Ile Trp Asp Val Val Asn Glu
            505                 510                 515

GCG TTC GAG GAC GGA AAC TCC GGC CGC CGG TGC GAC TCC AAC CTC CAG       757
Ala Phe Glu Asp Gly Asn Ser Gly Arg Arg Cys Asp Ser Asn Leu Gln
            520                 525                 530

CGC ACC GGT AAC GAT TGG ATC GAG GTC GCG TTC CGC ACC GCC CGC CAG       805
Arg Thr Gly Asn Asp Trp Ile Glu Val Ala Phe Arg Thr Ala Arg Gln
            535                 540                 545

GGG GAC CCC TCG GCC AAG CTC TGC TAC AAC GAC TAC AAC ATC GAG AAC       853
Gly Asp Pro Ser Ala Lys Leu Cys Tyr Asn Asp Tyr Asn Ile Glu Asn
        550                 555                 560

TGG AAC GCG GCC AAG ACC CAG GCG GTC TAC AAC ATG GTG CGG GAC TTC       901
Trp Asn Ala Ala Lys Thr Gln Ala Val Tyr Asn Met Val Arg Asp Phe
565                 570                 575                 580

AAG TCC CGC GGC GTG CCC ATC GAC TGC GTG GGC TTC CAG TCG CAC TTC       949
Lys Ser Arg Gly Val Pro Ile Asp Cys Val Gly Phe Gln Ser His Phe
                585                 590                 595

AAC AGC GGT AAC CCG TAC AAC CCG AAC TTC CGC ACC ACC CTG CAG CAG       997
Asn Ser Gly Asn Pro Tyr Asn Pro Asn Phe Arg Thr Thr Leu Gln Gln
            600                 605                 610

TTC GCG GCC CTC GGC GTG GAC GTC GAG GTC ACC GAG CTG GAC ATC GAG      1045
Phe Ala Ala Leu Gly Val Asp Val Glu Val Thr Glu Leu Asp Ile Glu
            615                 620                 625

AAC GCC CCG GCC CAG ACC TAC GCC AGC GTG ATC CGG GAC TGC CTG GCC      1093
Asn Ala Pro Ala Gln Thr Tyr Ala Ser Val Ile Arg Asp Cys Leu Ala
        630                 635                 640

GTG GAC CGC TGC ACC GGC ATC ACC GTC TGG GGT GTC CGC GAC AGC GAC      1141
Val Asp Arg Cys Thr Gly Ile Thr Val Trp Gly Val Arg Asp Ser Asp
645                 650                 655                 660

TCC TGG CGC TCG TAC CAG AAC CCG CTG CTG TTC GAC AAC AAC GGC AAC      1189
Ser Trp Arg Ser Tyr Gln Asn Pro Leu Leu Phe Asp Asn Asn Gly Asn
                665                 670                 675

AAG AAG CAG GCC TAC TAC GCG GTG CTC GAC GCC CTG AAC GAG GGC TCC      1237
Lys Lys Gln Ala Tyr Tyr Ala Val Leu Asp Ala Leu Asn Glu Gly Ser
            680                 685                 690

GAC GAC GGT GGC GGC CCG TCC AAC CCG CCG GTC TCG CCG CCG CCG GGT      1285
Asp Asp Gly Gly Gly Pro Ser Asn Pro Pro Val Ser Pro Pro Pro Gly
            695                 700                 705

GGC GGT TCC GGG CAG ATC CGG GGC GTG GCC TCC AAC CGG TGC ATC GAC      1333
Gly Gly Ser Gly Gln Ile Arg Gly Val Ala Ser Asn Arg Cys Ile Asp
710                 715                 720

GTG CCG AAC GGC AAC ACC GCC GAC GGC ACC CAG GTC CAG CTG TAC GAC      1381
Val Pro Asn Gly Asn Thr Ala Asp Gly Thr Gln Val Gln Leu Tyr Asp
725                 730                 735                 740

TGC CAC AGC GGT TCC AAC CAG CAG TGG ACC TAC ACC TCG TCC GGT GAG      1429
Cys His Ser Gly Ser Asn Gln Gln Trp Thr Tyr Thr Ser Ser Gly Glu
                745                 750                 755

TTC CGC ATC TTC GGC AAC AAG TGC CTG GAC GCG GGC GGC TCC AGC AAC      1477
Phe Arg Ile Phe Gly Asn Lys Cys Leu Asp Ala Gly Gly Ser Ser Asn
            760                 765                 770

GGT GCG GTG GTC CAG ATC TAC AGC TGC TGG GGC GGC GCC AAC CAG AAG      1525
Gly Ala Val Val Gln Ile Tyr Ser Cys Trp Gly Gly Ala Asn Gln Lys
            775                 780                 785

TGG GAG CTC CGG GCC GAC GGC ACC ATC GTG GGC GTG CAG TCC GGG CTG      1573
Trp Glu Leu Arg Ala Asp Gly Thr Ile Val Gly Val Gln Ser Gly Leu
            790                 795                 800

TGC CTC GAC GCG GTG GGT GGC GGC ACC GGC AAC GGC ACG CGG CTG CAG      1621
Cys Leu Asp Ala Val Gly Gly Gly Thr Gly Asn Gly Thr Arg Leu Gln
805                 810                 815                 820
```

```
CTC TAC TCC TGC TGG GGC GGC AAC AAC CAG AAG TGG TCC TAC AAC GCC    1669
Leu Tyr Ser Cys Trp Gly Gly Asn Asn Gln Lys Trp Ser Tyr Asn Ala
                825                 830                 835

TGATCCCCGG CTGATCGACC CTAGTTGAGG CCGTCTCCGG TACGGCACCG TCGGACCGGA   1729

GGCGGTCCCT TGTTCGTCCA GGACGGAAGG ACCGGTCTGA GCAGGCGCGG CGATCGGACA   1789

CCATGGTGGG AGGCACGAAA GCGGAGGGG GTCGTATTCC GAGACTCCGG GAAGTGGAGG    1849

TGTTCCTCCA CCTGA                                                    1864

(2) INFORMATION FOR SEQ ID NO:4:

(i) SEQUENCE CHARACTERISTICS:
        (A) LENGTH: 492 amino acids
        (B) TYPE: amino acid
        (D) TOPOLOGY: linear (ii) MOLECULE TYPE: protein (xi) SEQUENCE DESCRIPTION: SEQ ID NO:4:

Met Gly Val Asn Ala Phe Pro Arg Pro Gly Ala Arg Arg Phe Thr Gly
  1               5                  10                  15

Gly Leu Tyr Arg Ala Leu Ala Ala Ala Thr Val Ser Val Val Gly Val
                 20                  25                  30

Val Thr Ala Leu Thr Val Thr Gln Pro Ala Ser Ala Ala Ala Ser Thr
             35                  40                  45

Leu Ala Glu Gly Ala Ala Gln His Asn Arg Tyr Phe Gly Val Ala Ile
         50                  55                  60

Ala Ala Asn Arg Leu Thr Asp Ser Val Tyr Thr Asn Ile Ala Asn Arg
 65                  70                  75                  80

Glu Phe Asn Ser Val Thr Ala Glu Asn Glu Met Lys Ile Asp Ala Thr
                 85                  90                  95

Glu Pro Gln Gln Gly Arg Phe Asp Phe Thr Gln Ala Asp Arg Ile Tyr
                100                 105                 110

Asn Trp Ala Arg Gln Asn Gly Lys Gln Val Arg Gly His Thr Leu Ala
            115                 120                 125

Trp His Ser Gln Gln Pro Gln Trp Met Gln Asn Leu Ser Gly Gln Ala
        130                 135                 140

Leu Arg Gln Ala Met Ile Asn His Ile Gln Gly Val Met Ser Tyr Tyr
145                 150                 155                 160

Arg Gly Lys Ile Pro Ile Trp Asp Val Val Asn Glu Ala Phe Glu Asp
                165                 170                 175

Gly Asn Ser Gly Arg Arg Cys Asp Ser Asn Leu Gln Arg Thr Gly Asn
            180                 185                 190

Asp Trp Ile Glu Val Ala Phe Arg Thr Ala Arg Gln Gly Asp Pro Ser
        195                 200                 205

Ala Lys Leu Cys Tyr Asn Asp Tyr Asn Ile Glu Asn Trp Asn Ala Ala
    210                 215                 220

Lys Thr Gln Ala Val Tyr Asn Met Val Arg Asp Phe Lys Ser Arg Gly
225                 230                 235                 240

Val Pro Ile Asp Cys Val Gly Phe Gln Ser His Phe Asn Ser Gly Asn
                245                 250                 255

Pro Tyr Asn Pro Asn Phe Arg Thr Thr Leu Gln Gln Phe Ala Ala Leu
            260                 265                 270

Gly Val Asp Val Glu Val Thr Glu Leu Asp Ile Glu Asn Ala Pro Ala
        275                 280                 285

Gln Thr Tyr Ala Ser Val Ile Arg Asp Cys Leu Ala Val Asp Arg Cys
```

```
            290                 295                 300
Thr Gly Ile Thr Val Trp Gly Val Arg Asp Ser Asp Ser Trp Arg Ser
305                 310                 315                 320

Tyr Gln Asn Pro Leu Leu Phe Asp Asn Asn Gly Asn Lys Lys Gln Ala
                325                 330                 335

Tyr Tyr Ala Val Leu Asp Ala Leu Asn Glu Gly Ser Asp Asp Gly Gly
                340                 345                 350

Gly Pro Ser Asn Pro Pro Val Ser Pro Pro Gly Gly Gly Ser Gly
                355                 360                 365

Gln Ile Arg Gly Val Ala Ser Asn Arg Cys Ile Asp Val Pro Asn Gly
370                 375                 380

Asn Thr Ala Asp Gly Thr Gln Val Gln Leu Tyr Asp Cys His Ser Gly
385                 390                 395                 400

Ser Asn Gln Gln Trp Thr Tyr Thr Ser Ser Gly Glu Phe Arg Ile Phe
                405                 410                 415

Gly Asn Lys Cys Leu Asp Ala Gly Gly Ser Ser Asn Gly Ala Val Val
                420                 425                 430

Gln Ile Tyr Ser Cys Trp Gly Gly Ala Asn Gln Lys Trp Glu Leu Arg
                435                 440                 445

Ala Asp Gly Thr Ile Val Gly Val Gln Ser Gly Leu Cys Leu Asp Ala
450                 455                 460

Val Gly Gly Gly Thr Gly Asn Gly Thr Arg Leu Gln Leu Tyr Ser Cys
465                 470                 475                 480

Trp Gly Gly Asn Asn Gln Lys Trp Ser Tyr Asn Ala
                485                 490
```

(2) INFORMATION FOR SEQ ID NO:5:

(i) SEQUENCE CHARACTERISTICS:
       (A) LENGTH: 480 amino acids
       (B) TYPE: amino acid
       (C) STRANDEDNESS: Not Relevant
       (D) TOPOLOGY: linear (ii) MOLECULE TYPE: peptide (viii) POSITION IN GENOME:
       (A) CHROMOSOME/SEGMENT: AM50

(xi) SEQUENCE DESCRIPTION: SEQ ID NO:5:

```
Met Gly Val Asn Ala Phe Pro Arg Pro Gly Ala Arg Arg Phe Thr Gly
1               5                   10                  15

Gly Leu Tyr Arg Ala Leu Ala Ala Thr Val Ser Val Val Gly Val
                20                  25                  30

Val Thr Ala Leu Thr Val Thr Gln Pro Ala Ser Ala Ala Ala Ser Thr
                35                  40                  45

Leu Ala Glu Gly Ala Ala Gln His Asn Arg Tyr Phe Gly Val Ala Ile
            50                  55                  60

Ala Ala Asn Arg Leu Thr Asp Ser Val Tyr Thr Asn Ile Ala Asn Arg
65                  70                  75                  80

Glu Phe Asn Ser Val Thr Ala Glu Asn Glu Met Lys Ile Asp Ala Thr
                85                  90                  95

Glu Pro Gln Gln Gly Arg Phe Asp Phe Thr Gln Ala Asp Arg Ile Tyr
                100                 105                 110

Asn Trp Ala Arg Gln Asn Gly Lys Gln Val Arg Gly His Thr Leu Ala
                115                 120                 125

Trp His Ser Gln Gln Pro Gln Trp Met Gln Asn Leu Ser Gly Gln Ala
```

```
                130                 135                 140
Leu Arg Gln Ala Met Ile Asn His Ile Gln Gly Val Met Ser Tyr Tyr
145                 150                 155                 160

Arg Gly Lys Ile Pro Ile Trp Asp Val Val Asn Glu Ala Phe Glu Asp
                165                 170                 175

Gly Asn Ser Gly Arg Arg Cys Asp Ser Asn Leu Gln Arg Thr Gly Asn
                180                 185                 190

Asp Trp Ile Glu Val Ala Phe Arg Thr Ala Arg Gln Gly Asp Pro Ser
                195                 200                 205

Ala Lys Leu Cys Tyr Asn Asp Tyr Asn Ile Glu Asn Trp Asn Ala Ala
210                 215                 220

Lys Thr Gln Ala Val Tyr Asn Met Val Arg Asp Phe Lys Ser Arg Gly
225                 230                 235                 240

Val Pro Ile Asp Cys Val Gly Phe Gln Ser His Phe Asn Ser Gly Asn
                245                 250                 255

Pro Tyr Asn Pro Asn Phe Arg Thr Thr Leu Gln Gln Phe Ala Ala Leu
                260                 265                 270

Gly Val Asp Val Glu Val Thr Glu Leu Asp Ile Glu Asn Ala Pro Ala
                275                 280                 285

Gln Thr Tyr Ala Ser Val Ile Arg Asp Cys Leu Ala Val Asp Arg Cys
290                 295                 300

Thr Gly Ile Thr Val Trp Gly Val Arg Asp Ser Asp Ser Trp Arg Ser
305                 310                 315                 320

Tyr Gln Asn Pro Leu Leu Phe Asp Asn Asn Gly Asn Lys Lys Gln Ala
                325                 330                 335

Tyr Tyr Ala Val Leu Asp Ala Leu Asn Glu Gly Ser Asp Asp Gly Gly
                340                 345                 350

Gly Pro Ser Asn Pro Pro Val Ser Pro Pro Gly Gly Gly Ser Gly
                355                 360                 365

Gln Ile Arg Gly Val Ala Ser Asn Arg Cys Ile Asp Val Pro Asn Gly
370                 375                 380

Asn Thr Ala Asp Gly Thr Gln Val Gln Leu Tyr Asp Cys His Ser Gly
385                 390                 395                 400

Ser Asn Gln Gln Trp Thr Tyr Thr Ser Ser Gly Glu Phe Arg Ile Phe
                405                 410                 415

Gly Asn Lys Cys Leu Asp Ala Gly Ser Ser Asn Gly Ala Val Val
                420                 425                 430

Gln Ile Tyr Ser Cys Trp Gly Gly Ala Asn Gln Lys Trp Glu Leu Arg
                435                 440                 445

Ala Asp Gly Thr Ile Val Gly Val Gln Ser Gly Leu Cys Leu Asp Ala
                450                 455                 460

Val Gly Gly Gly Thr Gly Asn Gly Thr Arg Leu Gln Leu Tyr Ser Cys
465                 470                 475                 480

(2) INFORMATION FOR SEQ ID NO:6:

(i) SEQUENCE CHARACTERISTICS:
        (A) LENGTH: 434 amino acids
        (B) TYPE: amino acid
        (C) STRANDEDNESS: Not Relevant
        (D) TOPOLOGY: linear (ii) MOLECULE TYPE: peptide (viii) POSITION IN GENOME:
        (A) CHROMOSOME/SEGMENT: U08894
```

(xi) SEQUENCE DESCRIPTION: SEQ ID NO:6:

```
Met Pro Ile Asn Val Met Pro Arg Pro Gly Ala Arg Lys Xaa Xaa Xaa
  1               5                  10                  15

Xaa Xaa Xaa Arg Ala Leu Leu Ala Gly Ala Val Gly Leu Leu Thr Ala
             20                  25                  30

Ala Ala Ala Leu Val Ala Pro Ser Pro Ala Val Ala Ala Glu Ser Thr
         35                  40                  45

Leu Gly Ala Ala Ala Ala Gln Ser Gly Arg Tyr Phe Gly Thr Ala Ile
     50                  55                  60

Ala Ser Gly Arg Leu Asn Asp Ser Thr Tyr Thr Thr Ile Ala Asn Arg
 65                  70                  75                  80

Glu Phe Asn Met Val Thr Ala Glu Asn Glu Met Lys Ile Asp Ala Thr
                 85                  90                  95

Glu Pro Asn Arg Gly Gln Phe Asn Phe Ser Ser Ala Asp Arg Ile Tyr
            100                 105                 110

Asn Trp Ala Val Gln Asn Gly Lys Gln Val Arg Gly His Thr Leu Ala
        115                 120                 125

Trp His Ser Gln Gln Pro Gly Trp Met Gln Ser Leu Ser Gly Ser Ser
    130                 135                 140

Leu Arg Gln Ala Met Ile Asp His Ile Asn Gly Val Met Ala His Tyr
145                 150                 155                 160

Lys Gly Lys Ile Val Gln Trp Asp Val Val Asn Glu Ala Phe Ala Asp
                165                 170                 175

Gly Asn Ser Gly Gly Arg Arg Asp Ser Asn Leu Gln Arg Thr Gly Asn
            180                 185                 190

Asp Trp Ile Glu Val Ala Phe Arg Thr Ala Arg Asn Ala Asp Pro Asn
        195                 200                 205

Ala Lys Leu Cys Tyr Asn Asp Tyr Asn Ile Glu Asn Trp Asn Trp Ala
    210                 215                 220

Lys Thr Gln Gly Val Tyr Met Asn Val Arg Asp Phe Lys Gln Arg Gly
225                 230                 235                 240

Val Pro Ile Asp Cys Val Gly Phe Gln Ser His Phe Asn Ser Gly Ser
                245                 250                 255

Pro Tyr Asn Ser Asn Phe Arg Thr Thr Leu Gln Asn Phe Ala Ala Leu
            260                 265                 270

Gly Val Asp Val Ala Ile Thr Glu Leu Asp Ile Gln Gly Ala Ser Pro
        275                 280                 285

Thr Thr Tyr Ala Asn Val Val Asn Asp Cys Leu Ala Val Ser Arg Cys
290                 295                 300

Leu Gly Ile Thr Val Trp Gly Val Arg Asp Thr Asp Ser Trp Arg Ser
305                 310                 315                 320

Asp Gln Thr Pro Leu Leu Phe Asp Gly Asn Gly Asn Lys Lys Ala Ala
                325                 330                 335

Tyr Ser Ala Val Leu Asn Ala Leu Xaa Xaa Xaa Xaa Asn Gly Gly
            340                 345                 350

Gly Thr Ser Glu Xaa Xaa Xaa Pro Pro Ala Ser Asp Ala Gly
        355                 360                 365

Thr Ile Lys Gly Val Gly Ser Gly Arg Cys Leu Asp Val Pro Asn Ala
370                 375                 380

Ser Thr Ser Asp Gly Val Gln Leu Gln Leu Trp Asp Cys His Gly Gly
385                 390                 395                 400

Thr Asn Gln Gln Trp Thr Tyr Thr Asp Ser Gln Glu Leu Arg Val Tyr
                405                 410                 415
```

```
Gly Asn Lys Cys Leu Asp Ala Ala Gly Thr Gly Asn Gly Thr Lys Val
            420                 425                 430

Gln Ile
```

(2) INFORMATION FOR SEQ ID NO:7:

(i) SEQUENCE CHARACTERISTICS:
        (A) LENGTH: 492 amino acids
        (B) TYPE: amino acid
        (C) STRANDEDNESS: Not Relevant
        (D) TOPOLOGY: linear (ii) MOLECULE TYPE: peptide (viii) POSITION IN GENOME:
        (A) CHROMOSOME/SEGMENT: AM50

(xi) SEQUENCE DESCRIPTION: SEQ ID NO:7:

```
Met Gly Val Asn Ala Phe Pro Arg Pro Gly Ala Arg Arg Phe Thr Gly
1               5                   10                  15

Gly Leu Tyr Arg Ala Leu Ala Ala Thr Val Ser Val Val Gly Val
            20                  25                  30

Val Thr Ala Leu Thr Val Thr Gln Pro Ala Ser Ala Ala Ser Thr
        35                  40                  45

Leu Ala Glu Gly Ala Ala Gln His Asn Arg Tyr Phe Gly Val Ala Ile
50                  55                  60

Ala Ala Asn Arg Leu Thr Asp Ser Val Tyr Thr Asn Ile Ala Asn Arg
65                  70                  75                  80

Glu Phe Asn Ser Val Thr Ala Glu Asn Glu Met Lys Ile Asp Ala Thr
                85                  90                  95

Glu Pro Gln Gln Gly Arg Phe Asp Phe Thr Gln Ala Asp Arg Ile Tyr
            100                 105                 110

Asn Trp Ala Arg Gln Asn Gly Lys Gln Val Arg Gly His Thr Leu Ala
            115                 120                 125

Trp His Ser Gln Gln Pro Gln Trp Met Gln Asn Leu Ser Gly Gln Ala
130                 135                 140

Leu Arg Gln Ala Met Ile Asn His Ile Gln Gly Val Met Ser Tyr Tyr
145                 150                 155                 160

Arg Gly Lys Ile Pro Ile Trp Asp Val Val Asn Glu Ala Phe Glu Asp
            165                 170                 175

Gly Asn Ser Gly Arg Arg Cys Asp Ser Asn Leu Gln Arg Thr Gly Asn
            180                 185                 190

Asp Trp Ile Glu Val Ala Phe Arg Thr Ala Arg Gln Gly Asp Pro Ser
            195                 200                 205

Ala Lys Leu Cys Tyr Asn Asp Tyr Asn Ile Glu Asn Trp Asn Ala Ala
            210                 215                 220

Lys Thr Gln Ala Val Tyr Asn Met Val Arg Asp Phe Lys Ser Arg Gly
225                 230                 235                 240

Val Pro Ile Asp Cys Val Gly Phe Gln Ser His Phe Asn Ser Gly Asn
            245                 250                 255

Pro Tyr Asn Pro Asn Phe Arg Thr Thr Leu Gln Gln Phe Ala Ala Leu
            260                 265                 270

Gly Val Asp Val Glu Val Thr Glu Leu Asp Ile Glu Asn Ala Pro Ala
            275                 280                 285

Gln Thr Tyr Ala Ser Val Ile Arg Asp Cys Leu Ala Val Asp Arg Cys
290                 295                 300
```

```
Thr Gly Ile Thr Val Trp Gly Val Arg Asp Ser Asp Ser Trp Arg Ser
305                 310                 315                 320

Tyr Gln Asn Pro Leu Leu Phe Asp Asn Gly Asn Lys Lys Gln Ala
        325                 330                 335

Tyr Tyr Ala Val Leu Asp Ala Leu Asn Glu Gly Ser Asp Asp Gly Gly
                340                 345                 350

Gly Pro Ser Asn Pro Pro Val Ser Pro Pro Gly Gly Gly Ser Gly
        355                 360                 365

Gln Ile Arg Gly Val Ala Ser Asn Arg Cys Ile Asp Val Pro Asn Gly
        370                 375                 380

Asn Thr Ala Asp Gly Thr Gln Val Gln Leu Tyr Asp Cys His Ser Gly
385                 390                 395                 400

Ser Asn Gln Gln Trp Thr Tyr Thr Ser Ser Gly Glu Phe Arg Ile Phe
                405                 410                 415

Gly Asn Lys Cys Leu Asp Ala Gly Gly Ser Ser Asn Gly Ala Val Val
                420                 425                 430

Gln Ile Tyr Ser Cys Trp Gly Gly Ala Asn Gln Lys Trp Glu Leu Arg
                435                 440                 445

Ala Asp Gly Thr Ile Val Gly Val Gln Ser Gly Leu Cys Leu Asp Ala
        450                 455                 460

Val Gly Gly Gly Thr Gly Asn Gly Thr Arg Leu Gln Leu Tyr Ser Cys
465                 470                 475                 480

Trp Gly Gly Asn Asn Gln Lys Trp Ser Tyr Asn Ala
                485                 490

(2) INFORMATION FOR SEQ ID NO:8:

(i) SEQUENCE CHARACTERISTICS:
        (A) LENGTH: 491 amino acids
        (B) TYPE: amino acid
        (C) STRANDEDNESS: Not Relevant
        (D) TOPOLOGY: linear (ii) MOLECULE TYPE: peptide (viii) POSITION IN GENOME:
        (A) CHROMOSOME/SEGMENT: M64551

(xi) SEQUENCE DESCRIPTION: SEQ ID NO:8:

Met Gly Ser Tyr Ala Leu Pro Arg Ser Gly Val Arg Arg Ser Ile Arg
1               5                   10                  15

Val Leu Xaa Xaa Xaa Leu Ala Ala Leu Val Val Gly Val Leu Gly Thr
                20                  25                  30

Ala Thr Ala Leu Ile Ala Pro Pro Gly Ala His Ala Ala Glu Ser Thr
            35                  40                  45

Leu Gly Ala Ala Ala Gln Ser Gly Arg Tyr Phe Gly Thr Ala Ile
        50                  55                  60

Ala Ser Gly Arg Leu Ser Asp Ser Thr Tyr Thr Ser Ile Ala Gly Arg
65                  70                  75                  80

Glu Phe Asn Met Val Thr Ala Glu Asn Glu Met Lys Ile Asp Ala Thr
                85                  90                  95

Glu Pro Gln Arg Gly Gln Phe Asn Phe Ser Ser Ala Asp Arg Val Tyr
            100                 105                 110

Asn Trp Ala Val Gln Asn Gly Lys Gln Val Arg Gly His Thr Leu Ala
            115                 120                 125

Trp His Ser Gln Gln Pro Gly Trp Met Gln Ser Leu Ser Gly Arg Pro
        130                 135                 140
```

```
Leu Arg Gln Ala Met Ile Asp His Ile Asn Gly Val Met Ala His Tyr
145                 150                 155                 160

Lys Gly Lys Ile Val Gln Trp Asp Val Val Asn Glu Ala Phe Ala Asp
                165                 170                 175

Gly Ser Ser Gly Ala Arg Arg Asp Ser Asn Leu Gln Arg Ser Gly Asn
                180                 185                 190

Asp Trp Ile Glu Val Ala Phe Arg Thr Ala Arg Ala Ala Asp Pro Ser
            195                 200                 205

Ala Lys Leu Cys Tyr Asn Asp Tyr Asn Val Glu Asn Trp Thr Trp Ala
210                 215                 220

Lys Thr Gln Ala Met Tyr Asn Met Val Arg Asp Phe Lys Gln Arg Gly
225                 230                 235                 240

Val Pro Ile Asp Cys Val Gly Phe Gln Ser His Phe Asn Ser Gly Ser
                245                 250                 255

Pro Tyr Asn Ser Asn Phe Arg Thr Thr Leu Gln Asn Phe Ala Ala Leu
                260                 265                 270

Gly Val Asp Val Ala Ile Thr Glu Leu Asp Ile Gln Gly Ala Pro Ala
            275                 280                 285

Ser Thr Tyr Ala Asn Val Thr Asn Asp Cys Leu Ala Val Ser Arg Cys
290                 295                 300

Leu Gly Ile Thr Val Trp Gly Val Arg Asp Ser Asp Ser Trp Arg Ser
305                 310                 315                 320

Glu Gln Thr Pro Leu Leu Phe Asn Asn Asp Gly Ser Lys Lys Ala Ala
                325                 330                 335

Tyr Thr Ala Val Leu Asp Ala Leu Xaa Xaa Xaa Xaa Asn Gly Gly
            340                 345                 350

Asp Ser Ser Glu Pro Pro Xaa Xaa Xaa Xaa Xaa Ala Asp Gly Gly
            355                 360                 365

Gln Ile Lys Gly Val Gly Ser Gly Arg Cys Leu Asp Val Pro Asp Ala
370                 375                 380

Ser Thr Ser Asp Gly Thr Gln Leu Gln Leu Trp Asp Cys His Ser Gly
385                 390                 395                 400

Thr Asn Gln Gln Trp Ala Ala Thr Asp Ala Gly Glu Leu Arg Val Tyr
                405                 410                 415

Gly Asp Lys Cys Leu Asp Ala Ala Gly Thr Ser Asn Gly Ser Lys Val
                420                 425                 430

Gln Ile Tyr Ser Cys Trp Gly Gly Asp Asn Gln Lys Trp Arg Leu Asn
                435                 440                 445

Ser Asp Gly Ser Val Val Gly Val Gln Ser Gly Leu Cys Leu Asp Ala
450                 455                 460

Val Gly Asn Gly Thr Ala Asn Gly Thr Leu Ile Gln Leu Tyr Thr Cys
465                 470                 475                 480

Ser Asn Gly Ser Asn Gln Arg Trp Thr Arg Thr
                485                 490

(2) INFORMATION FOR SEQ ID NO:9:

(i) SEQUENCE CHARACTERISTICS:
        (A) LENGTH: 16 base pairs
        (B) TYPE: nucleic acid
        (C) STRANDEDNESS: both
        (D) TOPOLOGY: both (ii) MOLECULE TYPE: cDNA (ix) FEATURE:
        (A) NAME/KEY: CDS
```

(B) LOCATION: 2..16

(xi) SEQUENCE DESCRIPTION: SEQ ID NO:9:

T GGT CGC GAC ACC ACC                                                    16
  Gly Arg Asp Thr Thr
  1               5

(2) INFORMATION FOR SEQ ID NO:10:

(i) SEQUENCE CHARACTERISTICS:
        (A) LENGTH: 5 amino acids
        (B) TYPE: amino acid
        (D) TOPOLOGY: linear (ii) MOLECULE TYPE: protein (xi) SEQUENCE DESCRIPTION: SEQ ID NO:10:

Gly Arg Asp Thr Thr
1               5

(2) INFORMATION FOR SEQ ID NO:11:

(i) SEQUENCE CHARACTERISTICS:
        (A) LENGTH: 25 base pairs
        (B) TYPE: nucleic acid
        (C) STRANDEDNESS: both
        (D) TOPOLOGY: both (ii) MOLECULE TYPE: cDNA (ix) FEATURE:
         (A) NAME/KEY: CDS
         (B) LOCATION: 2..25

(xi) SEQUENCE DESCRIPTION: SEQ ID NO:11:

T GGT CGC GAC AAG CGC GAC ACC ACC                                        25
  Gly Arg Asp Lys Arg Asp Thr Thr
                          10

(2) INFORMATION FOR SEQ ID NO:12:

(i) SEQUENCE CHARACTERISTICS:
        (A) LENGTH: 8 amino acids
        (B) TYPE: amino acid
        (D) TOPOLOGY: linear (ii) MOLECULE TYPE: protein (xi) SEQUENCE DESCRIPTION: SEQ ID NO:12:

Gly Arg Asp Lys Arg Asp Thr Thr
1               5

(2) INFORMATION FOR SEQ ID NO:13:

(i) SEQUENCE CHARACTERISTICS:
        (A) LENGTH: 37 base pairs
        (B) TYPE: nucleic acid
        (C) STRANDEDNESS: both
        (D) TOPOLOGY: both (ii) MOLECULE TYPE: cDNA (ix) FEATURE:
         (A) NAME/KEY: CDS
         (B) LOCATION: 2..37

(xi) SEQUENCE DESCRIPTION: SEQ ID NO:13:

T GGC CAG TGT GGA GGT GAC ACC ACC ATC ACC CAG AAC                        37
  Gly Gln Cys Gly Gly Asp Thr Thr Ile Thr Gln Asn
      10              15                  20

(2) INFORMATION FOR SEQ ID NO:14:

(i) SEQUENCE CHARACTERISTICS:
        (A) LENGTH: 12 amino acids
        (B) TYPE: amino acid
        (D) TOPOLOGY: linear (ii) MOLECULE TYPE: protein (xi) SEQUENCE DESCRIPTION: SEQ ID NO:14:

```
Gly Gln Cys Gly Gly Asp Thr Thr Ile Thr Gln Asn
 1               5                  10
```

(2) INFORMATION FOR SEQ ID NO:15:

(i) SEQUENCE CHARACTERISTICS:
        (A) LENGTH: 37 base pairs
        (B) TYPE: nucleic acid
        (C) STRANDEDNESS: both
        (D) TOPOLOGY: both (ii) MOLECULE TYPE: cDNA (ix) FEATURE:
        (A) NAME/KEY: CDS
        (B) LOCATION: 2..37

(xi) SEQUENCE DESCRIPTION: SEQ ID NO:15:

```
T GGC CAG TGT GGA GGT CGC GAC AAG CGC GAC ACC ACC          37
  Gly Gln Cys Gly Gly Arg Asp Lys Arg Asp Thr Thr
         15                  20
```

(2) INFORMATION FOR SEQ ID NO:16:

(i) SEQUENCE CHARACTERISTICS:
        (A) LENGTH: 12 amino acids
        (B) TYPE: amino acid
        (D) TOPOLOGY: linear (ii) MOLECULE TYPE: protein (xi) SEQUENCE DESCRIPTION: SEQ ID NO:16:

```
Gly Gln Cys Gly Gly Arg Asp Lys Arg Asp Thr Thr
 1               5                  10
```

(2) INFORMATION FOR SEQ ID NO:17:

(i) SEQUENCE CHARACTERISTICS:
        (A) LENGTH: 14 amino acids
        (B) TYPE: amino acid
        (C) STRANDEDNESS: Not Relevant
        (D) TOPOLOGY: Not Relevant (ii) MOLECULE TYPE: peptide (viii) POSITION IN GENOME:
        (A) CHROMOSOME/SEGMENT: #1696

(xi) SEQUENCE DESCRIPTION: SEQ ID NO:17:

```
Ala Ala Ser Thr Leu Ala Glu Gly Ala Ala Gln His Asn Arg
 1               5                  10
```

(2) INFORMATION FOR SEQ ID NO:18:

(i) SEQUENCE CHARACTERISTICS:
        (A) LENGTH: 10 amino acids
        (B) TYPE: amino acid
        (C) STRANDEDNESS: Not Relevant
        (D) TOPOLOGY: Not Relevant (ii) MOLECULE TYPE: peptide (viii) POSITION IN GENOME:
            (A) CHROMOSOME/SEGMENT: #1697

(xi) SEQUENCE DESCRIPTION: SEQ ID NO:18:

Tyr Phe Gly Val Ala Ile Ala Ala Asn Arg
1               5                   10

(2) INFORMATION FOR SEQ ID NO:19:

(i) SEQUENCE CHARACTERISTICS:
            (A) LENGTH: 12 amino acids
            (B) TYPE: amino acid
            (C) STRANDEDNESS: Not Relevant
            (D) TOPOLOGY: Not Relevant (ii) MOLECULE TYPE: peptide (viii) POSITION IN GENOME:
            (A) CHROMOSOME/SEGMENT: #1698

(xi) SEQUENCE DESCRIPTION: SEQ ID NO:19:

Leu Asn Asp Ser Val Tyr Thr Asn Ile Ala Asn Arg
1               5                   10

(2) INFORMATION FOR SEQ ID NO:20:

(i) SEQUENCE CHARACTERISTICS:
            (A) LENGTH: 9 amino acids
            (B) TYPE: amino acid
            (C) STRANDEDNESS: Not Relevant
            (D) TOPOLOGY: Not Relevant (ii) MOLECULE TYPE: peptide (viii) POSITION IN GENOME:
            (A) CHROMOSOME/SEGMENT: #1699

(ix) FEATURE:
            (A) NAME/KEY: Peptide
            (B) LOCATION: 1
            (D) OTHER INFORMATION: /note= "Position 1 may be Asn,
                Gly or Xaa"

(xi) SEQUENCE DESCRIPTION: SEQ ID NO:20:

Xaa Thr Gly Ile Thr Val Xaa Gly Val
1               5

(2) INFORMATION FOR SEQ ID NO:21:

(i) SEQUENCE CHARACTERISTICS:
            (A) LENGTH: 11 amino acids
            (B) TYPE: amino acid
            (C) STRANDEDNESS: Not Relevant
            (D) TOPOLOGY: Not Relevant (ii) MOLECULE TYPE: peptide (viii) POSITION IN GENOME:
            (A) CHROMOSOME/SEGMENT: #1703

(ix) FEATURE:
            (A) NAME/KEY: Peptide
            (B) LOCATION: 1
            (D) OTHER INFORMATION: /note= "Position 1 may be His,
                Glu or Thr"

(ix) FEATURE:
            (A) NAME/KEY: Peptide
            (B) LOCATION: 2
            (D) OTHER INFORMATION: /note= "Position 2 may be Glu or Phe"

```
    (ix) FEATURE:
         (A) NAME/KEY: Peptide
         (B) LOCATION: 3
         (D) OTHER INFORMATION: /note= "Position 3 may be Leu or Asn"

(ix) FEATURE:
         (A) NAME/KEY: Peptide
         (B) LOCATION: 4
         (D) OTHER INFORMATION: /note= "Position 4 may be Val or Ser"

(ix) FEATURE:
         (A) NAME/KEY: Peptide
         (B) LOCATION: 5
         (D) OTHER INFORMATION: /note= "Position 5 may be Tyr or Val"

(ix) FEATURE:
         (A) NAME/KEY: Peptide
         (B) LOCATION: 6
         (D) OTHER INFORMATION: /note= "Position 6 may be Asn or Thr"

(ix) FEATURE:
         (A) NAME/KEY: Peptide
         (B) LOCATION: 7
         (D) OTHER INFORMATION: /note= "Position 7 may be Met or Ala"

(ix) FEATURE:
         (A) NAME/KEY: Peptide
         (B) LOCATION: 8
         (D) OTHER INFORMATION: /note= "Position 8 may be Val or Glu"

(ix) FEATURE:
         (A) NAME/KEY: Peptide
         (B) LOCATION: 9
         (D) OTHER INFORMATION: /note= "Position 9 may be Asn or Xaa"

(ix) FEATURE:
         (A) NAME/KEY: Peptide
         (B) LOCATION: 10
         (D) OTHER INFORMATION: /note= "Position 10 may be Glu or Xaa"

(ix) FEATURE:
         (A) NAME/KEY: Peptide
         (B) LOCATION: 11
         (D) OTHER INFORMATION: /note= "Position 11 may be Met or Xaa"

(xi) SEQUENCE DESCRIPTION: SEQ ID NO:21:

Xaa Xaa Xaa Xaa Xaa Xaa Xaa Xaa Xaa Xaa Xaa
1               5                   10

(2) INFORMATION FOR SEQ ID NO:22:

(i) SEQUENCE CHARACTERISTICS:
        (A) LENGTH: 12 amino acids
        (B) TYPE: amino acid
        (C) STRANDEDNESS: Not Relevant
        (D) TOPOLOGY: Not Relevant (ii) MOLECULE TYPE: peptide (viii) POSITION IN GENOME:
        (A) CHROMOSOME/SEGMENT: #1704

(xi) SEQUENCE DESCRIPTION: SEQ ID NO:22:

Glu Phe Asn Ser Val Thr Ala Glu Asn Glu Met Lys
1               5                   10

(2) INFORMATION FOR SEQ ID NO:23:

(i) SEQUENCE CHARACTERISTICS:
        (A) LENGTH: 14 amino acids
        (B) TYPE: amino acid
        (C) STRANDEDNESS: Not Relevant
        (D) TOPOLOGY: Not Relevant
```

(ii) MOLECULE TYPE: peptide (vi) ORIGINAL SOURCE:
            (A) ORGANISM: S. lividans (viii) POSITION IN GENOME:
            (A) CHROMOSOME/SEGMENT: XlnA (xi) SEQUENCE DESCRIPTION: SEQ ID NO:23:

Ala Glu Ser Thr Leu Gly Ala Ala Ala Ala Gln Ser Gly Arg
1               5                  10

(2) INFORMATION FOR SEQ ID NO:24:

(i) SEQUENCE CHARACTERISTICS:
            (A) LENGTH: 10 amino acids
            (B) TYPE: amino acid
            (C) STRANDEDNESS: Not Relevant
            (D) TOPOLOGY: Not Relevant (ii) MOLECULE TYPE: peptide (vi) ORIGINAL SOURCE:
            (A) ORGANISM: S. lividans (viii) POSITION IN GENOME:
            (A) CHROMOSOME/SEGMENT: XlnA (xi) SEQUENCE DESCRIPTION: SEQ ID NO:24:

Tyr Phe Gly Thr Ala Ile Ala Ser Gly Arg
1               5                  10

(2) INFORMATION FOR SEQ ID NO:25:

(i) SEQUENCE CHARACTERISTICS:
            (A) LENGTH: 12 amino acids
            (B) TYPE: amino acid
            (C) STRANDEDNESS: Not Relevant
            (D) TOPOLOGY: Not Relevant (ii) MOLECULE TYPE: peptide (vi) ORIGINAL SOURCE:
            (A) ORGANISM: S. lividans (viii) POSITION IN GENOME:
            (A) CHROMOSOME/SEGMENT: XlnA (xi) SEQUENCE DESCRIPTION: SEQ ID NO:25:

Leu Ser Asp Ser Thr Tyr Thr Ser Ile Ala Gly Arg
1               5                  10

(2) INFORMATION FOR SEQ ID NO:26:

(i) SEQUENCE CHARACTERISTICS:
            (A) LENGTH: 12 amino acids
            (B) TYPE: amino acid
            (C) STRANDEDNESS: Not Relevant
            (D) TOPOLOGY: Not Relevant (ii) MOLECULE TYPE: peptide (vi) ORIGINAL SOURCE:
            (A) ORGANISM: S. lividans (viii) POSITION IN GENOME:
            (A) CHROMOSOME/SEGMENT: XlnA (xi) SEQUENCE DESCRIPTION: SEQ ID NO:26:

Glu Phe Asn Met Val Thr Ala Glu Asn Glu Met Lys
1               5                  10

```
(2) INFORMATION FOR SEQ ID NO:27:

(i) SEQUENCE CHARACTERISTICS:
        (A) LENGTH: 13 amino acids
        (B) TYPE: amino acid
        (C) STRANDEDNESS: Not Relevant
        (D) TOPOLOGY: Not Relevant (ii) MOLECULE TYPE: peptide (vi) ORIGINAL SOURCE:
        (A) ORGANISM: S. lividans (viii) POSITION IN GENOME:
        (A) CHROMOSOME/SEGMENT: XlnA (xi) SEQUENCE DESCRIPTION: SEQ ID NO:27:

Ser Arg Cys Leu Gly Ile Thr Val Trp Gly Val Arg Asp
1               5                   10

(2) INFORMATION FOR SEQ ID NO:28:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Actinomadura sp. DSM43186

(viii) POSITION IN GENOME:
        (A) CHROMOSOME/SEGMENT: #1696s (xi) SEQUENCE DESCRIPTION: SEQ ID NO:28:

GCNGCNCAVA YAAYMG                                                       16

(2) INFORMATION FOR SEQ ID NO:29:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(iv) ANTI-SENSE: YES (vi) ORIGINAL SOURCE:
        (A) ORGANISM: Actinomadura sp. DSM43186

(viii) POSITION IN GENOME:
        (A) CHROMOSOME/SEGMENT: #1703as (xi) SEQUENCE DESCRIPTION: SEQ ID NO:29:

ACCATRTTRT ANACNA                                                       16

(2) INFORMATION FOR SEQ ID NO:30:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(iv) ANTI-SENSE: YES
```

(vi) ORIGINAL SOURCE:
            (A) ORGANISM: Actinomadura sp. DSM43186

(viii) POSITION IN GENOME:
            (A) CHROMOSOME/SEGMENT: #1704as (xi) SEQUENCE DESCRIPTION: SEQ ID NO:30:

TTCATYTCRT TYTCNGC                                                  17

(2) INFORMATION FOR SEQ ID NO:31:

(i) SEQUENCE CHARACTERISTICS:
            (A) LENGTH: 39 base pairs
            (B) TYPE: nucleic acid
            (C) STRANDEDNESS: single
            (D) TOPOLOGY: linear (ii) MOLECULE TYPE: DNA (genomic)

(iv) ANTI-SENSE: YES (vi) ORIGINAL SOURCE:
            (A) ORGANISM: S. lividans (viii) POSITION IN GENOME:
            (A) CHROMOSOME/SEGMENT: xlnA 331-369as (xi) SEQUENCE DESCRIPTION: SEQ ID NO:31:

CGTGAGTTCA ACATGGTGAC GGCCGAGAAC GAGATGAAG                          39

(2) INFORMATION FOR SEQ ID NO:32:

(i) SEQUENCE CHARACTERISTICS:
            (A) LENGTH: 28 base pairs
            (B) TYPE: nucleic acid
            (C) STRANDEDNESS: single
            (D) TOPOLOGY: linear (ii) MOLECULE TYPE: DNA (genomic)

(vi) ORIGINAL SOURCE:
            (A) ORGANISM: S. lividans (viii) POSITION IN GENOME:
            (A) CHROMOSOME/SEGMENT: xlnA 257-284s (xi) SEQUENCE DESCRIPTION: SEQ ID NO:32:

AGAGCGGCCG CTACTTCGGC ACCGCCAT                                      28

(2) INFORMATION FOR SEQ ID NO:33:

(i) SEQUENCE CHARACTERISTICS:
            (A) LENGTH: 32 base pairs
            (B) TYPE: nucleic acid
            (C) STRANDEDNESS: single
            (D) TOPOLOGY: linear (ii) MOLECULE TYPE: DNA (genomic)

(iv) ANTI-SENSE: YES (vi) ORIGINAL SOURCE:
            (A) ORGANISM: S. lividans (viii) POSITION IN GENOME:
            (A) CHROMOSOME/SEGMENT: xlnA 530-561as (xi) SEQUENCE DESCRIPTION: SEQ ID NO:33:

CACGCCGTTG ATGTGGTCGA TCATCGCCTG GC                                 32

(2) INFORMATION FOR SEQ ID NO:34:

(i) SEQUENCE CHARACTERISTICS:
    (A) LENGTH: 15 base pairs
    (B) TYPE: nucleic acid
    (C) STRANDEDNESS: both
    (D) TOPOLOGY: both (ii) MOLECULE TYPE: DNA (genomic)

(xi) SEQUENCE DESCRIPTION: SEQ ID NO:34:

CCGCGGACTG GCATC                                                                15

(2) INFORMATION FOR SEQ ID NO:35:

(i) SEQUENCE CHARACTERISTICS:
        (A) LENGTH: 16 base pairs
        (B) TYPE: nucleic acid
        (C) STRANDEDNESS: both
        (D) TOPOLOGY: both (ii) MOLECULE TYPE: DNA (genomic)

(xi) SEQUENCE DESCRIPTION: SEQ ID NO:35:

CCGCGGACTG CGCATC                                                               16

(2) INFORMATION FOR SEQ ID NO:36:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:36:

Pro Leu Tyr Gly Arg Asp Thr Thr
1               5

(2) INFORMATION FOR SEQ ID NO:37:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:37:

Pro Leu Tyr Gly Arg Asp Lys Arg Asp Thr Thr
1               5                   10

(2) INFORMATION FOR SEQ ID NO:38:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:38:

Pro Leu Tyr Gly Gln Cys Gly Gly Asp Thr Thr
1               5                   10

(2) INFORMATION FOR SEQ ID NO:39:

```
     (i) SEQUENCE CHARACTERISTICS:
          (A) LENGTH: 15 amino acids
          (B) TYPE: amino acid
          (C) STRANDEDNESS: single
          (D) TOPOLOGY: linear (ii) MOLECULE TYPE: peptide (xi) SEQUENCE DESCRIPTION: SEQ ID NO:39:

Pro Leu Tyr Gly Gln Cys Gly Gly Arg Asp Lys Arg Asp Thr Thr
1               5                   10                  15
```

What is claimed is:

1. A method for enzyme-aided bleaching, said method comprising adding culture medium to pulp, wherein said culture medium is obtained from culture of a recombinant host cell which is not *Actinomadura flexuosa*, said culture medium comprising a thermostable xylanase which is active at 50–80° C., wherein the amino acid sequence of said xylanase comprises an amino acid sequence of SEQ ID NO. 2 (FIGS. 13–13A) or a xylanolytic fragment thereof and wherein said host cell has been transformed with a recombinant vector that encodes said xylanase.

2. The method of claim 1, wherein said host is Trichoderma.

3. The method of claim 2, wherein said Trichoderma is *Trichoderma reesei*.

4. The method of claim 1, wherein the temperature is 70° C.

5. A method for enzyme-aided bleaching, said method comprising adding culture medium to pulp, wherein said culture medium is obtained from culture of a recombinant host cell which is not *Actinomadura flexuosa*, said culture medium comprising a thermostable xylanase which is active at 50–80° C., wherein the amino acid sequence of said xylanase comprises an amino acid sequence encoded by the nucleic acid sequence of a plasmid selected from the group consisting of pALK923 (DSM9322), pALK938 (DSM9899), pALK939 (DSM9900), pALK940 (DSM9901), pALK941 (DSM9902), pALK1056 (DSM9903) or a xylanolytic fragment thereof and wherein said host cell has been transformed with a recombinant vector that encodes said xylanase.

6. The method of claim 5, wherein said host is Trichoderma.

7. The method of claim 6, wherein said Trichoderma is *Trichoderma reesei*.

8. The method of claim 5, wherein the temperature is 70° C.

9. A method for chemically treating plant biomass comprising contacting said biomass with culture medium, wherein said culture medium is obtained from culture of a recombinant host cell which is not *Actinomadura flexuosa*, said culture medium comprising a thermostable xylanase which is active at 50–60° C., wherein the amino acid sequence of said xylanase comprises an amino acid sequence of SEQ ID NO. 2 (FIGS. 13–13A) or a xylanolytic fragment thereof and wherein said host cell has been transformed with a recombinant vector that encodes said xylanase.

10. The method of claim 9, wherein said host is Trichoderma.

11. The method of claim 10, wherein said Trichoderma is *Trichoderma reesei*.

12. The method of claim 9, wherein the temperature is 70° C.

13. A method for chemically treating plant biomass comprising contacting said biomass with culture medium, wherein said culture medium is obtained from culture of a recombinant host cell which is not *Actinomadura flexuosa*, said culture medium comprising a thermostable xylanase which is active at 50–80° C., wherein the amino acid sequence of said xylanase comprises an amino acid sequence encoded by the nucleic acid sequence of a plasmid selected from the group consisting of pALAK923 (DSM9322), pALK938 (DSM9899), pALK939 (DSM9900), pALK940 (DSM9901), pALK941 (DSM9902), pALK1056 (DSM9903) or a xylanolytic fragment thereof and wherein said host cell has been transformed with a recombinant vector that encodes said xylanase.

14. The method of claim 13, wherein said host is Trichoderma.

15. The method of claim 14, wherein said Trichoderma is *Trichoderma reesei*.

16. The method of claim 13, wherein the temperature is 70° C.

* * * * *